US012692260B2

(12) United States Patent
Kim et al.

(10) Patent No.: US 12,692,260 B2

(45) Date of Patent: Jul. 28, 2026

(54) COMPOUND HAVING INHIBITORY ACTIVITY AGAINST O-GLUSACASE AND USE THEREOF

(71) Applicant: MEDIFRON DBT INC., Seoul (KR)

(72) Inventors: Hee Kim, Anyang-si (KR); Hee Jin Ha, Ansan-si (KR); Hye Min Ju, Gunpo-si (KR); Ki Sun Roh, Seoul (KR); Jae Hong Im, Seoul (KR); Jin Mi Kang, Seoul (KR); Minyoung Lee, Incheon (KR)

(73) Assignee: MEDIFRON DBT INC., Seoul (KR)

( * ) Notice: Subject to any disclaimer, the term of this patent is extended or adjusted under 35 U.S.C. 154(b) by 517 days.

(21) Appl. No.: 18/037,895

(22) PCT Filed: Nov. 19, 2021

(86) PCT No.: PCT/KR2021/017053

§ 371 (c)(1),
(2) Date: May 19, 2023

(87) PCT Pub. No.: WO2022/108377

PCT Pub. Date: May 27, 2022

(65) Prior Publication Data

US 2024/0018135 A1 Jan. 18, 2024

(30) Foreign Application Priority Data

Nov. 23, 2020 (KR) ........................ 10-2020-0157343

(51) Int. Cl.

| | |
|---|---|
| ***C07D 417/14*** | (2006.01) |
| ***C07D 277/44*** | (2006.01) |
| ***C07D 417/04*** | (2006.01) |
| ***C07D 417/12*** | (2006.01) |

(52) U.S. Cl.

CPC ......... *C07D 417/14* (2013.01); *C07D 277/44* (2013.01); *C07D 417/04* (2013.01); *C07D 417/12* (2013.01)

(58) Field of Classification Search

CPC ................................ A61P 25/28; A61P 25/16

See application file for complete search history.

(56) References Cited

U.S. PATENT DOCUMENTS 10,913,733 B2 * 2/2021 McEachern .......... C07D 417/14
12,319,679 B2 * 6/2025 Genung ............... C07D 417/12

FOREIGN PATENT DOCUMENTS

CN 105143222 A 12/2015
CN 110300752 A 10/2019
CN 110312716 A 10/2019
CN 110325535 A 10/2019

(Continued)

OTHER PUBLICATIONS

Xiaoli Li et al., "Structure-based discovery and development of novel O-GlcNAcase inhibitors for the treatment of Alzheimer's disease", European Journal of Medicinal Chemistry, 2022, vol. 238, No. 114444, pp. 1-23 (23 pages).

(Continued)

*Primary Examiner* — Jeffrey S Lundgren
*Assistant Examiner* — Eric Tran
(74) *Attorney, Agent, or Firm* — Sughrue Mion, PLLC

(57) ABSTRACT

The present invention relates to a novel compound having inhibitory activity against O-GlcNAcase and a use thereof.

12 Claims, 1 Drawing Sheet

(56) References Cited

FOREIGN PATENT DOCUMENTS

| | | | |
|---|---|---|---|
| JP | 2020-503298 | A | 1/2020 |
| JP | 2020-503300 | A | 1/2020 |
| KR | 10-2054744 | B1 | 12/2019 |
| WO | 2017/106254 | A1 | 6/2017 |
| WO | 2018/109198 | A1 | 6/2018 |
| WO | 2018/109202 | A1 | 6/2018 |
| WO | 2019/178191 | A1 | 9/2019 |
| WO | 2020/061150 | A1 | 3/2020 |
| WO | 2020/117961 | A1 | 6/2020 |

OTHER PUBLICATIONS

Translation of Chinese Search Report dated Jun. 3, 2025 in Application No. 2021800760582.
Japanese Office Action dated May 13, 2025 in Application No. 2023-529081.
International Search Report for PCT/KR2021/017053 dated, Mar. 18, 2022 (PCT/ISA/210).

* cited by examiner

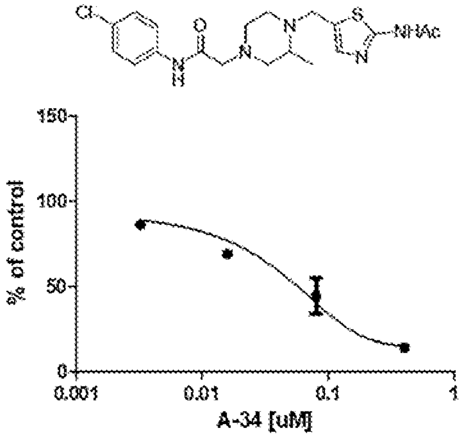
% of control
150
100
50
0
0.001
0.01
0.1
1
A-34 [uM]
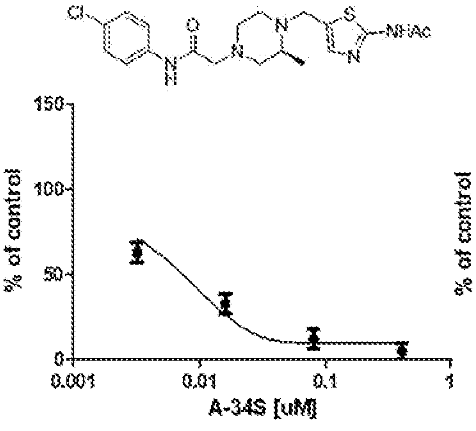
% of control
150
100
50
0
0.001
0.01
0.1
1
A-34S [uM]
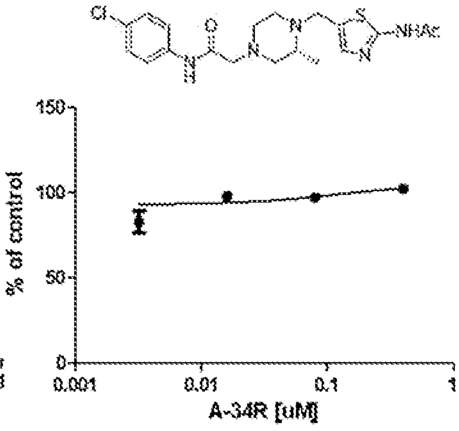
% of control
150
100
50
0
0.001
0.01
0.1
1
A-34R [uM]

COMPOUND HAVING INHIBITORY ACTIVITY AGAINST O-GLUSACASE AND USE THEREOF

CROSS REFERENCE TO RELATED APPLICATIONS

This application is a National Stage of International Application No. PCT/KR2021/017053 filed Nov. 19, 2021, claiming priority based on Korean Patent Application No. 10-2020-0157343, filed Nov. 23, 2020, the entire disclosures of which are incorporated herein by reference.

TECHNICAL FIELD

The present invention relates to a novel compound having inhibitory activity against O-GlcNAcase and a use thereof.

BACKGROUND ART

Microtubule-associated protein tau (MAPT) is an essentially unstructured protein and is elaborated through various reactions such as glycosylation and phosphorylation. The tau protein is aggregated by sequential hyperphosphorylation to form paired helical filaments (PHFs), and then form neurofibrillary tangles (NFTs). The NFTs formed above are one of the major pathological characteristics of Alzheimer's disease (AD) and tauopathy as a broader neurodegenerative disease. The normal function of phosphorylated tau is to promote and stabilize microtubule assembly. A healthy person includes an average of 1.9 phosphate groups per molecule of the tau protein, but in the brain of pathologically confirmed AD patients, soluble tau has an average of 2.6 phosphate groups per molecule, and tau purified from PHF has an average of 6 to 8 phosphate groups per molecule. In the AD patients, it means that the degree of phosphorylation of tau was increased 3 to 4 times compared to tau isolated from healthy brain tissue. Tau hyperphosphorylation not only promotes aggregation by itself, but also reduces microtubule stability by interfering with binding of tau and microtubule.

According to a study conducted 10 years ago, bovine tau was extensively post-translationally modified by binding of O-GlcNAc, and such a modification was observed in the same manner even in human tau. It has been found that O-GlcNAc is found on hydroxyl side chains of serine and threonine residues of various nuclear and cytoplasmic proteins, and in some cases, occurs on residues of proteins known to be phosphorylated. Like phosphorylation, O-GlcNAcylation is a dynamic modification and may be transferred to and removed from proteins several times during the lifetime of a polypeptide backbone. This dynamic cycle of O-GlcNAc is mediated by two enzymes. Uridine diphosphate N-acetyl-D-glucosamine polypeptidyltransferase OGT converts UDP-GlcNAc to GlcNAc by targeting hudroxyl groups of a receptor protein. Hydrolytic cleavage of O-GlcNAc from the modified protein is catalyzed by glycosidase called O-GlcNAcase or OGA.

The phosphorylation and O-GlcNAcylation of tau are reciprocally changed in culturing or metabolically activated rat brain slices. It may be estimated that the phosphorylation and O-GlcNAcylation of tau are in dynamic equilibrium by this interaction. The presence of phosphorylated and O-GlcNAcylated serine or threonine residues allows these residues to exist in one of three different states (phosphorylated, glycosylated, and free hydroxylated states). The formation of these states is regulated by appropriate enzymes. In addition, soluble tau in the brains of diseased individuals contains less O-GlcNAc, and insoluble tau aggregates are completely deficient in O-GlcNAc. Since O-GlcNAc is sensitive to glucose availability, it was estimated that such reduction and deficiency were caused by cerebral glucose metabolic disorder found in AD patients. The hyperphosphorylation of tau may be caused by a decrease in O-GlcNAc due to the reduced uptake of a hexosamine biosynthetic pathway (HBSP) and a resulting decrease in availability of UDP-GlcNAc. Reduced OGT activity or uncontrolled O-GlcNAcase may result in reduced tau O-GlcNAc level, leading to hyperphosphorylation of tau. A gene encoding O-GlcNAcase is present at a locus on chromosome 10q24.1 associated with an increased risk of late-onset AD, which is matched with the last hypothesis described above. An increase in tau O-GlcNAc level regardless of a source of the reduced O-GlcNAc in AD brain comprehensively opens the possibilities that tau hyperphosphorylation may be blocked and accumulation of toxic tau species may be prevented.

Attenuation of tau phosphorylation levels is actually considered to provide a pathway of slowing or stopping the disease progression in AD patients, and accordingly, many efforts have been currently focused on the development of kinase inhibitors for therapeutic effects. Considering that tau in the brains of AD patients exhibits lower O-GlcNAc levels than in normal brains, an alternative approach to limit tau phosphorylation may be considered using a dynamic balance between O-GlcNAcylation and phosphorylation. By inhibiting O-GlcNAcase in vivo, the O-GlcNAc level should increase while the tau phosphorylation level should decrease.

Although some high-potency O-GlcNAcase inhibitors have been discovered, these inhibitors have several limitations for eukaryotic O-GlcNAcases compared to functionally related eukaryotic enzymes. These limitations include moderate selectivity and chemical stability. In addition, one of the limitations was that a considerable amount was required to obtain the required amount. One kind of inhibitor, GlcNAcstatin, has been found to have picomolar efficacy against a bacterial homolog of O-GlcNAcase from *Clostridium perfringens*, but has not yet been tested even for any eukaryotic O-GlcNAcase. However, a structurally related inhibitor, gluco-nagstatin, was found to be active against human O-GlcNAcase with Ki of 420 nM. The reciprocal nature of O-GlcNAc and the phosphorylation of tau, and the possibility to use this relationship in vivo to limit the tau phosphorylation may cause strategies for limiting tau hyperphosphorylation in AD, which is a topic of interest.

In in-vitro studies using an inhibitor O-(2-acetamido-2-deoxy-D-glycopyranosylidene) amino-N-phenylcarbamate (PUGNAc), it was suggested that there is the possibility, but the inhibitor is not selective and does not cross the blood-brain barrier. Therefore, there was a need for a highly stable and selective inhibitor that easily crosses the blood-brain barrier and is more potent than existing compounds. In early studies of human O-GlcNAcase, it was found that this enzyme uses a catalytic mechanism including transient formation of a substrate-assisted catalyst and a non-covalently bound oxazoline intermediate from a 2-acetamido group. NAG-thiazoline superficially similar to this intermediate is a potent inhibitor of O-GlcNAcase because of its geometric similarity in a transition state. By changing most of thiazoline substituents, a potent (Ki ¼ 600 nM) inhibitor of O-GlcNAcase 800-fold more selective for human O-GlcNAcase than human lysosomal β-hexosaminidase is generated at pH 7.4. These thiazolines have good selectivity and reasonable potency, but have limited chemical stability in a solution for an extended period of several days to several weeks.

RELATED PRIOR ART

Korean Patent Registration No. 10-2054744.

DISCLOSURE

Technical Problem

In order to solve the above problems, the present inventors confirmed inhibitory activity against O-GlcNAcase of a novel compound, found that the compound inhibited tau phosphorylation, and then completed the present invention.

Therefore, an object of the present invention is to provide a novel compound having inhibitory activity against O-GlcNAcase and a use thereof as a pharmaceutical composition and a health functional food.

Technical Solution

In order to achieve the above object, one aspect of the present invention provides a compound represented by the following Chemical Formula 1 or a pharmaceutical salt thereof:

[Chemical Formula 1]

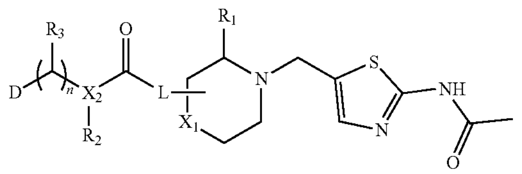

in which,

D is a ring selected from the group consisting of substitutable C3 to C10 cycloalkyl, substitutable 5-membered unsaturated or aromatic ring, substitutable 6-membered unsaturated or aromatic ring, substitutable 5-membered unsaturated or aromatic heterocyclic ring, and substitutable 6-membered unsaturated or aromatic heterocyclic ring, or a polycyclic ring in which two or more rings selected from the group are fused, $X_1$ is C, N, O or S, $X_2$ is N or O, $R_1$, $R_2$ and $R_3$ are each independently hydrogen or C1-C5 alkyl, L is a direct bond or a C1 to C12 alkylene group, and n is an integer of 0 to 3.

Another aspect of the present invention provides a pharmaceutical composition for treating or preventing diseases caused by hyperphosphorylation of tau, including the compound according to the present invention or a pharmaceutical salt thereof as an active ingredient.

Yet another aspect of the present invention provides a health functional food for improving or preventing diseases caused by hyperphosphorylation of tau, including the compound according to the present invention or a pharmaceutical salt thereof as an active ingredient.

Advantageous Effects

According to the present invention, the novel compound has a potent eukaryotic O-GlcNAcase inhibitor effect and may effectively reduce tau phosphorylation in vivo, thereby providing various uses as a therapeutic agent for tau-related diseases.

DESCRIPTION OF DRAWINGS

The FIGURE is a graph showing measurement of concentration-specific inhibitory ability against a human OGA enzyme of compounds A-34S and A-34R corresponding to enantiomers of a compound A-34 prepared in Example 1.

BEST MODE FOR THE INVENTION

Hereinafter, embodiments of the present invention will be described in detail with reference to the accompanying drawings. In the following description, detailed descriptions of techniques well-known to those skilled in the art may be omitted. Further, in describing the present invention, the detailed description of associated known functions or constitutions will be omitted if it is determined that they unnecessarily make the gist of the present invention unclear. Terminologies used herein are terminologies used to properly express preferred embodiments of the present invention, which may vary according to a user, an operator's intention, or customs in the art to which the present invention pertains.

Accordingly, definitions of the terminologies need to be described based on contents throughout this specification. Throughout the specification, unless explicitly described to the contrary, when a certain part "comprises" a certain component, it will be understood to imply the inclusion of stated elements but not the exclusion of any other elements.

Throughout this specification, the term "aromatic ring" means including at least one aromatic ring, and the "aromatic heterocyclic ring" means including at least one aromatic ring and at least one heterocyclic ring.

Throughout this specification, the term "hetero element" means an element other than carbon and hydrogen elements, for example, an element selected from the group consisting of N, O, S and P, but is not limited thereto.

The active substance of the present invention may be used in the form of a pharmaceutically acceptable salt, and an acid addition salt formed by a pharmaceutically acceptable free acid is useful as the salt. The expression "pharmaceutically acceptable salt" refers to any organic or inorganic addition salt of a base compound of the active substance of which side effects caused by the salt do not reduce the beneficial effect at a concentration having a relatively non-toxic and harmless effective effect to patients. These salts may use inorganic acids and organic acids as the free acid, as the inorganic acid, hydrochloric acid, bromic acid, nitric acid, sulfuric acid, perchloric acid, phosphoric acid, or the like may be used, and as the organic acid, citric acid, acetic acid, lactic acid, maleic acid, fumaric acid, gluconic acid, methanesulfonic acid, glycolic acid, succinic acid, tartaric acid, galacturonic acid, embonic acid, glutamic acid, aspartic acid, oxalic acid, (D) or (L) malic acid, maleic acid, methanesulfonic acid, ethanesulfonic acid, 4-toluenesulfonic acid, salicylic acid, citric acid, benzoic acid, malonic acid, or the like may be used. In addition, these salts include alkali metal salts (sodium salt, potassium salt, etc.), alkaline earth metal salts (calcium salt, magnesium salt, etc.), and the like. For example, the acid addition salts may include acetate, aspartate, benozate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulfate, naphthylate, 2-naphsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, zinc salts, etc., and preferably hydrochloride or trifluoroacetate among them.

The acid addition salt according to the present invention may be prepared by a conventional method, for example, a method of dissolving the active substance in an organic solvent such as methanol, ethanol, acetone, methylene chloride, acetonitrile, etc. and filtering and drying a precipitate produced by adding an organic or inorganic acid, or prepared by distilling the solvent and excess acid under reduced pressure, and then drying or crystallizing the mixture under an organic solvent.

In addition, the bases may be used to prepare pharmaceutically acceptable metal salts. An alkali metal salt or an alkaline earth metal salt may be obtained, for example, by dissolving the compound in an excess alkali metal hydroxide or alkaline earth metal hydroxide solution, filtering a non-dissolved compound salt, and then evaporating and drying a filtrate. At this time, as the metal salt, it is pharmaceutically suitable to prepare a sodium, potassium or calcium salt. Further, silver salts corresponding thereto may be obtained by reacting the alkali metal or alkaline earth metal salt with a suitable silver salt (e.g., silver nitrate).

Furthermore, the present invention includes not only the active substance and a pharmaceutically acceptable salt thereof, but also all solvates, hydrates, isomers, optical isomers and the like that may be prepared therefrom.

The present invention provides a compound represented by the following Chemical Formula 1 or a pharmaceutical salt thereof:

[Chemical Formula 1]

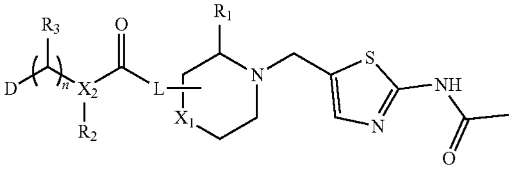

in which,

D is a ring selected from the group consisting of substitutable C3 to C10 cycloalkyl, substitutable 5-membered unsaturated or aromatic ring, substitutable 6-membered unsaturated or aromatic ring, substitutable 5-membered unsaturated or aromatic heterocyclic ring, and substitutable 6-membered unsaturated or aromatic heterocyclic ring, or a polycyclic ring in which two or more rings selected from the group are fused, $X_1$ is C, N, O or S, $X_2$ is N or O, $R_1$, $R_2$ and $R_3$ are each independently hydrogen or C1 to C5 alkyl, L is a direct bond or a C1 to C12 alkylene group, and n is an integer of 0 to 3.

In an embodiment of the present invention, the compound of Chemical Formula 1 above may be prepared by chemically covalent-bonding with lipoic acid and naringenin via a linker. Specifically, several novel compounds having different binding sites may be prepared by selectively reacting one of hydroxyl groups of naringenin reacting with lipoic acid, and in particular, various compound structures may be prepared through a multi-step reaction using various linkers such as ether, amide, and the like.

In an embodiment of the present invention, the compound of Chemical Formula 1 above may include compounds represented by the following Chemical Formulas 2 to 4:

[Chemical Formula 2]

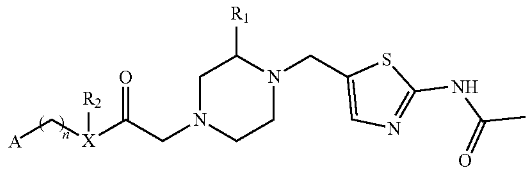

[Chemical Formula 3]

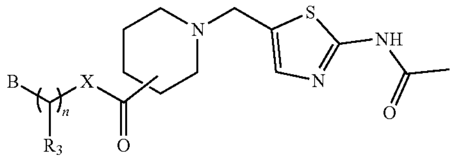

[Chemical Formula 4]

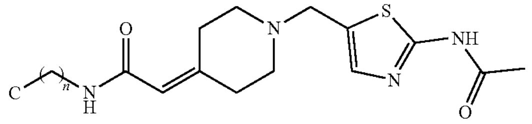

in which,

A, B, and C are each independently a ring selected from the group consisting of substitutable C3 to C10 cycloalkyl, substitutable 5-membered unsaturated or aromatic ring, substitutable 6-membered unsaturated or aromatic ring, substitutable unsaturated or aromatic heterocyclic ring, and substitutable 6-membered unsaturated or aromatic heterocyclic ring, or a polycyclic ring in which two or more rings selected from the group are fused, and $R_1$, $R_2$, $R_3$ and n are the same as defined in Chemical Formula 1 above.

In an embodiment of the present invention, in Chemical Formula 2 above, A may be selected from the following substituents, but is not limited thereto:

A

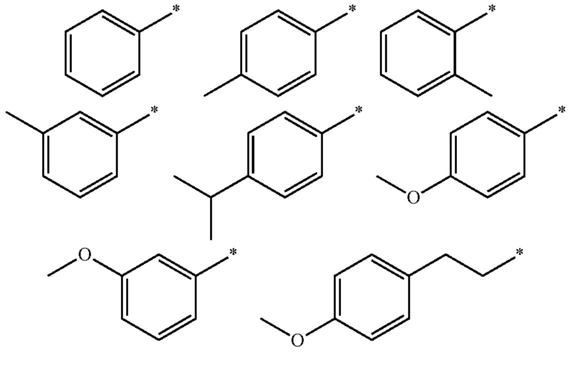

-continued

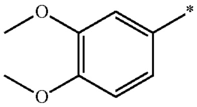
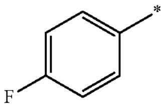
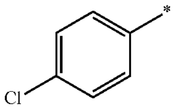
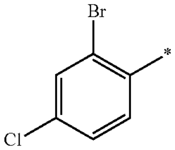
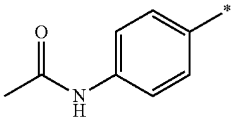
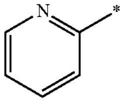
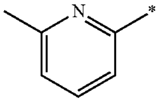
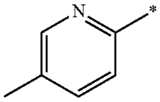
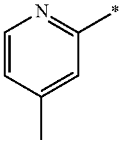
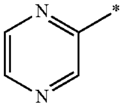
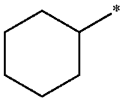
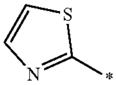
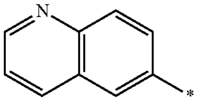
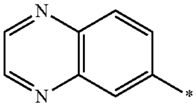
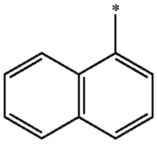
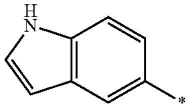

-continued

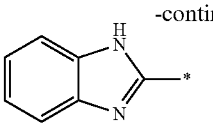
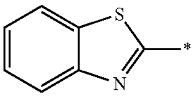
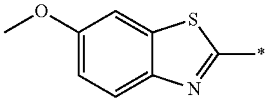
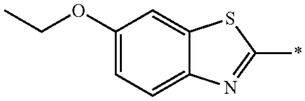
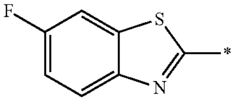
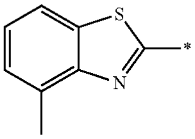
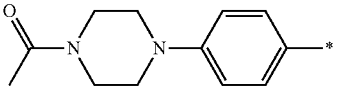
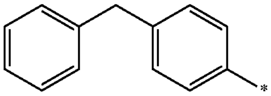
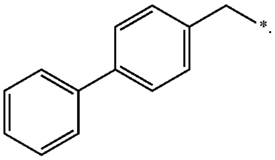

In an embodiment of the present invention, the compound of Chemical Formula 2 above may include the following compounds, but is not limited thereto:

| Code | Structure | Name |
|---|---|---|
| A-1 | 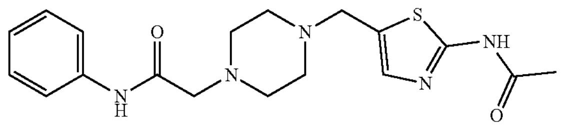 [SMILES: CC(=O)Nc1ncc(CN2CCN(CC(=O)Nc3ccccc3)CC2)s1] | 2-(4-((2-acetamidothiazol-5-yl) methyl)piperazin-1-yl)-N-phenylacetamide |
| A-2 | 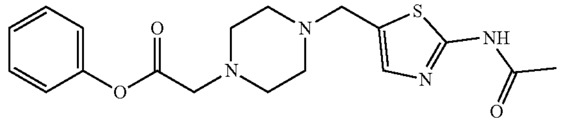 [SMILES: CC(=O)Nc1ncc(CN2CCN(CC(=O)Oc3ccccc3)CC2)s1] | phenyl 2-(4-((2-acetamidothiazol-5-yl)methyl)piperazin-1-yl) acetate |
| A-3 | 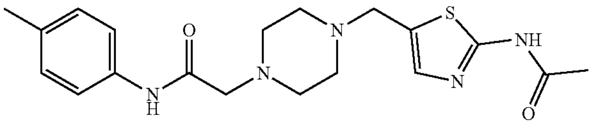 [SMILES: CC(=O)Nc1ncc(CN2CCN(CC(=O)Nc3ccc(C)cc3)CC2)s1] | 2-(4-((2-acclamidothiazol-5-yl) methyl)piperazin-1-yl)-N-(p-tolyl)acetamide |
| A-4 | 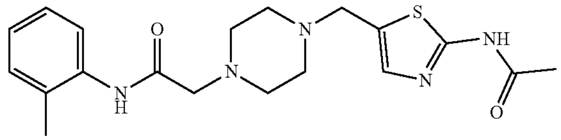 [SMILES: CC(=O)Nc1ncc(CN2CCN(CC(=O)Nc3ccccc3C)CC2)s1] | 2-(4-((2-acetamidothiazol-5-yl)methyl)piperazin-1-yl)-N-(o-tolyl)acetamide |
| A-5 | 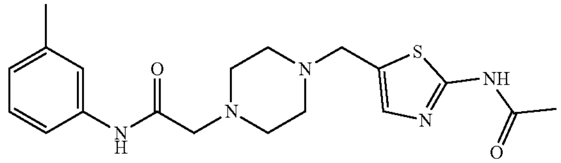 [SMILES: CC(=O)Nc1ncc(CN2CCN(CC(=O)Nc3cccc(C)c3)CC2)s1] | 2-(4-((2-acetamidothiazol-5-yl)methyl)piperazin-1-yl)-N-(m-tolyl)acetamide |

-continued

| Code | Structure | Name |
|---|---|---|
| A-6 | 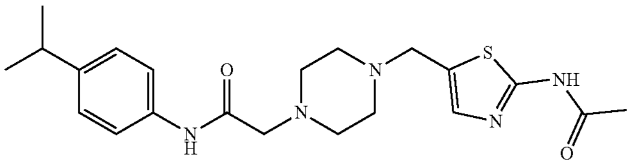 [SMILES: CC(=O)Nc1ncc(CN2CCN(CC(=O)Nc3ccc(C(C)C)cc3)CC2)s1] | 2-(4-((2-acetamidothiazol-5-yl)methyl)piperazin-1-yl)-N-(4-isopropylphenyl) acetamide |
| A-7 | 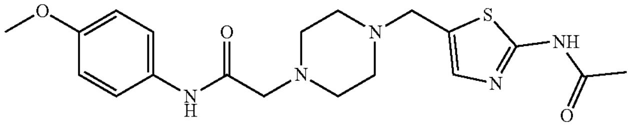 [SMILES: COc1ccc(NC(=O)CN2CCN(Cc3cnc(NC(C)=O)s3)CC2)cc1] | 2-(4-((2-acetamidothiazol-5-yl)methyl)piperazin-1-yl)-N-(4-methoxyphenyl) acetamide |
| A-8 | 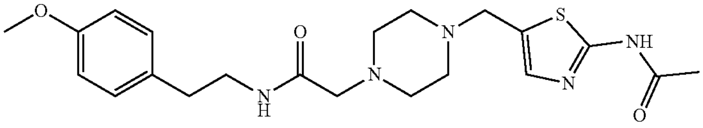 [SMILES: COc1ccc(CCNC(=O)CN2CCN(Cc3cnc(NC(C)=O)s3)CC2)cc1] | 2-(4-((2-acetamidothiazol-5-yl)methyl)piperazin-1-yl)-N-(4-methoxyphenethyl) acetamide |
| A-9 | 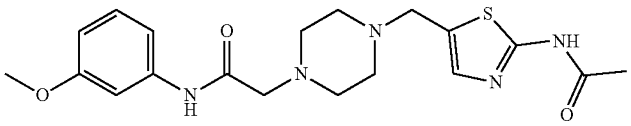 [SMILES: COc1cccc(NC(=O)CN2CCN(Cc3cnc(NC(C)=O)s3)CC2)c1] | 2-(4-((2-acetamidothiazol-5 yl)methyl)piperazin-1-yl)-N-(3-methoxyphenyl) acetamide. |
| A-10 | 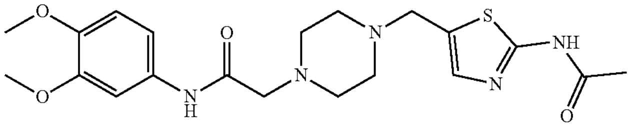 [SMILES: COc1ccc(NC(=O)CN2CCN(Cc3cnc(NC(C)=O)s3)CC2)cc1OC] | 2-(4-((2-acetamidothiazol-5-yl)methyl)piperazin-1-yl)-N-(3,4-dimethoxyphenyl) acetamide |
| A-11 | 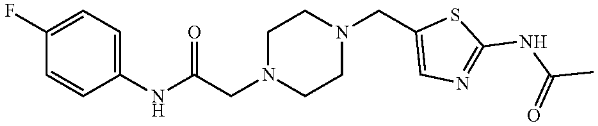 [SMILES: CC(=O)Nc1ncc(CN2CCN(CC(=O)Nc3ccc(F)cc3)CC2)s1] | 2-(4-((2-acetamidothiazol-5-yl)methyl)piperazin-1-yl)-N-(4-fluorophenyl)acetamide |
| A-12 | 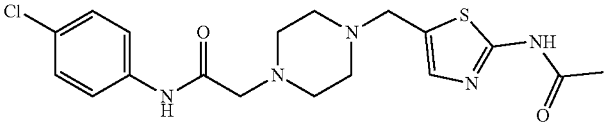 [SMILES: CC(=O)Nc1ncc(CN2CCN(CC(=O)Nc3ccc(Cl)cc3)CC2)s1] | 2-(4-((2-acetamidothiazol-5-yl)methyDpiperazin-1-yl)-N-(4-chlorophenyl)acetamide |
| A-13 | 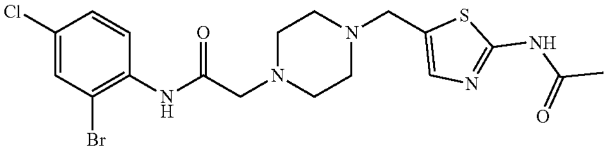 [SMILES: CC(=O)Nc1ncc(CN2CCN(CC(=O)Nc3ccc(Cl)cc3Br)CC2)s1] | 2-(4-((2-acetamidothiazol-5-yl)methyljpiperazin-1-yl)-N-(2-bromo-4-chlorophenyl) acetamide |
| A-14 | 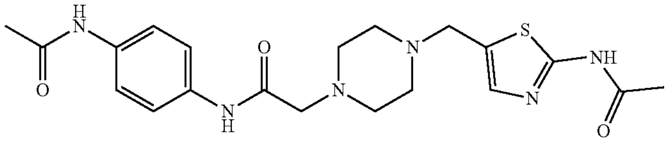 [SMILES: CC(=O)Nc1ccc(NC(=O)CN2CCN(Cc3cnc(NC(C)=O)s3)CC2)cc1] | N-(4-acetamidophenyl)-2-(4-((2-acctamidothiazol-5-yl) methyl)piperaxin-1-yl) acetamide |
| A-15 | 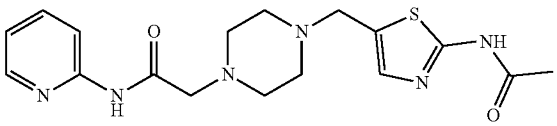 [SMILES: CC(=O)Nc1ncc(CN2CCN(CC(=O)Nc3ccccn3)CC2)s1] | 2-(4-((2-acetamidothiazol-5-yl)methyl)piperazin-1-yl) N-(pyridin-2-yl)acetamide |

-continued

| Code | Structure | Name |
|---|---|---|
| A-16 | 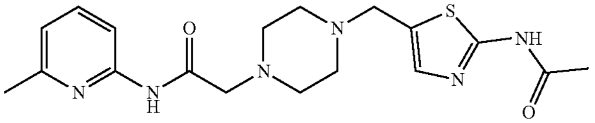 [SMILES: CC(=O)Nc1ncc(CN2CCN(CC(=O)Nc3cccc(C)n3)CC2)s1] | 2-(4-((2-acctamidothiazol-5-yl)methylpiperazin-1-yl)-N-(6-methylpyridin-2-yl) acetamide |
| A-17 | 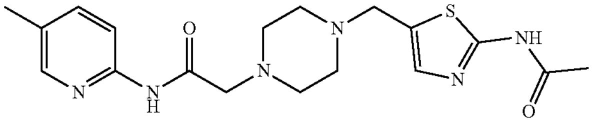 [SMILES: CC(=O)Nc1ncc(CN2CCN(CC(=O)Nc3ccc(C)cn3)CC2)s1] | 2-(4-((2-acetamidothiazol-5-yl)methyl)piperazin-1-yl)-N-(5-methylpyridin-2-yl) acetamide |
| A-18 | 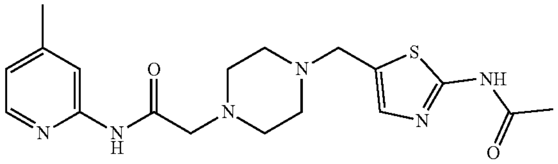 [SMILES: CC(=O)Nc1ncc(CN2CCN(CC(=O)Nc3cc(C)ccn3)CC2)s1] | 2-(4-((2-acetamidothiazol-5-yl)methyl)piperazin-1-yl)-N-(4-methylpyridin-2-yl) acetamide |
| A-19 | 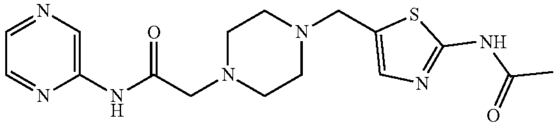 [SMILES: CC(=O)Nc1ncc(CN2CCN(CC(=O)Nc3cnccn3)CC2)s1] | 2-(4-((2-acetamidothiazol-6-yl)methyl)piperazin-1-yl)-N-(pyrazin-2-y])acetamide |
| A-20 | 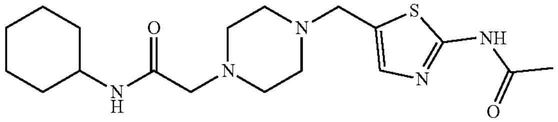 [SMILES: CC(=O)Nc1ncc(CN2CCN(CC(=O)NC3CCCCC3)CC2)s1] | 2-(4-((2-acetamidothiazol-5-yl)methyl)piperazin-1-yl)-N-cyclohexylacetamide |
| A-21 | 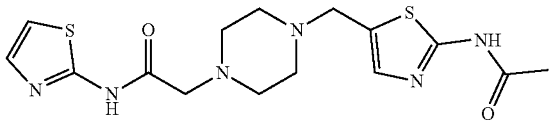 [SMILES: CC(=O)Nc1ncc(CN2CCN(CC(=O)Nc3nccs3)CC2)s1] | 2-(4-((2-acetainidothiazol-5-yl)methyl)piperazin-1-yl)-N-(thiazol-2-yl)acetamide |
| A-22 | 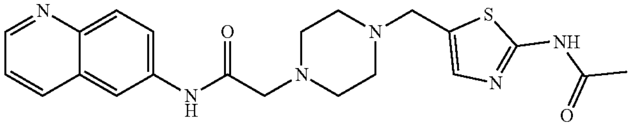 [SMILES: CC(=O)Nc1ncc(CN2CCN(CC(=O)Nc3ccc4ncccc4c3)CC2)s1] | 2-(4-((2-acetamnidothiazol-5-yl)methyl)piperazin-1-yl)-N-(quinolin-6-yl)acetamide |
| A-23 | 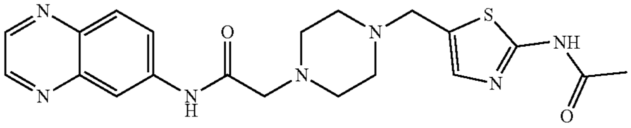 [SMILES: CC(=O)Nc1ncc(CN2CCN(CC(=O)Nc3ccc4nccnc4c3)CC2)s1] | 2-(4-((2-acetamidothiazol-5-yl)methylpiperazin-1-yl)-N-(quinoxalin-6-yl) acetamide |
| A-24 | 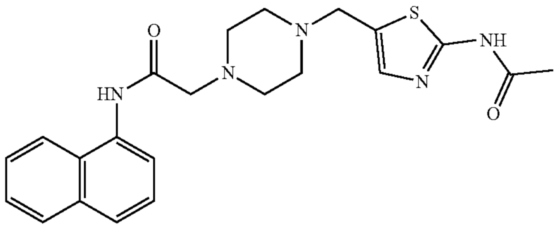 [SMILES: CC(=O)Nc1ncc(CN2CCN(CC(=O)Nc3cccc4ccccc34)CC2)s1] | 2-(4-((2-acetamidothiazol-5-yl)methyl)piperazin-1-yl)-N-(naphthalen-1-yl) acetamide |
| A-25 | 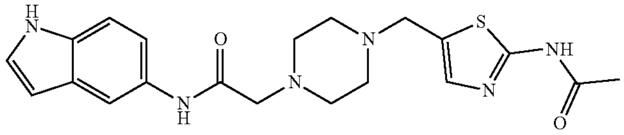 [SMILES: CC(=O)Nc1ncc(CN2CCN(CC(=O)Nc3ccc4[nH]ccc4c3)CC2)s1] | 2-(4-((2-acetamidothiazol-5-yl)methyl)piperazin-1-yl)-N-(1H-indol-5-yl)acetamide |

-continued

| Code | Structure | Name |
|---|---|---|
| A-26 | 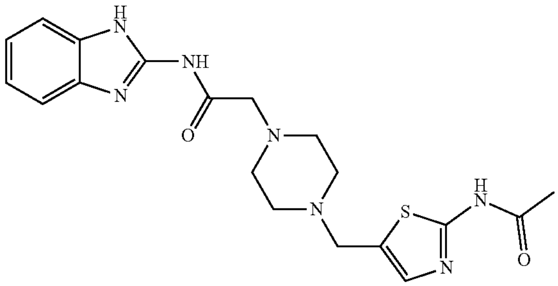 [SMILES: CC(=O)Nc1ncc(CN2CCN(CC(=O)Nc3nc4ccccc4[nH]3)CC2)s1] | 2-(4-((2-acetamnidothiazol-5-yl)methyl)piperazin-1-yl)-N-(1H-benzo[d]imidazol-2-yl)acetamide |
| A-27 | 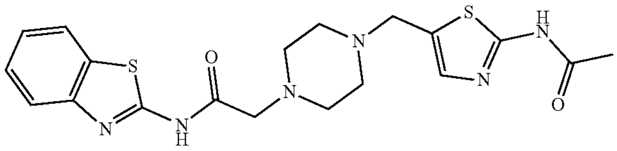 [SMILES: CC(=O)Nc1ncc(CN2CCN(CC(=O)Nc3nc4ccccc4s3)CC2)s1] | 2-(4-((2-acctamidothiazol-5-yl)methyl)piperazin-1-yl)-N-(benzo[d]thiazol-2-yl) acetamide |
| A-28 | 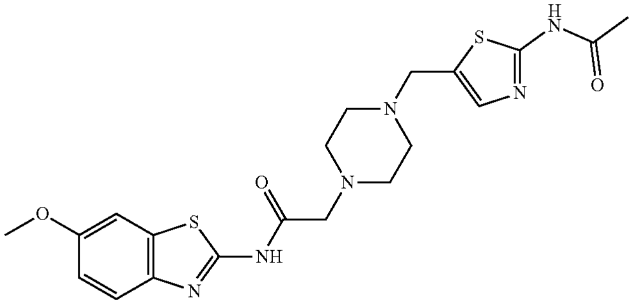 [SMILES: COc1ccc2nc(NC(=O)CN3CCN(Cc4cnc(NC(C)=O)s4)CC3)sc2c1] | 2-(4-((2-acetamidothiazol-5-yl)methyl)piperazin-1-yl)-N-(6-methoxybenzo[d]thiazol-2-yl)acetamide |
| A-29 | 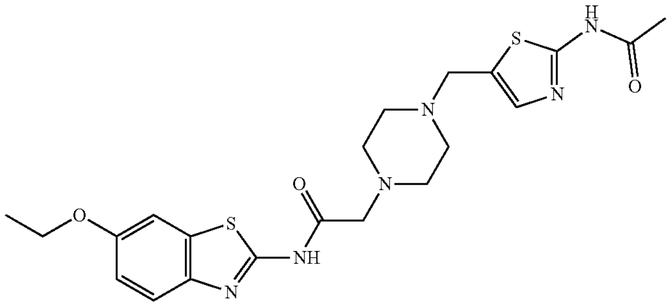 [SMILES: CCOc1ccc2nc(NC(=O)CN3CCN(Cc4cnc(NC(C)=O)s4)CC3)sc2c1] | 2-(4-((2-acctamidothiazol-5-ylmethyl)piperazin-1-yl)-2-yl)acemmide |
| A-30 | 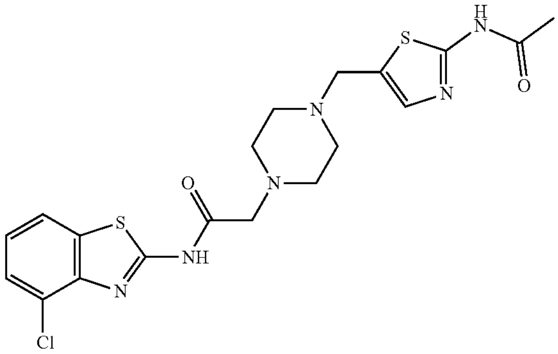 [SMILES: CC(=O)Nc1ncc(CN2CCN(CC(=O)Nc3nc4c(Cl)cccc4s3)CC2)s1] | 2-(4-((2-acctamidothiazol-5-yl)methyl)piperazin-1-yl)-N-(4-chlorobenzo[d]thiazol-2-yl)acetamide |
| A-31 | 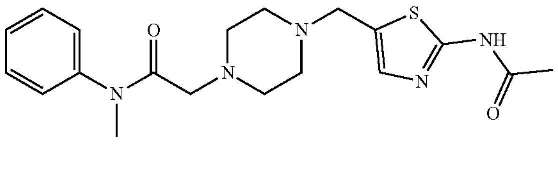 [SMILES: CC(=O)Nc1ncc(CN2CCN(CC(=O)N(C)c3ccccc3)CC2)s1] | 2-(4-((2-acetamidothiazol-5-yl)methyl)piperazin-1-yl)-N-methyl-N-phenylacetamide |

-continued

| Code | Structure | Name |
|---|---|---|
| A-32 | 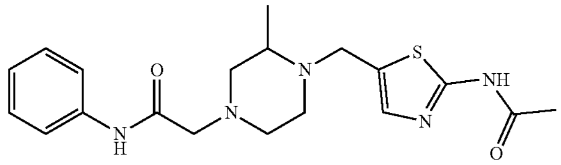 [SMILES: CC(=O)Nc1ncc(CN2CCN(CC(=O)Nc3ccccc3)CC2C)s1] | 2-(4-((2-acetamnidothiazol-5-yl)methyl)-3-methylpiperazin-1-yl)-N-phenylacetamide |
| A-33 | 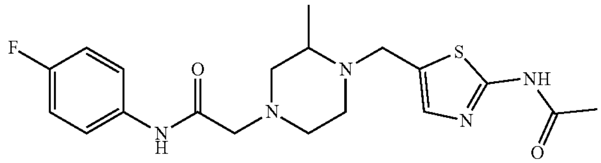 [SMILES: CC(=O)Nc1ncc(CN2CCN(CC(=O)Nc3ccc(F)cc3)CC2C)s1] | 2-(4-((2-acetamidothiazol-5-yl) yl)methyl)-3-methylpiperazin-1-yl)-N-(4-fluorophenyl) acetamide |
| A-34 | 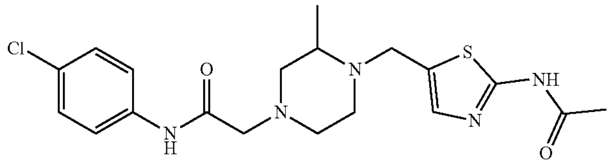 [SMILES: CC(=O)Nc1ncc(CN2CCN(CC(=O)Nc3ccc(Cl)cc3)CC2C)s1] | 2-(4-((2-acetamidothiazol-5-yl)methyl)-3-methylpiperazin-1-yl)-N-(4-chlorophenyl) acetamide |
| A-35 | 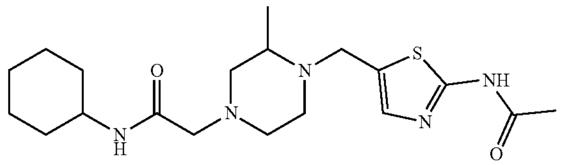 [SMILES: CC(=O)Nc1ncc(CN2CCN(CC(=O)NC3CCCCC3)CC2C)s1] | 2-(4-((2-acetamidothiazol-5-yl)methyl)-3-methylpiperazin-1-yl)-N-cyclohexylacetamide |
| A-36 | 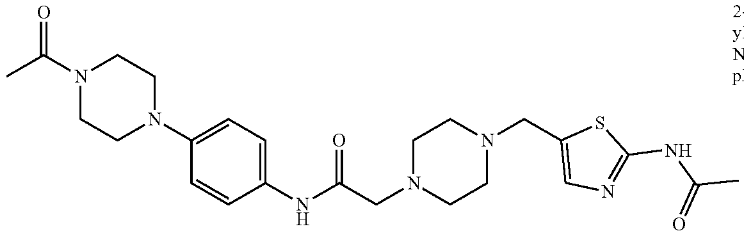 [SMILES: CC(=O)Nc1ncc(CN2CCN(CC(=O)Nc3ccc(N4CCN(C(C)=O)CC4)cc3)CC2)s1] | 2-(4-((2-acctamidothiazol-5-yl)methyl)piperazin-1-yl)-N-(4-(4-acetylpiperazin-1-yl) phenyl)acetamide |
| A-37 | 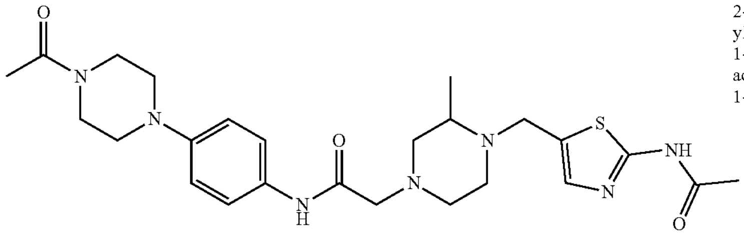 | 2-(4-((2-acetamidothiazol-5-yl)methyl)-3-methylpiperazin-1-yl)-N-(4-(4-acetylpiperazin-1-ylphenylacelamide |
| A-38 | 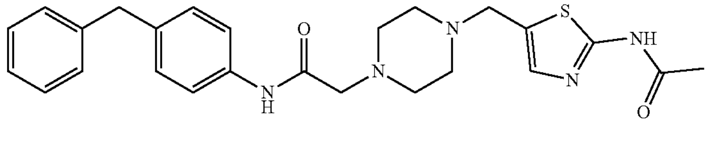 [SMILES: CC(=O)Nc1ncc(CN2CCN(CC(=O)Nc3ccc(Cc4ccccc4)cc3)CC2)s1] | 2-(4-((2-acetamidothiazol-5-yl)methyl)piperazin-1-yl)-N-(4-benzylpheny]) acetamide |
| A-39 | 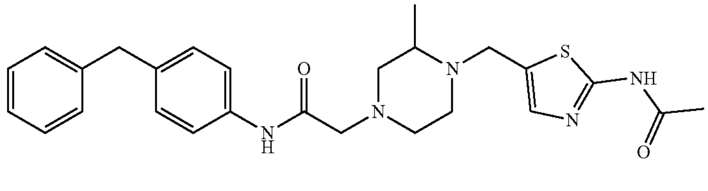 [SMILES: CC(=O)Nc1ncc(CN2CCN(CC(=O)Nc3ccc(Cc4ccccc4)cc3)CC2C)s1] | 2-(4-((2-acetamidothiazol-5-yl)methyl)-3-methylpiperazin-1-yl)-N-(4-benzylphenyl) acetamide |

-continued

| Code | Structure | Name |
|---|---|---|
| A-40 | 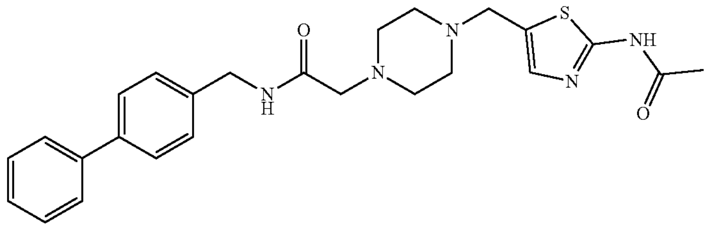 [SMILES: CC(=O)Nc1ncc(CN2CCN(CC(=O)NCc3ccc(-c4ccccc4)cc3)CC2)s1] | N-([1.1'-biphenyl]]-4-ylmethyl)-2-(4-((2-acetamidothiazol-5-yl)methyl)piperazin-1-yl)acetamide |
| A-41 | 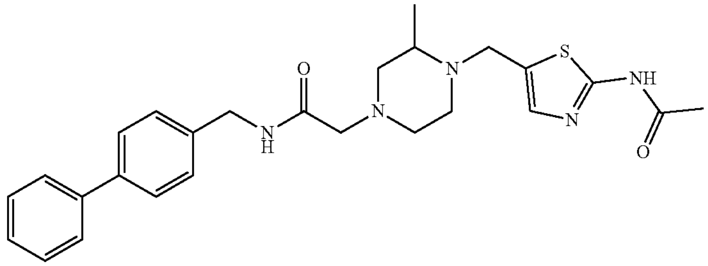 [SMILES: CC(=O)Nc1ncc(CN2CCN(CC(=O)NCc3ccc(-c4ccccc4)cc3)CC2C)s1] | N-([1,1'-biphenyl]-4-ylmethyl)-2-(4-((2-acetamidothiazol-5-yl)methyl)-3-methylpiperazin-1-yl)acetamide |

Preferably, the compound A-34 may be a compound A-34S represented by Chemical Formula 5 below as a (S)-form compound of enantiomers.

[Chemical Formula 5]

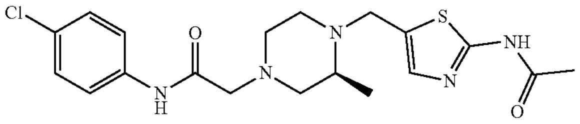

In an embodiment of the present invention, in Chemical Formula 3 above, B may be selected from the following substituents, but is not limited thereto:

B

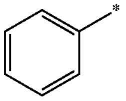 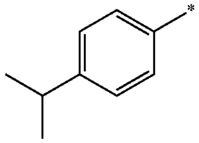 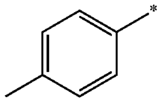

-continued

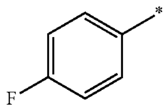 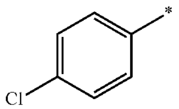 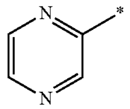

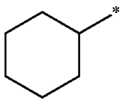 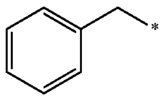 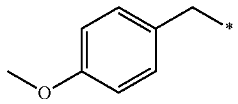

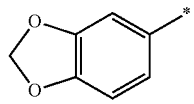 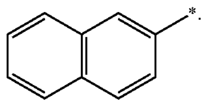

In an embodiment of the present invention, the compound of Chemical Formula 3 above may include the following compounds, but is not limited thereto:

| Code | Structure | Name |
|---|---|---|
| B-1 | 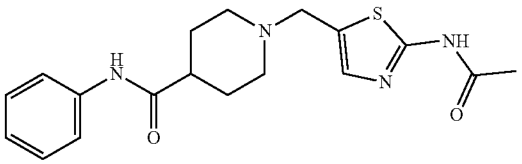 [SMILES: CC(=O)Nc1ncc(CN2CCC(C(=O)Nc3ccccc3)CC2)s1] | 1-((2-acetamidothiazol-5-yl)methyl)-N-phenylpiperidine-4-carboxamide |
| B-2 | 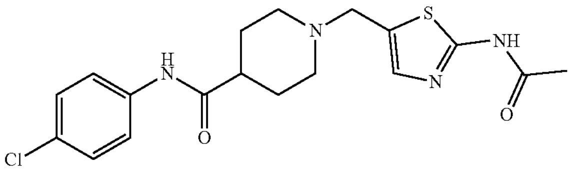 [SMILES: CC(=O)Nc1ncc(CN2CCC(C(=O)Nc3ccc(Cl)cc3)CC2)s1] | 1-((2-acetamidothiazol-5-yl)methyl)-N-(4-chlorophenyl) piperidine-4-carboxamide |

-continued

| Code | Structure | Name |
| --- | --- | --- |
| B-3 | 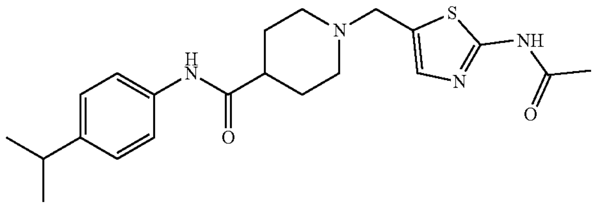 [SMILES: CC(=O)Nc1ncc(CN2CCC(C(=O)Nc3ccc(C(C)C)cc3)CC2)s1] | 1-((2-acetamidothiazol-5-yl)methyl)-N-(4-isopropylphenyl) piperidine-4-carboxamide |
| B-4 | 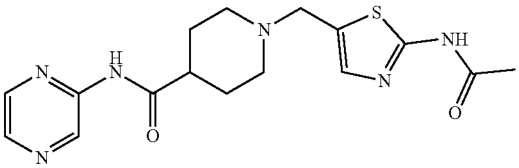 [SMILES: CC(=O)Nc1ncc(CN2CCC(C(=O)Nc3cnccn3)CC2)s1] | 1-((2-acetamidothiazol-5-yl)methyl)-N-(pyrazin-2-yl)piperidine-4-carboxamide |
| B-5 | 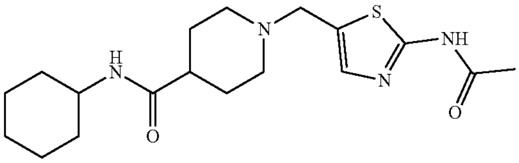 [SMILES: CC(=O)Nc1ncc(CN2CCC(C(=O)NC3CCCCC3)CC2)s1] | 1-((2-acetamidothiazol-5-yl)methyl)-N-cyclohexylpiperdine-4-carboxamide |
| B-6 | 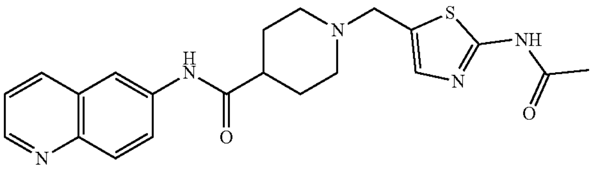 [SMILES: CC(=O)Nc1ncc(CN2CCC(C(=O)Nc3ccc4ncccc4c3)CC2)s1] | 1-((2-acetamidothiazol-5-ylmethyl)-N-(pyrazin-2-yl)piperidine-4-carboxamide |
| B-7 | 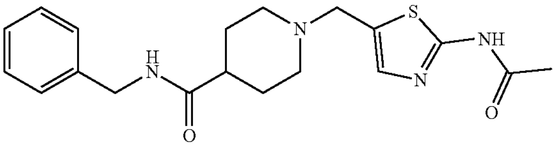 [SMILES: CC(=O)Nc1ncc(CN2CCC(C(=O)NCc3ccccc3)CC2)s1] | 1-((2-acetamidothiazol-5-ylmethyl)-N-benzylpiperidine-4-carboxamide |
| B-8 | 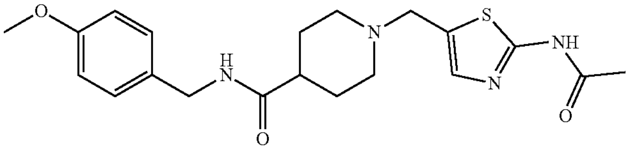 [SMILES: COc1ccc(CNC(=O)C2CCN(Cc3cnc(NC(C)=O)s3)CC2)cc1] | 1-((2-acetamidothiazol-5-yl)methyl)-N-(4-methoxybenzyl)piperidine-4-carboxamide |
| B-9 | 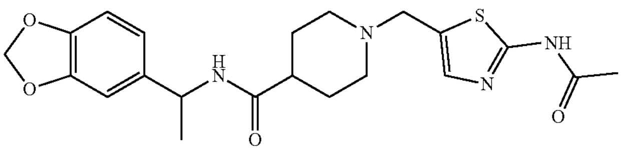 [SMILES: CC(=O)Nc1ncc(CN2CCC(C(=O)NC(C)c3ccc4c(c3)OCO4)CC2)s1] | 1-((2-acetamidothiazol-5-ylmethyl)-N-(1-(benzo [d][1,3]dioxol-5-yl)ethyl) piperidine-4-carboxamide |
| B-10 | 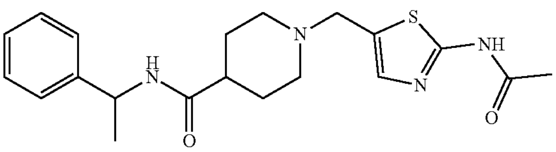 [SMILES: CC(=O)Nc1ncc(CN2CCC(C(=O)NC(C)c3ccccc3)CC2)s1] | 1-((2-acetamidothiazol-5-yl)methyl)-N-(1-phenylethybpiperidine-4-carboxamide |
| B-11 | 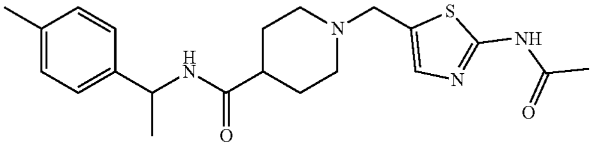 [SMILES: CC(=O)Nc1ncc(CN2CCC(C(=O)NC(C)c3ccc(C)cc3)CC2)s1] | 1-((2-acetamidothiazol-5-yl)methyl)-N-(1-(p-tol yl)ethyl)piperidine-4-carboxamide |

-continued

| Code | Structure | Name |
| --- | --- | --- |
| B-12 | 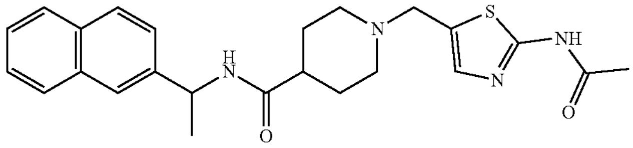 [SMILES: CC(=O)Nc1ncc(CN2CCC(C(=O)NC(C)c3ccc4ccccc4c3)CC2)s1] | 1-((2-acetamidothiazol-5-yl)methyl)-N-(1-(naphthalen-2-yl)ethyl) piperidine-4-carboxamide |
| B-13 | 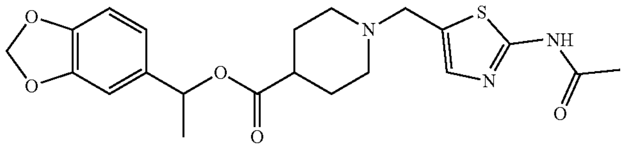 [SMILES: CC(=O)Nc1ncc(CN2CCC(C(=O)OC(C)c3ccc4c(c3)OCO4)CC2)s1] | 1-(benzo[d][1,3]dioxo]-5-yl)ethyl 1-((2-acetamidothiazol-S-yl)methyl)piperidine-4-carboxylate |
| B-14 | 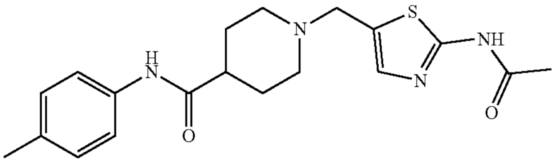 [SMILES: CC(=O)Nc1ncc(CN2CCC(C(=O)Nc3ccc(C)cc3)CC2)s1] | 1-((2-acetamidothiazol-5-yl)methyl)-N-(p-tolyl) piperidine-4-carboxamide |
| B-15 | 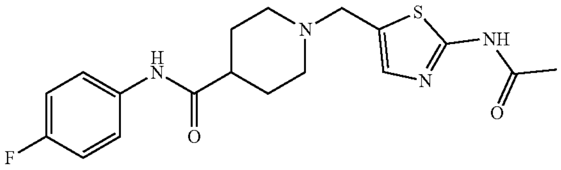 [SMILES: CC(=O)Nc1ncc(CN2CCC(C(=O)Nc3ccc(F)cc3)CC2)s1] | 1-((2-acetamidothiazol-5-yl)methyl)-N-(4-fluorophenyl) piperdine-4-carboxamide |
| B-16 | 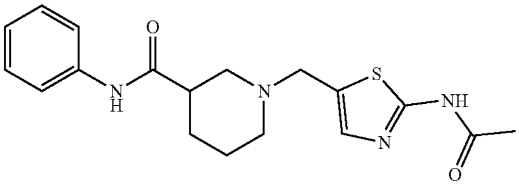 [SMILES: CC(=O)Nc1ncc(CN2CCCC(C(=O)Nc3ccccc3)C2)s1] | 1-((2-acetamidothiazo)-5-yl)methyl)-N-phenylpiperdine-3-carboxamide |
| B-17 | 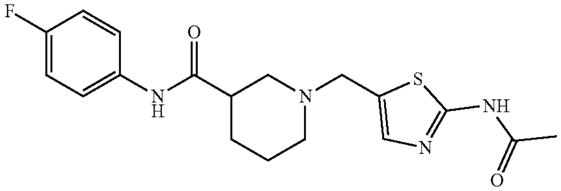 [SMILES: CC(=O)Nc1ncc(CN2CCCC(C(=O)Nc3ccc(F)cc3)C2)s1] | 1-((2-acetamidothiazol-5-yl)methyl)-N-(4-flurophenyl)piperdine-3-carboxamide |
| B-18 | 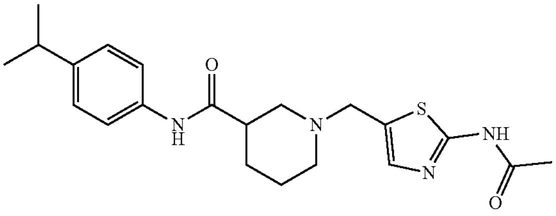 [SMILES: CC(=O)Nc1ncc(CN2CCCC(C(=O)Nc3ccc(C(C)C)cc3)C2)s1] | 1-((2-acetamidothiazol-5-yl)methyl)-N-(4-isopropylphenyl) piperdine-3-carboxamide |
| B-19 | 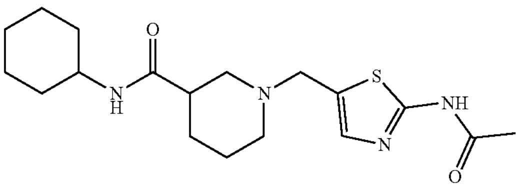 [SMILES: CC(=O)Nc1ncc(CN2CCCC(C(=O)NC3CCCCC3)C2)s1] | 1-((2-acetamidothiazol-5-yl)methyl)-N-cyclohexylpiperidine-3-carboxamide |

In an embodiment of the present invention, in Chemical Formula 4 above, C may be selected from the following substituents, but is not limited thereto:

C:

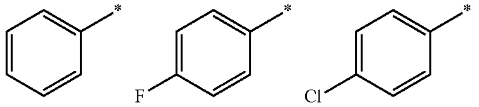

-continued

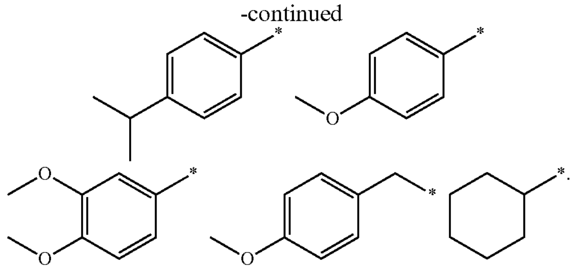

In an embodiment of the present invention, the compound of Chemical Formula 4 above may include the following compounds, but is not limited thereto:

| Code | Structure | Name |
|---|---|---|
| C-1 | 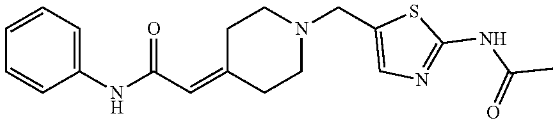 [SMILES: CC(=O)Nc1ncc(CN2CCC(=CC(=O)Nc3ccccc3)CC2)s1] | 2-(1-((2-acetamidothiazol-5-y))methyl)piperidin-4-ylidene)-N-phenylacetamide |
| C-2 | 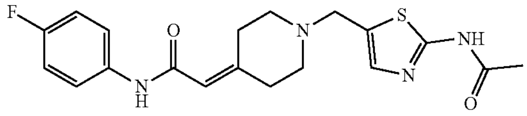 [SMILES: CC(=O)Nc1ncc(CN2CCC(=CC(=O)Nc3ccc(F)cc3)CC2)s1] | 2-(1-((2-acctamidothiazol-5-yl)methyl)piperidin-4-ylidene)-N-(4-fluoro phenyl)acetamide |
| C-3 | 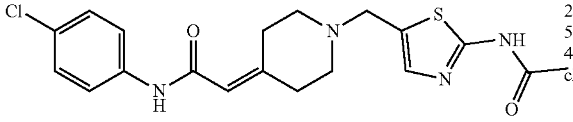 | 2-(1-((2-acetamidothiazol-5-yl)methyl)piperidin-4-ylidene)-N-(4-chlorophenyl)acetamide |
| C-4 | 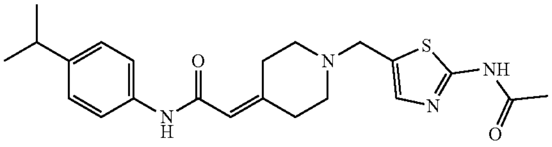 [SMILES: CC(=O)Nc1ncc(CN2CCC(=CC(=O)Nc3ccc(C(C)C)cc3)CC2)s1] | 2-(1-((2-acetamidothiazol-5-yl)methylpiperidin-4-ylidene)-N-(4-isopropylphenyl)acetamide |
| C-5 | 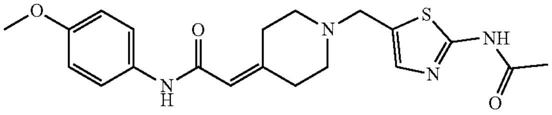 [SMILES: COc1ccc(NC(=O)C=C2CCN(Cc3cnc(NC(C)=O)s3)CC2)cc1] | 2-(1-((2-acetamidothiazol-5-yl)methyl)piperidin-4-ylidene)-N-(4-methoxyphenyl)acetamide |
| C-6 | 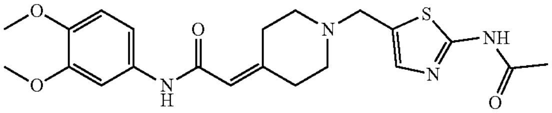 [SMILES: COc1ccc(NC(=O)C=C2CCN(Cc3cnc(NC(C)=O)s3)CC2)cc1OC] | 2-(1-((2-acetamidothiazol-5-yl)methyl)piperidin-4-ylidene)-N-(3,4-dimethoxyphenyl)acetamide |
| C-7 | 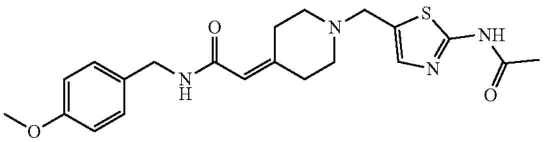 [SMILES: COc1ccc(CNC(=O)C=C2CCN(Cc3cnc(NC(C)=O)s3)CC2)cc1] | 2-(1-((2-acetamidothiazol-5-yl)methyl)piperidin-4-ylidene)-N-(4-methoxybenzyl)acetamide |
| C-8 | 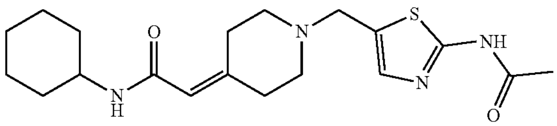 [SMILES: CC(=O)Nc1ncc(CN2CCC(=CC(=O)NC3CCCCC3)CC2)s1] | 2-(1-((2-acetamidothiazol-5-yl)methyl)piperidin-4-ylidene)-N-cyclohexylacetamide |

In an embodiment of the present invention, the compound may have inhibitory activity against O-GlcNAcase, but is not limited thereto.

Further, the present invention provides a pharmaceutical composition for treating or preventing diseases caused by hyperphosphorylation of tau, including the compound according to the present invention or a pharmaceutical salt thereof as an active ingredient.

In an embodiment of the present invention, the disease may include cerebral stroke, stroke, memory loss, memory impairment, dementia, amnesia, Parkinson's disease, Alzheimer's disease, Pick's disease, Creutzfeld-Jakob disease, Huntington's disease, multiple sclerosis, amyotrophic lateral sclerosis (ALS), frontotemporal dementia (FTD), progressive supranuclear palsy (PSAP), corticobasal degeneration (CBD), Lou Gehrig's disease, etc., but is not limited thereto.

In the pharmaceutical composition of the present invention, the compound according to the present invention may be administered in an appropriate formulation together with a carrier and a diluent known in the art, and orally or parenterally administered according to a desired method, and for example, may have formulations such as intravenous injection, intramuscular injection, intraperitoneal injection, subcutaneous injection, and suppositories.

The formulations may be prepared by a general method using suitable excipients, fillers, binders, wetting agents, disintegrants, lubricants, surfactants, dispersants, buffers, preservatives, solubilizers, disinfectants, sweeteners, flavours, analgesics, stabilizers, isotonic solutions, and the like, which have been commonly used in a pharmaceutical composition.

Each of the formulations described above may include a pharmaceutically acceptable carrier or additive. Specific examples of the carrier or additive include water, pharmaceutically acceptable organic solvents, collagen, polyvinyl alcohol, polyvinylpyrrolidine, carboxyvinyl polymer, sodium alginate, water-soluble dextran, carboxymethyl sodium starch, pectin, xanthan rubber, arabic rubber, casein, gelatin, agar, glycerol, propylene glycol, polyethyl glycol, vaseline, paraffin, stearyl alcohol, stearic acid, human serum albumin, mannitol, sorbitol, lactic acid, etc. One or more additives may be selected or appropriately combined depending on a form of the formulation. Furthermore, as a method of administering a cell therapy, local administration to target cells may be performed in addition to conventional systemic administration such as intravenous or intraarterial administration, and an administration method combined with catheter technology and surgical surgery may be used.

The composition of the present invention may include the compound according to the present invention in a pharmaceutically effective dose together with the pharmaceutically acceptable carrier.

In the present invention, the "pharmaceutically effective dose" refers to an amount of an active ingredient that exhibits effects of alleviating, inhibiting, ameliorating and/or treating immune rejection disease to be treated. The dose of the compound according to the present invention varies in the range thereof according to the weight, age, sex, and health condition of a patient, a diet, an administration time, an administration method, the severity of disease, etc. For example, a therapeutically effective dose may be initially determined using in vitro analysis through cell culture. Even without excessive experiments in the art, the therapeutically effective dose may be determined, and a useful dose to the human may be more accurately determined using such information. For example, the compound according to the present invention may be administered as an active ingredient in an amount of 0.1 to 100 mg/kg/day.

Further, the present invention provides a health functional food for improving or preventing diseases caused by hyperphosphorylation of tau, including the compound according to the present invention or a pharmaceutical salt thereof as an active ingredient.

The "food" means natural products or processed products containing one or more nutrients, and preferably, means a condition that may be eaten directly through a certain amount of processing process, and as a general meaning, means including all of foods, food additives, functional foods and beverages.

Foods to which the food composition may be added include, for example, various foods, beverages, gum, tea, vitamin complexes, functional foods, and the like. Additionally, the food includes special nutritional foods (e.g., milk formulas, infant, baby food, etc.), processed meat products, fish products, tofu, jellied food, noodles (e.g., ramen, noodles, etc.), bread, health supplements, seasoned foods (e.g., soy sauce, soybean paste, red pepper paste, mixed soy sauce, etc.), sauces, confectionery (e.g., snacks), candies, chocolates, gums, ice creams, dairy products (e.g., fermented milk, cheese, etc.), other processed foods, kimchi, pickled foods (various types of kimchi, pickles, etc.), beverages (e.g., fruit drinks, vegetable drinks, soybean milk products, fermented drinks, etc.), and natural seasonings (e.g., ramen soup, etc.), but is not limited thereto. The foods, beverages or food additives may be prepared by general preparation methods.

In addition, the "functional food" or "health functional food" refers to a food group that imparts added value to the food to act and express the function of the corresponding food for a specific purpose by using physical, biochemical, and bioengineering techniques, or food that is designed and processed to sufficiently express in vivo body modulating functions for biological defense rhythm control, disease prevention and recovery, etc. of the food composition, and specifically, may be a health functional food. The functional food may include food-acceptable food supplement additives, and may further include suitable carriers, excipients, and diluents which are commonly used in the preparation of functional foods.

The type of health supplement is not limited thereto, but may be in the form of powders, granules, tablets, capsules or beverages.

Further, the present invention provides a method for preventing or treating diseases caused by hyperphosphorylation of tau, including administering to a subject a compound according to the present invention or a pharmaceutical salt thereof, or a pharmaceutical composition including the same.

The subject may be a mammal, for example, a human, but is not limited thereto.

Modes for the Invention

Hereinafter, the present invention will be described in detail by Examples. However, these Examples are only illustrative of the present invention, and the scope of the present invention is not limited to these Examples.

EXAMPLES
Example 1
Preparation of Compound of Chemical Formula 2
A compound of Chemical Formula 2 below was prepared by the following process.
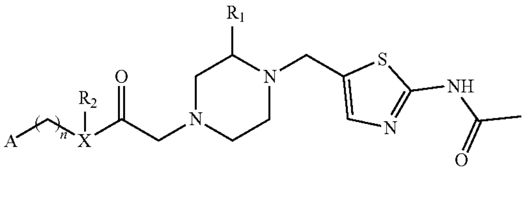
Scheme 1. Synthesis of A-1 to A-41
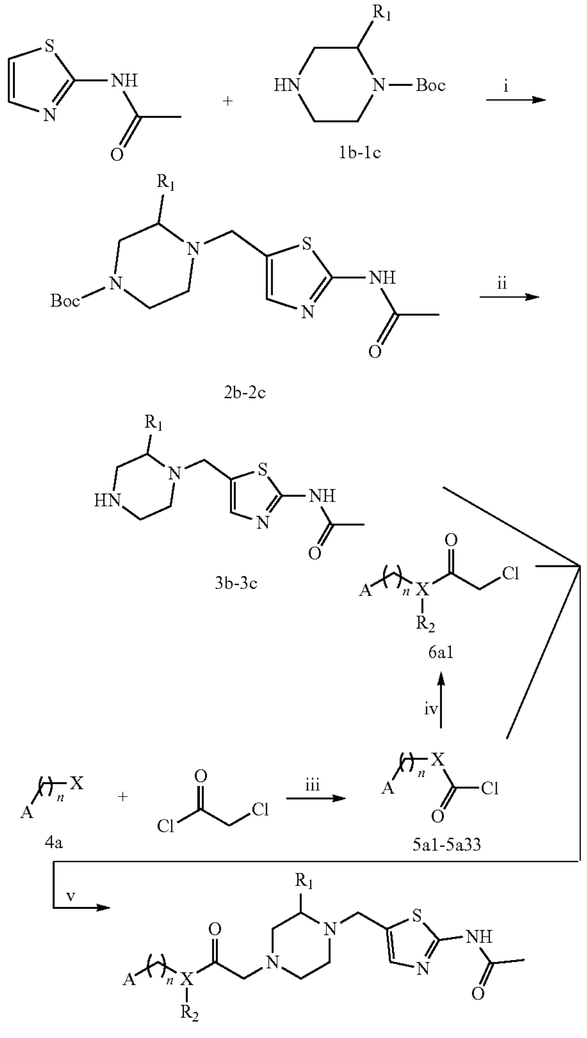
A-1-A-41
A:
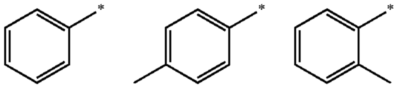
-continued
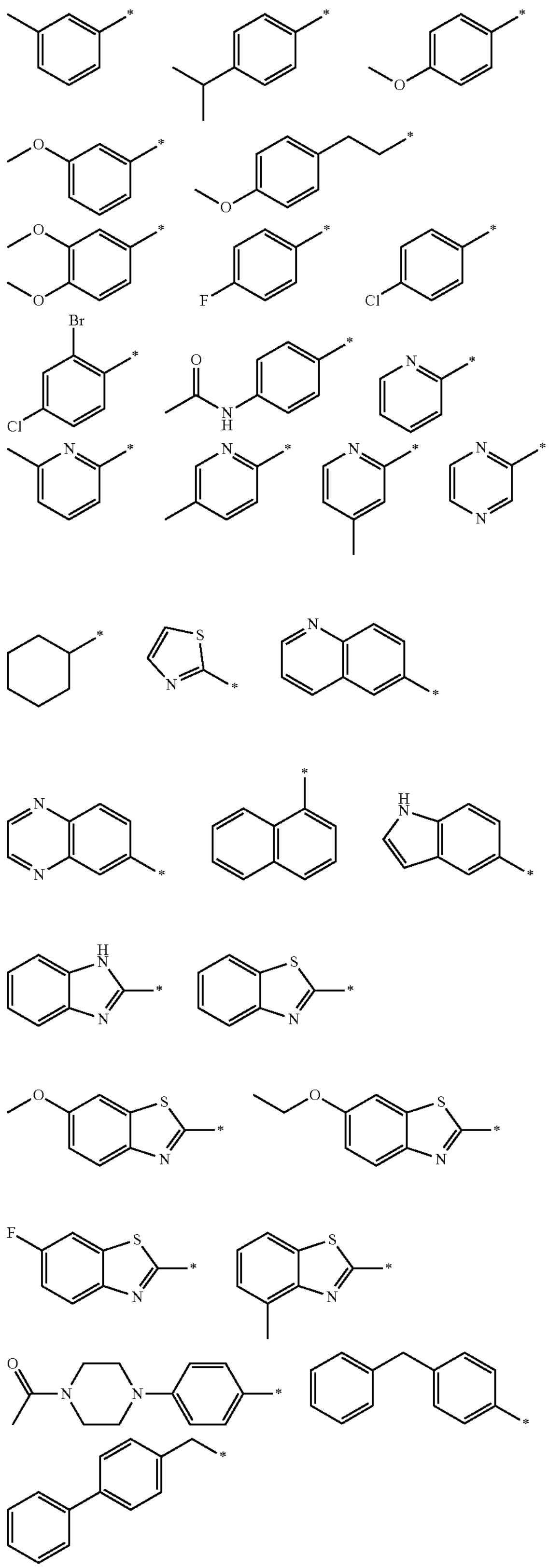
Reagents and conditions: (i) paraformaldehyde, AcOH, 100° C., 4 h, (ii) TFA, DCM, r.t., overnight; (iii) TEA, DCM, 0° C.-r.t., 4 h; (iv) NaH, iodomethane, DMF, 0° C.-r.t., 1 h; (v) Amine compounds, $K_2CO_3$, acetonitrile, r.t., overnight.

Scheme 2. Synthesis of 1c

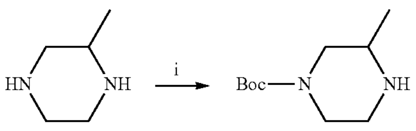

1c

Reagents and conditions: (i) di-tert-butyl dicarbonate, DCM, 0° C.-r.t., 4 h

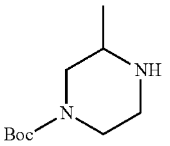

tert-butyl 3-methylpiperazine-1-carboxylate (1c): Di-tert-butyl dicarbonate (761 mg, 3.49 mmol) was added dropwise to a solution of 2-methylpiperazine (349 mg, 3.49 mmol) in DCM (20 mL) at 0° C., and the reaction mixture was stirred at room temperature for 4 hours. DCM was evaporated in vacuum. The resulting residue was purified by column chromatography (DCM:MeOH=20:1) to obtain an intermediate 1c in the form of light yellow oil (166 mg, 83%). $^1$H NMR (400 MHz, $CDCl_3$) δ: 3.93 (s, 2H), 2.98-2.68 (m, 5H), 2.46-2.31 (m, 1H), 1.46 (s, 9H), 1.05 (d, J=6.3 Hz, 3H).

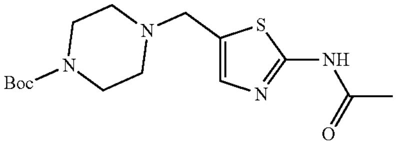 [SMILES: CC(=O)Nc1ncc(CN2CCN(C(=O)OC(C)(C)C)CC2)s1]

tert-butyl 4-((2-acetamidothiazol-5-yl)methyl)piperazine-1-carboxylate (2b): Paraformaldehyde (3.10 g, 104.69 mmol) was added to a stirred solution of 2-acetamidothiazole (5.50 g, 31.74 mmol) and 1-(tert-butoxycarbonyl)piperazine (3.90 g, 21.16 mmol) in acetic acid (50 mL) at 100° C. The reaction mixture was stirred at 100° C. for 4 hours. Acetic acid was evaporated in vacuum. The resulting residue was purified by column chromatography (n-hexane:EtOAc=2:1) to obtain 2b in the form of a light yellow solid (6.65 g, 93%). $^1$H NMR (400 MHz, $CDCl_3$) δ: 11.68 (s, 1H), 7.20 (s, 1H), 3.68 (s, 2H), 3.43 (t, J=5.0 Hz, 4H), 2.43 (t, J=5.0 Hz, 4H), 2.31 (s, 3H), 1.45 (s, 9H).

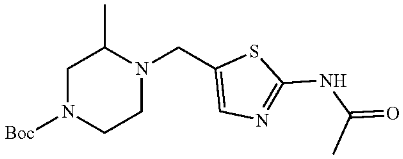 [SMILES: CC(=O)Nc1ncc(CN2CCN(C(=O)OC(C)(C)C)CC2C)s1]

tert-butyl 4-((2-acetamidothiazol-5-yl)methyl)-3-methylpiperazine-1-carboxylate (2c): The same process as the synthesis process of 2b was performed using 2-acetamidothiazole (618 mg, 4.35 mmol), the intermediate 1c (166 mg, 2.90 mmol), and paraformaldehyde (435 mg, 14.50 mmol) in acetic acid (20 mL) and then the reaction mixture was purified by column chromatography (DCM:MeOH=30:1) to obtain an intermediate 2c in the form of a light yellow solid (873 mg, 85%). $^1$H NMR (400 MHz, $CDCl_3$) δ: 7.14 (s, 1H), 3.97 (d, J=14.6 Hz, 1H), 3.67 (dd, J=18.7, 13.8 Hz, 4H), 3.48 (q, J=7.0 Hz, 1H), 3.12 (d, J=10.5 Hz, 1H), 2.70 (dt, J=11.5, 3.7 Hz, 1H), 2.46 (s, 1H), 2.11 (s, 3H), 1.44 (s, 9H), 1.12 (d, J=6.2 Hz, 3H).

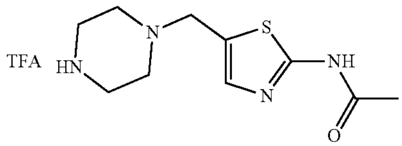 [SMILES: CC(=O)Nc1ncc(CN2CCNCC2)s1]

N-(5-(piperazin-1-ylmethyl)thiazol-2-yl)acetamide compound with 2,2,2-trifluoroacetaldehyde (1:1) (3b): The intermediate 2b was dissolved in DCM (50 mL) and the reaction mixture was stirred overnight at room temperature. DCM was evaporated in vacuum to obtain 3b in the form of a light yellow solid (6.61 g, quantitative yield). $^1$H NMR (400 MHz, DMSO-$d_6$) δ: 12.31 (s, 1H), 9.20 (s, 2H), 7.61 (s, 1H), 4.55 (s, 2H), 2.17 (s, 3H).

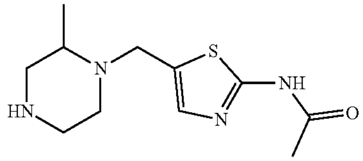 [SMILES: CC(=O)Nc1ncc(CN2CCNCC2C)s1]

N-(5-((2-methylpiperazin-1-yl)methyl)thiazol-2-yl)acetamide (3c): The synthesis method of 3b was performed using the intermediate 2c (873 mg, 2.90 mmol) and TFA (3.32 g, 29.10 mmol) in DCM (20 mL) to obtain an intermediate 3c in the form of a light yellow solid (633 mg, 86%). $^1$H NMR (400 MHz, DMSO-$d_6$) δ: 12.02 (s, 1H), 7.31 (s, 1H), 4.00 (d, J=14.7 Hz, 1H), 3.72 (d, J=14.7 Hz, 1H), 3.15 (dd, J=10.8, 2.5 Hz, 2H), 2.94-2.87 (m, 1H), 2.82 (dt, J=12.8, 3.2 Hz, 1H), 2.71-2.58 (m, 2H), 2.38 (ddd, J=13.0, 11.3, 2.9 Hz, 1H), 2.12 (s, 3H), 1.13 (d, J=6.0 Hz, 3H).

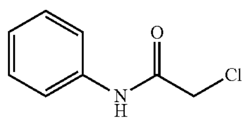 [SMILES: O=C(CCl)Nc1ccccc1]

2-chloro-N-phenylacetamide (5a1): Chloroacetyl chloride (1.33 g, 11.81 mmol) was added dropwise to aniline (1.00 g, 10.74 mmol) and trimethylamine (1.20 g, 11.81 mmol) in DCM (30 mL) at 0° C. and the reaction mixture was stirred at room temperature for 4 hours. DCM was evaporated in vacuum. The resulting residue was purified by column chromatography (n-hexane:EtOAc=2:1) to obtain an intermediate Sal in the form of a light red solid (1.80 g, 99%). $^1$H NMR (400 MHz, $CDCl_3$) δ: 8.22 (s, 1H), 7.58-7.52 (m, 2H), 7.40-7.33 (m, 2H), 7.21-7.15 (m, 1H), 4.20 (s, 2H).

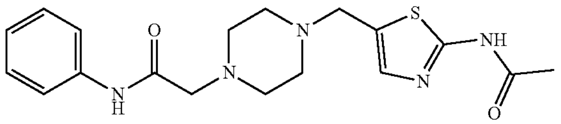 [SMILES: CC(=O)Nc1ncc(CN2CCN(CC(=O)Nc3ccccc3)CC2)s1]

2-(4-((2-acetamidothiazol-5-yl)methyl)piperazin-1-yl)-N-phenylacetamide (A-1): The intermediate 5a1 (79 mg, 0.46 mmol) was added to a suspension of the intermediate 3b (190 mg, 0.55 mmol) and $K_2CO_3$ (152 mg, 1.10 mmol) in acetonitrile (30 mL). The reaction mixture was stirred overnight at room temperature. Acetonitrile was evaporated in vacuum. The resulting residue was purified by column chromatography (DCM:MeOH=20:1) to obtain a white solid A-1 (100 mg, 58%). Mp: 190-192° C. $^1$H NMR (400 MHz, $CDCl_3$) δ: 10.25 (s, 1H), 9.09 (s, 1H), 7.58-7.54 (m, 2H), 7.33 (dd, J=8.5, 7.4 Hz, 2H), 7.14-7.08 (m, 1H), 3.72 (d, J=1.0 Hz, 2H), 3.14 (s, 2H), 2.66 (s, 4H), 2.58 (s, 4H), 2.29 (s, 3H).

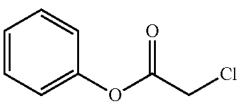 [SMILES: O=C(CCl)Oc1ccccc1]

phenyl 2-chloroacetate (5a2): The synthesis method of 5a1 was performed using phenol (750 mg, 7.97 mmol), triethylamine (887 mg, 0.47 mmol), and chloroacetyl chloride (990 mg, 8.77 mmol) in DCM and then the reaction mixture was purified by column chromatography (n-hexane/EtOAc=1:1) to obtain an intermediate 5a2 in the form of colorless oil (1.03 g, 76%). $^1$H NMR (400 MHz, $CDCl_3$) δ: 7.44-7.37 (m, 2H), 7.30-7.26 (m, 1H), 7.16-7.09 (m, 2H), 4.31 (s, 2H).

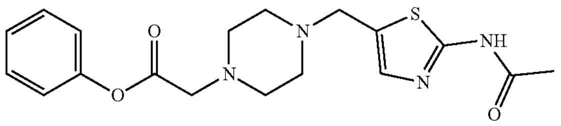 [SMILES: CC(=O)Nc1ncc(CN2CCN(CC(=O)Oc3ccccc3)CC2)s1]

phenyl 2-(4-((2-acetamidothiazol-5-yl)methyl)piperazin-1-yl)acetate (A-2): The synthesis method of the compound A-1 was performed using the intermediate 3b (623 mg, 1.75 mmol), the intermediate 5a2 (200 mg, 1.17 mmol) and $K_2CO_3$ (486 mg, 3.52 mmol) in acetonitrile, and the reaction mixture was purified by column chromatography (DCM: MOH=20:1) to obtain a compound A-2 in the form of a white solid (103 mg, 23%). Mp: 185-194° C. $^1$H NMR (400 MHz, $CDCl_3$) δ: 10.91 (s, 1H), 7.37 (dd, J=8.4, 7.4 Hz, 2H), 7.25-7.22 (m, 1H), 7.21 (s, 1H), 7.11-7.07 (m, 2H), 3.69 (s, 2H), 3.48 (s, 2H), 2.71 (s, 4H), 2.60 (s, 4H), 2.29 (s, 3H).

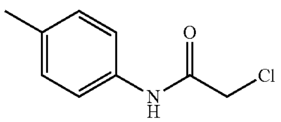

2-chloro-N-(p-tolyl)acetamide (5a3): The synthesis process of Sal was performed using p-toluidine (500 mg, 4.67 mmol), triethylamine (519 mg, 5.13 mmol), and chloroacetyl chloride (579 mg, 5.13 mmol) in DCM and then the reaction mixture was purified by column chromatography (n-hexane/EtOAc=2:1) to obtain an intermediate 5a3 in the form of colorless oil (950 mg, 99%). $^1$H NMR (400 MHz, $CDCl_3$) δ: 8.16 (s, 1H), 7.46-7.38 (m, 2H), 7.18-7.14 (m, 2H), 4.19 (s, 2H), 2.33 (s, 3H).

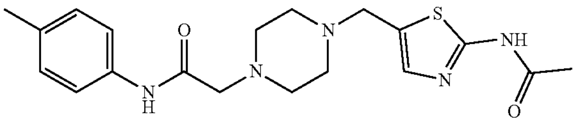 [SMILES: CC(=O)Nc1ncc(CN2CCN(CC(=O)Nc3ccc(C)cc3)CC2)s1]

2-(4-((2-acetamidothiazol-5-yl)methyl)piperazin-1-yl)-N-(p-tolyl)acetamide (A-3): The synthesis method of the compound A-1 was performed using the intermediate 5a3 (200 mg, 1.09 mmol), the intermediate 3b (314 mg, 1.31 mmol), and $K_2CO_3$ (181 mg, 1.31 mmol) in acetonitrile, and the reaction mixture was purified by column chromatography (DCM:MOH=20:1) to obtain a compound A-3 in the form of a white solid (113 mg, 26%). Mp: 213-217° C. $^1$H NMR (400 MHz, $CDCl_3$) δ: 9.82 (s, 1H), 9.00 (s, 1H), 7.43 (d, J=8.5 Hz, 2H), 7.21 (d, J=0.9 Hz, 1H), 7.13 (d, J=8.1 Hz, 2H), 3.71 (d, J=1.0 Hz, 2H), 3.12 (s, 2H), 2.65 (s, 4H), 2.58 (s, 4H), 2.32 (s, 3H), 2.28 (s, 3H).

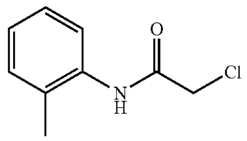

2-chloro-N-(o-tolyl)acetamide (5a4): The synthesis method of Sal was performed using m-toluidine (500 mg, 4.67 mmol), triethylamine (519 mg, 5.13 mmol), and chloroacetyl chloride (579 mg, 5.13 mmol) in DCM and then the reaction mixture was purified by column chromatography (n-hexane/EtOAc=1:1) to obtain an intermediate 5a4 in the form of colorless oil (867 mg, 77%). $^1$H NMR (400 MHz, $CDCl_3$) δ: 8.22 (s, 1H), 7.90-7.86 (m, 1H), 7.26-7.19 (m, 2H), 7.12 (td, J=7.4, 1.3 Hz, 1H), 4.24 (s, 2H), 2.31 (s, 3H).

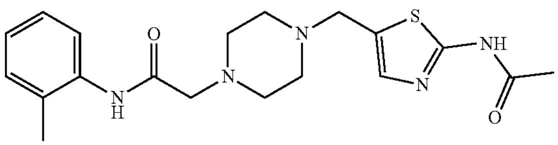 [SMILES: CC(=O)Nc1ncc(CN2CCN(CC(=O)Nc3ccccc3C)CC2)s1]

2-(4-((2-acetamidothiazol-5-yl)methyl)piperazin-1-yl)-N-(o-tolyl)acetamide (A-4): The synthesis method of the compound A-1 was performed using the intermediate 5a4 (296 mg, 1.62 mmol), the intermediate 3b (467 mg, 1.94 mmol), and $K_2CO_3$ (268 mg, 1.94 mmol) in acetonitrile, and the reaction mixture was purified by column chromatography (DCM:MOH=20:1) to obtain a compound A-4 in the form of a light yellow solid (15 mg, 3%). Mp: 194-196° C. $^1$H NMR (400 MHz, $CDCl_3$) δ: 9.24 (s, 1H), 8.93 (s, 1H), 8.12 (dd, J=8.0, 1.2 Hz, 1H), 7.95 (d, J=7.9 Hz, 1H), 7.32 (s, 1H), 7.13 (d, J=7.3 Hz, 1H), 7.06-7.04 (m, 1H), 3.72 (d, J=1.0 Hz, 2H), 3.18 (s, 2H), 2.70 (s, 4H), 2.58 (s, 4H), 2.27 (s, 3H), 2.12 (s, 3H).

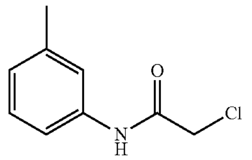

2-chloro-N-(m-tolyl)acetamide (5a5): The synthesis method of 5a1 was performed using m-toluidine (500 mg, 4.67 mmol), triethylamine (519 mg, 5.13 mmol), and chloroacetyl chloride (579 mg, 5.13 mmol) in DCM and then the reaction mixture was purified by column chromatography (n-hexane/EtOAc=5:1) to obtain an intermediate 5a5 in the form of colorless oil (741 mg, 86%). $^1$H NMR (400 MHz, $CDCl_3$) δ: 8.26 (s, 1H), 7.41-7.32 (m, 2H), 7.27 (s, 1H), 6.99 (ddd, J=7.6, 1.9, 1.0 Hz, 1H), 4.20 (s, 2H), 2.36 (s, 3H).

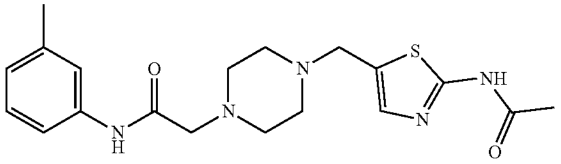 [SMILES: CC(=O)Nc1ncc(CN2CCN(CC(=O)Nc3cccc(C)c3)CC2)s1]

2-(4-((2-acetamidothiazol-5-yl)methyl)piperazin-1-yl)-N-(m-tolyl)acetamide (A-5): The synthesis method of the compound A-1 was performed using the intermediate 5a5 (200 mg, 1.09 mmol), the intermediate 3b (463 mg, 1.31 mmol), and $K_2CO_3$ (434 mg, 1.31 mmol) in acetonitrile, and the reaction mixture was purified by column chromatography (DCM:MOH=20:1) to obtain a compound A-5 in the form of a light yellow solid (259 mg, 61%). Mp: 202-204° C. $^1$H NMR (400 MHz, $CDCl_3$) δ: 11.24 (s, 1H), 9.02 (s, 1H), 7.39 (t, J=1.8 Hz, 1H), 7.35-7.33 (m, 1H), 7.23-7.19 (m, 2H), 6.93 (ddt, J=7.6, 1.9, 0.9 Hz, 1H), 3.72 (d, J=1.0 Hz, 2H), 3.13 (s, 2H), 2.65 (s, 4H), 2.59 (s, 4H), 2.35 (s, 3H), 2.30 (s, 3H).

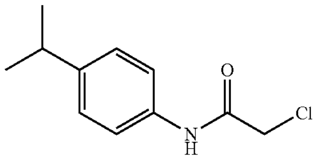

2-chloro-N-(4-isopropylphenyl)acetamide (5a6): The synthesis method of Sal was performed using 4-isopropylaniline (500 mg, 3.70 mmol), triethylamine (411 mg, 4.07 mmol), and chloroacetyl chloride (459 mg, 4.07 mmol) in DCM and then the reaction mixture was purified by column chromatography (n-hexane/EtOAc=1:1) to obtain an intermediate 5a6 in the form of a white solid (741 mg, 95%). $^1$H NMR (400 MHz, $CDCl_3$) δ: 8.17 (s, 1H), 7.48-7.41 (m, 2H), 7.24-7.19 (m, 2H), 4.19 (s, 2H), 2.90 (p, J=6.9 Hz, 1H), 1.25 (s, 3H), 1.23 (s, 3H).

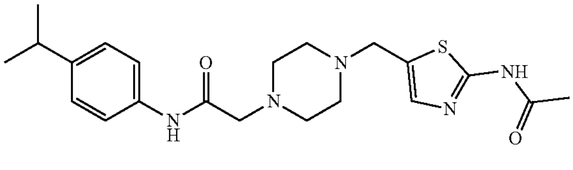 [SMILES: CC(=O)Nc1ncc(CN2CCN(CC(=O)Nc3ccc(C(C)C)cc3)CC2)s1]

2-(44(2-acetamidothiazol-5-yl)methyl)piperazin-1-yl)-N-(4-isopropylphenyl)acetamide (A-6): The synthesis method of the compound A-1 was performed using the intermediate 5a6 (250 mg, 1.18 mmol), the intermediate 3b (340 mg, 1.42 mmol), and $K_2CO_3$ (196 mg, 1.42 mmol) in acetonitrile, and the reaction mixture was purified by column chromatography (DCM:MOH=20:1) to obtain a compound A-6 in the form of a white solid (86 mg, 18%). Mp: 173-176° C. $^1$H NMR (400 MHz, $CDCl_3$) δ: 10.51 (s, 1H), 9.00 (s, 1H), 7.47-7.45 (m, 2H), 7.22 (s, 1H), 7.19 (d, J=8.4 Hz, 2H), 3.72 (s, 2H), 3.13 (s, 2H), 2.88 (p, J=6.9 Hz, 1H), 2.65 (s, 4H), 2.58 (s, 4H), 2.29 (s, 3H), 1.23 (d, J=6.9 Hz, 6H).

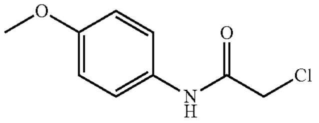

2-chloro-N-(4-methoxyphenyl)acetamide (5a7): The synthesis method of Sal was performed using p-anisidine (500 mg, 406 mmol), triethylamine (452 mg, 4.47 mmol), and chloroacetyl chloride (504 mg, 4.47 mmol) in DCM and then the reaction mixture was purified by column chromatography (n-hexane/EtOAc=1:1) to obtain an intermediate 5a7 in the form of a white solid (802 mg, 99%). $^1$H NMR (400 MHz, $CDCl_3$) δ: 8.26 (s, 1H), 7.48-7.43 (m, 2H), 6.92-6.86 (m, 2H), 4.20 (s, 2H), 3.80 (s, 3H).

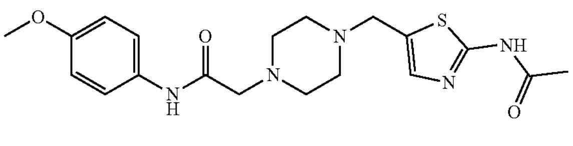 [SMILES: COc1ccc(NC(=O)CN2CCN(Cc3cnc(NC(C)=O)s3)CC2)cc1]

2-(4-((2-acetamidothiazol-5-yl)methyl)piperazin-1-yl)-N-(4-methoxyphenyl)acetamide (A-7): The synthesis method of the compound A-1 was performed using the intermediate 5a7 (200 mg, 1.00 mmol), the intermediate 3b (426 mg, 1.20 mmol), and $K_2CO_3$ (331 mg, 2.40 mmol) in acetonitrile, and the reaction mixture was purified by column chromatography (DCM:MOH=20:1) to obtain a compound A-7 in the form of a light yellow solid (135 mg, 33%). Mp: 217-220° C. $^1$H NMR (400 MHz, $CDCl_3$) δ: 10.82 (s, 1H), 8.95 (s, 1H), 7.47-7.45 (m, 2H), 7.22 (t, J=0.9 Hz, 1H), 6.88-6.86 (m, 2H), 3.79 (s, 3H), 3.71 (d, J=1.0 Hz, 2H), 3.13 (s, 2H), 2.65 (s, 4H), 2.58 (s, 4H), 2.30 (s, 3H).

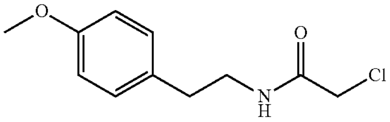

2-chloro-N-(4-methoxyphenethyl)acetamide (5a8): 2-(4-methoxyphenyl)ethylamine (500 mg, 3.30 mmol), triethylamine (367 mg, 3.63 mmol), and chloroacetyl chloride (410 mg, 3.63 mmol) in DCM were used and purified by column chromatography (n-hexane/EtOAc=1:1) to obtain an intermediate 5a8 in the form of light yellow oil (751 mg, 63%). $^1$H NMR (400 MHz, $CDCl_3$) δ: 7.15-7.10 (m, 2H), 6.89-6.84 (m, 2H), 6.58 (s, 1H), 4.02 (s, 2H), 3.80 (s, 3H), 3.53 (td, J=7.0, 5.9 Hz, 2H), 2.79 (t, J=7.0 Hz, 2H).

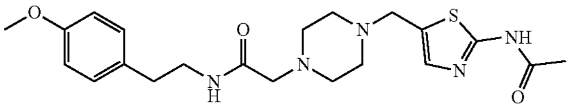 [SMILES: COc1ccc(CCNC(=O)CN2CCN(Cc3cnc(NC(C)=O)s3)CC2)cc1]

2-(44(2-acetamidothiazol-5-yl)methyl)piperazin-1-yl)-N-(4-methoxyphenethyl)acetamide (A-8): The synthesis method of the compound A-1 was performed using the intermediate 5a8 (200 mg, 0.88 mmol), the intermediate 3b (375 mg, 1.06 mmol), and $K_2CO_3$ (166 mg, 1.06 mmol) in acetonitrile, and the reaction mixture was purified by column chromatography (DCM:MOH=30:1) to obtain a compound A-8 in the form of a light yellow solid (117 mg, 31%). Mp: 177-179° C. $^1$H NMR (400 MHz, $CDCl_3$) δ: 11.21 (s, 1H), 7.20 (d, J=1.0 Hz, 1H), 7.13-7.09 (m, 2H), 6.85-6.83 (m, 2H), 3.79 (s, 3H), 3.64 (d, J=1.0 Hz, 2H), 3.52 (q, J=6.6 Hz, 2H), 2.95 (s, 2H), 2.77 (t, J=6.8 Hz, 2H), 2.44 (d, J=4.4 Hz, 4H), 2.39 (s, 4H), 2.30 (s, 3H).

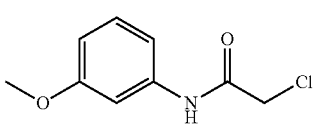

2-chloro-N-(3-methoxyphenyl)acetamide (5a9): The synthesis method of 5a1 was performed using m-anisidine (500 mg, 4.06 mmol), triethylamine (452 mg, 4.47 mmol), and chloroacetyl chloride (504 mg, 4.47 mmol) in DCM and then the reaction mixture was purified by column chromatography (n-hexane/EtOAc=1:1) to obtain an intermediate 5a9 in the form of a white solid (802 mg, 99%). $^1$H NMR (400 MHz, $CDCl_3$) δ: 8.24 (s, 1H), 7.29 (t, J=2.3 Hz, 1H), 7.24 (d, J=8.1 Hz, 1H), 7.04 (ddd, J=8.0, 2.0, 0.9 Hz, 1H), 6.73 (ddd, J=8.3, 2.5, 0.9 Hz, 1H), 4.19 (s, 2H), 3.82 (s, 3H).

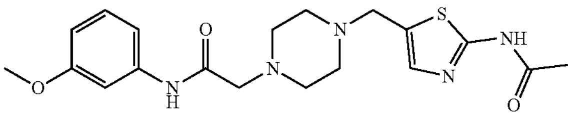 [SMILES: COc1cccc(NC(=O)CN2CCN(Cc3cnc(NC(C)=O)s3)CC2)c1]

2-(44(2-acetamidothiazol-5-yl)methyl)piperazin-1-yl)-N-(3-methoxyphenyl)acetamide (A-9): The synthesis method of the compound A-1 was performed using the intermediate 5a9 (200 mg, 1.00 mmol), the intermediate 3b (426 mg, 1.20 mmol), and $K_2CO_3$ (331 mg, 2.40 mmol) in acetonitrile, and the reaction mixture was purified by column chromatography (DCM:MOH=30:1) to obtain a compound A-9 in the form of a light yellow solid (137 mg, 34%). Mp: 210-212° C. $^1$H NMR (400 MHz, $CDCl_3$) δ: 9.84 (s, 1H), 9.07 (s, 1H), 7.34 (t, J=2.3 Hz, 1H), 7.24-7.20 (m, 2H), 7.02-6.99 (m, 1H), 6.67 (ddd, J=8.3, 2.5, 0.9 Hz, 1H), 3.82 (s, 3H), 3.71 (d, J=0.9 Hz, 2H), 3.13 (s, 2H), 2.65 (s, 4H), 2.58 (s, 4H), 2.28 (s, 3H).

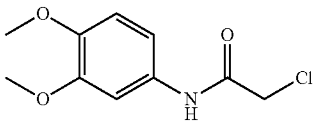

2-chloro-N-(3,4-dimethoxyphenyl)acetamide (5a10): The synthesis method of 5a1 was performed using 3,4-dimethoxyaniline (500 mg, 3.26 mmol), triethylamine (363 mg, 3.59 mmol), and chloroacetyl chloride (405 mg, 3.59 mmol) in DCM and then the reaction mixture was purified by column chromatography (n-hexane/EtOAc=1:1) to obtain an intermediate 5a10 in the form of a white solid (742 mg, 99%). $^1$H NMR (400 MHz, $CDCl_3$) δ: 8.14 (s, 1H), 7.28 (d, J=2.5 Hz, 1H), 6.96 (dd, J=8.6, 2.5 Hz, 1H), 6.84 (d, J=8.6 Hz, 1H), 4.19 (s, 2H), 3.90 (s, 3H), 3.88 (s, 3H).

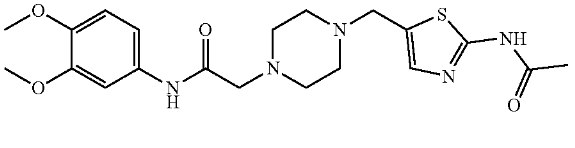 [SMILES: COc1ccc(NC(=O)CN2CCN(Cc3cnc(NC(C)=O)s3)CC2)cc1OC]

2-(4-((2-acetamidothiazol-5-yl)methyl)piperazin-1-yl)-N-(3,4-dimethoxyphenyl)acetamide (A-10): The synthesis method of the compound A-1 was performed using the intermediate 5a11 (280 mg, 1.22 mmol), the intermediate 3b (518 mg, 1.46 mmol), and $K_2CO_3$ (404 mg, 2.93 mmol) in acetonitrile, and the reaction mixture was purified by column chromatography (DCM:MOH=40:1) to obtain a compound A-10 in the form of a light yellow solid (172 mg, 32%). Mp: 182-184° C. $^1$H NMR (400 MHz, $CDCl_3$) δ: 9.75 (s, 1H), 8.96 (s, 1H), 7.42 (d, J=2.4 Hz, 1H), 7.21 (d, J=2.7 Hz, 1H), 6.87 (dd, J=8.6, 2.4 Hz, 1H), 6.81 (d, J=8.6 Hz, 1H), 3.90 (s, 3H), 3.86 (s, 3H), 3.72 (s, 2H), 3.13 (s, 2H), 2.66 (s, 4H), 2.58 (s, 4H), 2.28 (s, 3H).

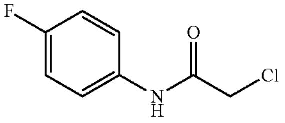 [SMILES: O=C(CCl)Nc1ccc(F)cc1]

2-chloro-N-(4-fluorophenyl)acetamide (5a11): The synthesis method of Sal was performed using 4-fluoroaniline (500 mg, 4.50 mmol), triethylamine (500 mg, 4.95 mmol), and chloroacetyl chloride (559 mg, 4.95 mmol) in DCM and then the reaction mixture was purified by column chromatography (n-hexane/EtOAc=1:1) to obtain an intermediate 5a11 in the form of a light yellow solid (835 mg, 99%). $^1$H NMR (400 MHz, $CDCl_3$) δ: 8.22 (s, 1H), 7.55-7.46 (m, 2H), 7.11-7.00 (m, 2H), 4.20 (s, 2H).

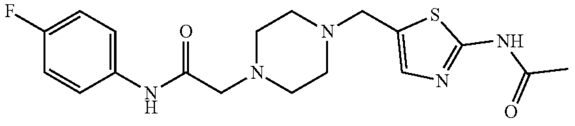 [SMILES: CC(=O)Nc1ncc(CN2CCN(CC(=O)Nc3ccc(F)cc3)CC2)s1]

2-(44(2-acetamidothiazol-5-yl)methyl)piperazin-1-yl)-N-(4-fluorophenyl)acetamide (A-11): The synthesis method of the compound A-1 was performed using the intermediate 5a11 (400 mg, 2.13 mmol), the intermediate 3b (907 mg, 2.56 mmol), and $K_2CO_3$ (353 mg, 2.56 mmol) in acetonitrile, and the reaction mixture was purified by column chromatography (DCM:MOH=40:1) to obtain a compound A-11 in the form of a light yellow solid (145 mg, 17%). Mp: 212-215° C. $^1$H NMR (400 MHz, $CDCl_3$) δ: 10.56 (s, 1H), 9.06 (s, 1H), 7.54-7.50 (m, 2H), 7.22 (s, 1H), 7.00-7.00 (m, 2H), 3.72 (d, J=1.0 Hz, 2H), 3.14 (s, 2H), 2.65 (d, J=4.7 Hz, 4H), 2.58 (s, 4H), 2.29 (s, 3H).

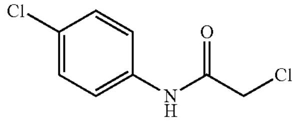 [SMILES: O=C(CCl)Nc1ccc(Cl)cc1]

2-chloro-N-(4-chlorophenyl)acetamide (5a12): The synthesis method of Sal was performed using 4-chloroaniline (552 mg, 4.33 mmol), triethylamine (481 mg, 4.76 mmol), and chloroacetyl chloride (537 mg, 4.76 mmol) in DCM and then the reaction mixture was purified by column chromatography (n-hexane/EtOAc=1:1) to obtain an intermediate 5a12 in the form of a light yellow solid (727 mg, 82%). $^1$H NMR (400 MHz, $CDCl_3$) δ: 8.22 (s, 1H), 7.55-7.46 (m, 2H), 7.37-7.29 (m, 2H), 4.19 (s, 2H).

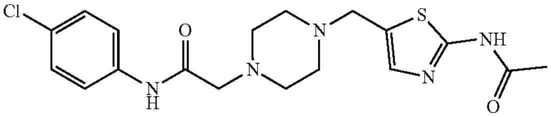 [SMILES: CC(=O)Nc1ncc(CN2CCN(CC(=O)Nc3ccc(Cl)cc3)CC2)s1]

2-(44(2-acetamidothiazol-5-yl)methyl)piperazin-1-yl)-N-(4-chlorophenyl)acetamide (A-12): The synthesis method of the compound A-1 was performed using the intermediate 5a12 (230 mg, 1.13 mmol), the intermediate 3b (478 mg, 1.35 mmol), and $K_2CO_3$ (374 mg, 2.71 mmol) in acetonitrile, and the reaction mixture was purified by column chromatography (DCM:MOH=40:1) to obtain a compound A-12 in the form of a light yellow solid (97 mg, 24%). Mp: 232-236° C. $^1$H NMR (400 MHz, $CDCl_3$) δ: 10.02 (s, 1H), 9.11 (s, 1H), 7.53-7.50 (m, 2H), 7.31-7.27 (m, 2H), 7.22 (s, 1H), 3.72 (d, J=1.0 Hz, 2H), 3.13 (s, 2H), 2.65 (d, J=4.6 Hz, 4H), 2.58 (s, 4H), 2.28 (s, 3H).

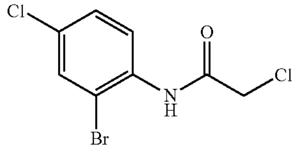 [SMILES: O=C(CCl)Nc1ccc(Cl)cc1Br]

N-(2-bromo-4-chlorophenyl)-2-chloroacetamide (5a13): The synthesis method of Sal was performed using 2-bromo-4-chloroaniline (500 mg, 2.42 mmol), triethylamine (269 mg, 2.66 mmol), and chloroacetyl chloride (300 mg, 2.66 mmol) in DCM and then the reaction mixture was purified by column chromatography (n-hexane/EtOAc=1:1) to obtain an intermediate 5a13 in the form of a light yellow solid (684 mg, 82%). $^1$H NMR (400 MHz, Chloroform-d) δ 8.90 (s, 1H), 8.33 (d, J=8.9 Hz, 1H), 7.58 (d, J=2.3 Hz, 1H), 7.33 (ddd, J=8.9, 2.3, 0.5 Hz, 1H), 4.23 (s, 2H).

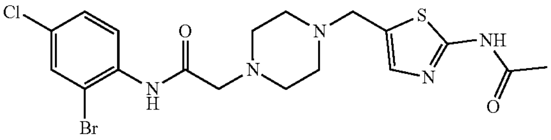 [SMILES: CC(=O)Nc1ncc(CN2CCN(CC(=O)Nc3ccc(Cl)cc3Br)CC2)s1]

2-(4-((2-acetamidothiazol-5-yl)methyl)piperazin-1-yl)-N-(2-bromo-4-chlorophenyl)acetamide (A-13): The synthesis method of the compound A-1 was performed using the intermediate 5a13 (200 mg, 0.71 mmol), the intermediate 3b (298 mg, 0.85 mmol), and $K_2CO_3$ (117 mg, 0.85 mmol) in acetonitrile, and the reaction mixture was purified by column chromatography (DCM:MOH=40:1) to obtain a compound A-13 in the form of a light yellow solid (110 mg, 32%). Mp: 212-213° C. $^1$H NMR (400 MHz, $CDCl_3$) δ: 11.25 (s, 1H), 9.94 (s, 1H), 8.44 (d, J=8.8 Hz, 1H), 7.53 (d, J=2.3 Hz, 1H), 7.29 (dd, J=8.9, 2.4 Hz, 1H), 7.22 (s, 1H), 3.72 (d, J=0.9 Hz, 2H), 3.18 (s, 2H), 2.69 (s, 4H), 2.63 (s, 4H), 2.31 (s, 3H).

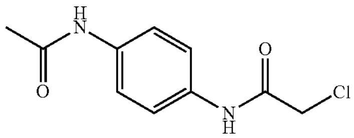

N-(4-acetamidophenyl)-2-chloroacetamide (5a14): The synthesis method of 5a1 was performed using 4'-aminoacetanilide (500 mg, 3.33 mmol), triethylamine (370 mg, 3.66 mmol), and chloroacetyl chloride (413 mg, 3.66 mmol) in DCM and then the reaction mixture was purified by column chromatography (n-hexane/EtOAc=1:1) to obtain an intermediate 5a14 in the form of a white solid (747 mg, 99%). $^1$H NMR (400 MHz, DMSO-d 6) δ: 10.24 (s, 1H), 9.92 (s, 1H), 7.54-7.47 (m, 4H), 4.22 (s, 2H), 2.02 (d, J=2.6 Hz, 3H).

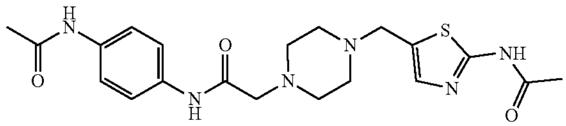 [SMILES: CC(=O)Nc1ccc(NC(=O)CN2CCN(Cc3cnc(NC(C)=O)s3)CC2)cc1]

N-(4-acetamidophenyl)-2-(4-((2-acetamidothiazol-5-yl) methyl)piperazin-1-yl)acetamide (A-14): The synthesis method of the compound A-1 was performed using the intermediate 5a14 (227 mg, 1.00 mmol), the intermediate 3b (425 mg, 1.20 mmol), and $K_2CO_3$ (231 mg, 2.40 mmol) in acetonitrile, and the reaction mixture was purified by column chromatography (DCM:MOH=50:1) to obtain a compound A-14 in the form of a white solid (207 mg, 48%). Mp: 234-237° C. $^1$H NMR (400 MHz, DMSO-$d_6$) δ: 11.93 (s, 1H), 9.85 (s, 1H), 9.57 (s, 1H), 7.52-7.47 (m, 4H), 7.25 (d, J=0.8 Hz, 1H), 3.63 (s, 2H), 3.08 (s, 2H), 2.46 (s, 4H), 2.11 (s, 3H), 2.01 (s, 3H). $^{13}$C NMR (101 MHz, DMSO-$d_6$) δ: 206.98, 168.36, 136.15, 135.45, 134.26, 120.31, 119.73, 65.40, 62.15, 55.36, 53.96, 53.23, 52.53, 49.07, 31.14, 24.33, 22.88, 15.63.

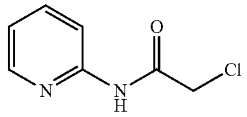 [SMILES: O=C(CCl)Nc1ccccn1]

2-chloro-N-(pyridin-2-yl)acetamide (5a15): The synthesis method of Sal was performed using 2-aminopyridine (500 mg, 5.31 mmol), triethylamine (591 mg, 5.84 mmol), and chloroacetyl chloride (660 mg, 5.84 mmol) in DCM and then the reaction mixture was purified by column chromatography (n-hexane/EtOAc=1:1) to obtain an intermediate 5a15 in the form of a white solid (475 mg, 52%). $^1$H NMR (400 MHz, $CDCl_3$) δ: 8.84 (s, 1H), 8.32 (ddd, J=4.9, 1.9, 1.0 Hz, 1H), 8.20 (d, J=8.4 Hz, 1H), 7.74 (ddd, J=8.3, 7.3, 1.9 Hz, 1H), 7.11 (ddd, J=7.4, 4.9, 1.0 Hz, 1H), 4.20 (s, 2H).

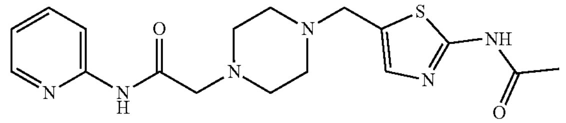

2-(44(2-acetamidothiazol-5-yl)methyl)piperazin-1-yl)-N-(pyridin-2-yl)acetamide (A-15): The synthesis method of the compound A-1 was performed and then the intermediate 5a15 (200 mg, 1.17 mmol), the intermediate 3b (623 mg, 1.75 mmol), and $K_2CO_3$ (486 mg, 3.52 mmol) in acetonitrile were purified by column chromatography (DCM:MOH=30:1) to obtain a compound A-15 in the form of a white solid (78 mg, 18%). Mp: 211-217° C. $^1$H NMR (400 MHz, $CDCl_3$) δ: 11.17 (s, 1H), 9.54 (s, 1H), 8.30 (ddd, J=5.0, 1.9, 0.9 Hz, 1H), 8.24 (dt, J=8.4, 1.1 Hz, 1H), 7.70 (ddd, J=8.6, 7.2, 1.9 Hz, 1H), 7.21 (s, 1H), 7.04 (ddd, J=7.3, 4.9, 1.1 Hz, 1H), 3.71 (d, J=1.0 Hz, 2H), 3.17 (s, 2H), 2.65 (s, 4H), 2.61 (s, 4H), 2.30 (s, 3H).

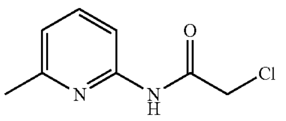

2-chloro-N-(6-methylpyridin-2-yl)acetamide (5a16): The synthesis method of Sal was performed and then 2-amino-6-methylpyridine (500 mg, 4.62 mmol), triethylamine (514 mg, 5.09 mmol), and chloroacetyl chloride (574 mg, 5.13 mmol) in DCM were purified by column chromatography (n-hexane/EtOAc=1:1) to obtain an intermediate 5a16 in the form of a white solid (853 mg, 91%). $^1$H NMR (400 MHz, $CDCl_3$) δ: 8.94 (s, 1H), 8.00 (d, J=8.2 Hz, 1H), 7.63 (dd, J=8.2, 7.5 Hz, 1H), 6.96 (d, J=7.5 Hz, 1H), 4.19 (s, 2H), 2.48 (s, 3H).

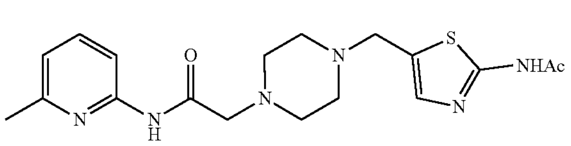 [SMILES: CC(=O)Nc1ncc(CN2CCN(CC(=O)Nc3cccc(C)n3)CC2)s1]

2-(44(2-acetamidothiazol-5-yl)methyl)piperazin-1-yl)-N-(6-methylpyridin-2-yl)acetamide (A-16): The synthesis method of the compound A-1 was performed using the intermediate 5a16 (200 mg, 1.08 mmol), the intermediate 3b (460 mg, 1.30 mmol), and $K_2CO_3$ (180 mg, 1.30 mmol) in acetonitrile, and the reaction mixture was purified by column chromatography (DCM:MOH=20:1) to obtain a compound A-16 in the form of a light yellow solid (134 mg, 32%). Mp: 224-228° C. $^1$H NMR (400 MHz, $CDCl_3$) δ: 10.91 (s, 1H), 9.37 (s, 1H), 8.03 (d, J=8.3 Hz, 1H), 7.58 (t, J=7.9 Hz, 1H), 7.22 (s, 1H), 6.89 (d, J=7.4 Hz, 1H), 3.71 (d, J=1.0 Hz, 2H), 3.15 (s, 2H), 2.63 (s, 8H), 2.47 (s, 3H), 2.30 (s, 3H).

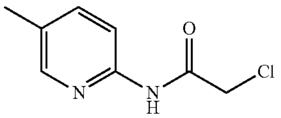

2-chloro-N-(5-methylpyridin-2-yl)acetamide (5a17): The synthesis method of Sal was performed using 2-amino-5-methylpyridine (500 mg, 4.62 mmol), triethylamine (514 mg, 5.09 mmol), and chloroacetyl chloride (574 mg, 5.13 mmol) in DCM and then the reaction mixture was purified by column chromatography (n-hexane/EtOAc=1:1) to obtain an intermediate 5a17 in the form of a white solid (852 mg, 91%). $^1$H NMR (400 MHz, $CDCl_3$) δ: 9.32 (s, 1H), 8.18-8.07 (m, 2H), 7.59 (ddq, J=8.5, 2.2, 0.7 Hz, 1H), 4.19 (s, 2H), 2.33 (d, J=0.8 Hz, 3H).

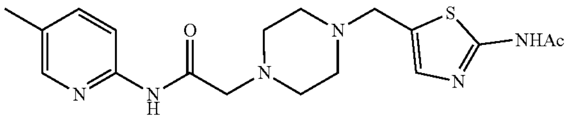 [SMILES: CC(=O)Nc1ncc(CN2CCN(CC(=O)Nc3ccc(C)cn3)CC2)s1]

2-(44(2-acetamidothiazol-5-yl)methyl)piperazin-1-yl)-N-(5-methylpyridin-2-yl)acetamide (A-17): The synthesis method of the compound A-1 was performed using the intermediate 5a17 (200 mg, 1.08 mmol), the intermediate 3b (460 mg, 1.30 mmol), and $K_2CO_3$ (180 mg, 1.30 mmol) in acetonitrile, and the reaction mixture was purified by column chromatography (DCM:MOH=20:1) to obtain a compound A-17 in the form of a light yellow solid (100 mg, 24%). Mp: 224-230° C. $^1$H NMR (400 MHz, $CDCl_3$) δ: 11.45 (s, 1H), 9.46 (s, 1H), 8.13 (d, J=8.4 Hz, 1H), 8.11 (d, J=2.3 Hz, 1H), 7.51 (dd, J=8.5, 2.4 Hz, 1H), 7.21 (d, J=1.1 Hz, 1H), 3.70 (d, J=0.9 Hz, 2H), 3.15 (s, 2H), 2.64 (s, 4H), 2.60 (s, 4H), 2.31 (s, 3H), 2.29 (s, 3H).

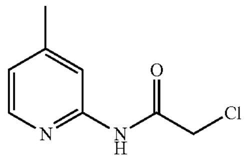

2-chloro-N-(4-methylpyridin-2-yl)acetamide (5a18): The synthesis method of Sal was performed using 2-amino-4-methylpyridine (500 mg, 4.62 mmol), triethylamine (514 mg, 5.09 mmol), and chloroacetyl chloride (574 mg, 5.13 mmol) in DCM and then the reaction mixture was purified by column chromatography (n-hexane/EtOAc=1:1) to obtain an intermediate 5a18 in the form of a white solid (725 mg, 85%). $^1$H NMR (400 MHz, $CDCl_3$) δ: 8.86 (s, 1H), 8.17 (dd, J=5.1, 0.8 Hz, 1H), 8.04 (s, 1H), 6.93 (ddd, J=5.2, 1.6, 0.8 Hz, 1H), 4.19 (s, 2H), 2.39 (d, J=Hz, 3H).

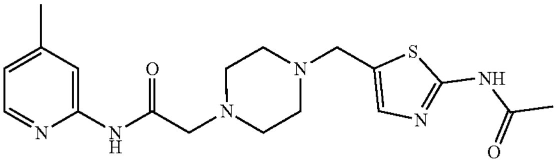 [SMILES: CC(=O)Nc1ncc(CN2CCN(CC(=O)Nc3cc(C)ccn3)CC2)s1]

2-(44(2-acetamidothiazol-5-yl)methyl)piperazin-1-yl)-N-(4-methylpyridin-2-yl)acetamide (A-18): The synthesis method of the compound A-1 was performed using the intermediate 5a18 (200 mg, 1.08 mmol), the intermediate 3b (460 mg, 1.30 mmol), and $K_2CO_3$ (180 mg, 1.30 mmol) in acetonitrile, and the reaction mixture was purified by column chromatography (DCM:MOH=10:1) to obtain a compound A-18 in the form of a light yellow solid (73 mg, 20%). Mp: 210-211° C. $^1$H NMR (400 MHz, $CDCl_3$) δ: 10.22 (s, 1H), 9.48 (s, 1H), 8.15 (dd, J=5.1, 0.8 Hz, 1H), 8.08 (dt, J=1.6, 0.8 Hz, 1H), 7.21 (s, 1H), 6.87 (ddd, J=5.1, 1.5, 0.7 Hz, 1H), 3.70 (d, J=1.0 Hz, 2H), 3.15 (s, 2H), 2.64 (s, 4H), 2.60 (s, 4H), 2.36 (d, J=0.7 Hz, 3H), 2.28 (s, 3H).

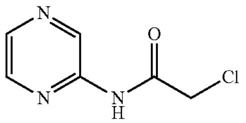 [SMILES: O=C(CCl)Nc1cnccn1]

2-chloro-N-(pyrazin-2-yl)acetamide (5a19): The synthesis method of Sal was performed using 2-aminopyrazine (500 mg, 5.26 mmol), triethylamine (585 mg, 5.78 mmol), and chloroacetyl chloride (664 mg, 5.78 mmol) in DCM and then the reaction mixture was purified by column chromatography (n-hexane/EtOAc=1:1) to obtain an intermediate 5a19 in the form of a white solid (476 mg, 53%). $^1$H NMR (400 MHz, $CDCl_3$) δ: 9.54 (d, J=1.5 Hz, 1H), 8.76 (s, 1H), 8.43 (d, J=2.6 Hz, 1H), 8.31 (dd, J=2.6, 1.6 Hz, 1H), 4.24 (s, 2H).

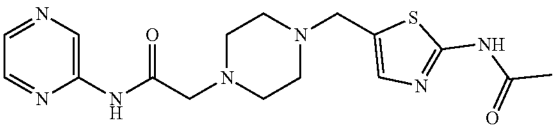 [SMILES: CC(=O)Nc1ncc(CN2CCN(CC(=O)Nc3cnccn3)CC2)s1]

2-(4-((2-acetamidothiazol-5-yl)methyl)piperazin-1-yl)-N-(pyrazin-2-yl)acetamide (A-19): The synthesis method of the compound A-1 was performed using the intermediate 5a19 (257 mg, 1.50 mmol), the intermediate 3b (350 mg, 1.00 mmol), and $K_2CO_3$ (276 mg, 2.00 mmol) in acetonitrile, and the reaction mixture was purified by column chromatography (DCM:MOH=10:1) to obtain a compound A-19 in the form of a white solid (74 mg, 15%). Mp: 224-226° C. $^1$H NMR (400 MHz, $CDCl_3$) δ: 10.24 (s, 1H), 9.58 (s, 1H), 9.57 (d, J=1.5 Hz, 1H), 8.34 (d, J=2.6 Hz, 1H), 8.26 (dd, J=2.6, 1.5 Hz, 1H), 7.21 (s, 1H), 3.71 (d, J=1.0 Hz, 2H), 3.20 (s, 2H), 2.67 (s, 4H), 2.61 (s, 4H), 2.29 (s, 3H).

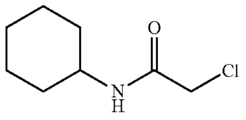 [SMILES: O=C(CCl)NC1CCCCC1]

2-chloro-N-cyclohexylacetamide (5a20): The synthesis method of Sal was performed using cyclohexylamine (500 mg, 5.00 mmol), triethylamine (561 mg, 5.55 mmol), and chloroacetyl chloride (626 mg, 5.55 mmol) in DCM and then the reaction mixture was purified by column chromatography (n-hexane/EtOAc=2:1) to obtain an intermediate 5a20 in the form of oil (225 mg, 45%). $^1$H NMR (400 MHz, $CDCl_3$) δ: 6.43 (s, 1H), 4.03 (d, J=2.8 Hz, 2H), 3.79 (tdt, J=10.6, 8.1, 3.8 Hz, 1H), 1.93 (dd, J=12.8, 3.8 Hz, 2H), 1.73 (dt, J=13.2, 3.9 Hz, 4H), 1.64 (dd, J=12.6, 3.7 Hz, 2H), 1.23-1.18 (m, 2H).

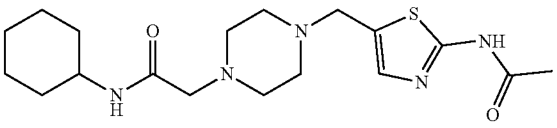 [SMILES: CC(=O)Nc1ncc(CN2CCN(CC(=O)NC3CCCCC3)CC2)s1]

2-(4-((2-acetamidothiazol-5-yl)methyl)piperazin-1-yl)-N-cyclohexylacetamide (A-20): The synthesis method of the compound A-1 was performed using the intermediate 5a20 (225 mg, 2.27 mmol), the intermediate 3b (1.20 g, 3.41 mmol), and $K_2CO_3$ (1.41 g, 10.24 mmol) in acetonitrile, and the reaction mixture was purified by column chromatography (DCM:MOH=40:1) to obtain a compound A-20 in the form of a white solid (74 mg, 15%). Mp: 198-200° C. $^1$H NMR (400 MHz, $CDCl_3$) δ: 10.25 (s, 1H), 7.20 (s, 1H), 7.02 (s, 1H), 3.83-3.78 (m, 1H), 3.69 (d, J=1.0 Hz, 2H), 2.97 (s, 2H), 2.54 (s, 8H), 2.28 (s, 3H), 1.87 (dd, J=12.9, 4.0 Hz, 2H), 1.70-1.67 (m, 2H), 1.41-1.34 (m, 2H), 1.16 (dd, J=12.1, 8.9 Hz, 4H).

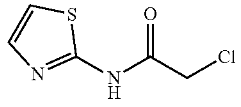

2-chloro-N-(thiazol-2-yl)acetamide (5a21): The synthesis method of 5a1 was performed using 2-aminothiazole (500 mg, 4.99 mmol), triethylamine (559 mg, 5.49 mmol), and chloroacetyl chloride (620 mg, 5.49 mmol) in DCM and then the reaction mixture was purified by column chromatography (n-hexane/EtOAc=2:1) to obtain an intermediate 5a21 in the form of a white solid (562 mg, 64%). $^1$H NMR (400 MHz, $CDCl_3$) δ: 10.06 (s, 1H), 7.51 (d, J=3.5 Hz, 1H), 7.05 (d, J=3.5 Hz, 1H), 4.29 (s, 2H).

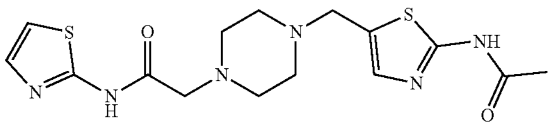 [SMILES: CC(=O)Nc1ncc(CN2CCN(CC(=O)Nc3nccs3)CC2)s1]

2-(4-((2-acetamidothiazol-5-yl)methyl)piperazin-1-yl)-N-(thiazol-2-yl)acetamide (A-21): The synthesis method of the compound A-1 was performed using the intermediate 5a21 (200 mg, 1.13 mmol), the intermediate 3b (661 mg, 1.69 mmol), and $K_2CO_3$ (469 mg, 3.40 mmol) in acetonitrile, and the reaction mixture was purified by column chromatography (DCM:MOH=40:1) to obtain a compound A-21 in the form of a white solid (156 mg, 41%). Mp: 237-240° C. $^1$H NMR (400 MHz, $CDCl_3$) δ: 11.02 (s, 1H), 10.37 (s, 1H), 7.45 (d, J=3.5 Hz, 1H), 7.22 (s, 1H), 6.99 (d, J=3.5 Hz, 1H), 3.71 (d, J=1.0 Hz, 2H), 3.26 (s, 2H), 2.66 (s, 4H), 2.59 (s, 4H), 2.31 (s, 3H).

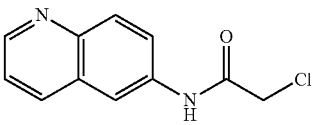 [SMILES: O=C(CCl)Nc1ccc2ncccc2c1]

2-chloro-N-(quinolin-6-yl)acetamide (5a22): The synthesis method of 5a1 was performed using 6-aminoquinoline (500 mg, 3.47 mmol), triethylamine (385 mg, 3.81 mmol), chloroacetyl chloride (430 mg, 3.81 mmol), and DCM and then the reaction mixture was purified by column chromatography (DCM/MeOH=20:1) to obtain a compound 5a22 in the form of a red solid (193 mg, 64%). $^1H$ NMR (400 MHz, $CDCl_3$) δ: 8.88 (d, J=3.9 Hz, 1H), 8.45 (s, 1H), 8.35 (d, J=2.4 Hz, 1H), 8.18-8.07 (m, 2H), 7.65 (dd, J=9.0, 2.4 Hz, 1H), 7.42 (dd, J=8.3, 4.2 Hz, 1H), 4.27 (s, 2H).

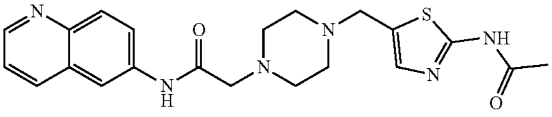 [SMILES: CC(=O)Nc1ncc(CN2CCN(CC(=O)Nc3ccc4ncccc4c3)CC2)s1]

2-(4-((2-acetamidothiazol-5-yl)methyl)piperazin-1-yl)-N-(quinolin-6-yl)acetamide (A-22): The synthesis method of the compound A-1 was performed using the intermediate 5a22 (200 mg, 0.91 mmol), the intermediate 3b (480 mg, 1.36 mmol), and $K_2CO_3$ (187 mg, 1.36 mmol) in acetonitrile, and the reaction mixture was purified by column chromatography (DCM:MOH=40:1) to obtain a compound A-22 in the form of a white solid (155 mg, 40%). Mp: 248-250° C. $^1H$ NMR (400 MHz, $CDCl_3$) δ: 10.79 (s, 1H), 9.36 (s, 1H), 8.83 (dd, J=4.2, 1.7 Hz, 1H), 8.41 (d, J=2.4 Hz, 1H), 8.14 (dd, J=8.0, 1.2 Hz, 1H), 8.06 (d, J=9.0 Hz, 1H), 7.59 (dd, J=9.0, 2.4 Hz, 1H), 7.39 (dd, J=8.3, 4.2 Hz, 1H), 7.24 (s, 1H), 3.75 (d, J=1.0 Hz, 2H), 3.21 (s, 2H), 2.70 (s, 4H), 2.63 (s, 4H), 2.30 (s, 3H).

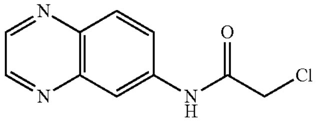 [SMILES: O=C(CCl)Nc1ccc2nccnc2c1]

2-chloro-N-(quinoxalin-6-yl)acetamide (5a23): The synthesis method of the compound A-1 was performed using 6-aminoquinoxaline (500 mg, 3.44 mmol), triethylamine (385 mg, 3.79 mmol), and chloroacetyl chloride (427 mg, 3.79 mmol) in DCM and then the reaction mixture was purified by column chromatography (DCM/MeOH=20:1) to obtain a compound 5a23 in the form of a brown solid (629 mg, 88%). $^1H$ NMR (400 MHz, $CDCl_3$) δ: 8.41 (d, J=2.4 Hz, 1H), 8.12 (d, J=9.1 Hz, 1H), 7.96 (dd, J=9.1, 2.4 Hz, 1H), 7.89 (d, J=8.9 Hz, 1H), 7.23-7.12 (m, 2H), 4.28 (s, 2H).

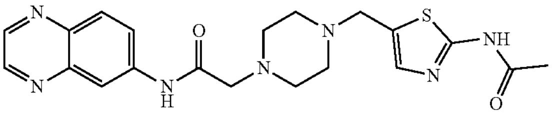 [SMILES: CC(=O)Nc1ncc(CN2CCN(CC(=O)Nc3ccc4nccnc4c3)CC2)s1]

2-(4-((2-acetamidothiazol-5-yl)methyl)piperazin-1 yl)-N-(quinoxalin-6-yl)acetamide (A-23): The synthesis method of the compound A-1 was performed using the intermediate 5a23 (222 mg, 1.00 mmol), the intermediate 3b (425 mg, 1.20 mmol), and $K_2CO_3$ (331 mg, 2.40 mmol) in acetonitrile, and the reaction mixture was purified by column chromatography (DCM:MOH=30:1) to obtain a compound A-23 in the form of a white solid (272 mg, 64%). Mp: 234-235° C. $^1H$ NMR (400 MHz, $CDCl_3$) δ: 10.60 (s, 1H), 9.52 (s, 1H), 8.81 (d, J=1.8 Hz, 1H), 8.76 (d, J=1.9 Hz, 1H), 8.30 (dd, J=2.0, 0.9 Hz, 1H), 8.07-8.06 (m, 2H), 7.24 (s, 1H), 3.75 (d, J=1.0 Hz, 2H), 3.22 (s, 2H), 2.71 (s, 4H), 2.63 (s, 4H), 2.30 (s, 3H).

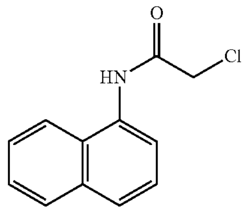 [SMILES: O=C(CCl)Nc1cccc2ccccc12]

2-chloro-N-(naphthalen-1-yl)acetamide (5a24): The synthesis process of 5a1 was performed using 1-naphthylamine (500 mg, 3.49 mmol), triethylamine (388 mg, 3.84 mmol), and chloroacetyl chloride (434 mg, 3.84 mmol) in DCM and then the reaction mixture was purified by column chromatography (n-hexane/EtOAc=2:1) to obtain an intermediate 5a24 in the form of a white solid (350 mg, 45%). $^1H$ NMR (400 MHz, $CDCl_3$) δ: 8.77 (s, 1H), 8.00 (d, J=7.5 Hz, 1H), 7.89 (t, J=9.4 Hz, 2H), 7.76 (d, J=8.2 Hz, 1H), 7.60-7.49 (m, 3H), 4.36 (s, 2H).

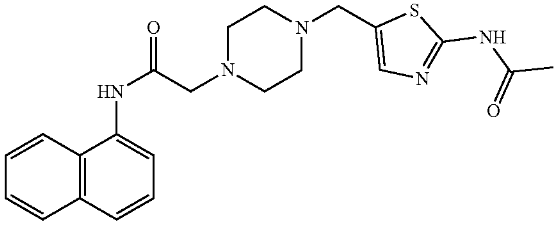 [SMILES: CC(=O)Nc1ncc(CN2CCN(CC(=O)Nc3cccc4ccccc34)CC2)s1]

2-(4-((2-acetamidothiazol-5-yl)methyl)piperazin-1-yl)-N-(naphthalen-1-yl)acetamide (A-24): The synthesis method of the compound A-1 was performed using the intermediate 5a24 (220 mg, 1.00 mmol), the intermediate 3b (425 mg, 1.20 mmol), and $K_2CO_3$ (331 mg, 2.40 mmol) in acetonitrile, and the reaction mixture was purified by column chromatography (DCM:MOH=40:1) to obtain a compound A-24 in the form of a white solid (246 mg, 58%). Mp: 257-258° C. $^1H$ NMR (400 MHz, $CDCl_3$) δ: 10.72 (s, 1H), 9.90 (s, 1H), 8.24 (dd, J=7.6, 1.1 Hz, 1H), 7.89-7.86 (m, 1H), 7.84-7.82 (m, 1H), 7.66 (d, J=8.2 Hz, 1H), 7.57-7.47 (m, 3H), 7.25 (d, J=0.9 Hz, 1H), 3.77 (d, J=1.0 Hz, 2H), 3.30 (s, 2H), 2.79 (s, 4H), 2.68 (s, 4H), 2.30 (s, 3H).

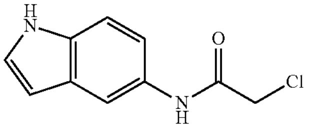 [SMILES: O=C(CCl)Nc1ccc2[nH]ccc2c1]

2-chloro-N-(1H-indol-5-yl)acetamide (5a25): The synthesis process of 5a1 was performed using 5-aminoindole (500 mg, 3.78 mmol), triethylamine (420 mg, 4.16 mmol), and chloroacetyl chloride (470 mg, 4.16 mmol) in DCM and then the reaction mixture was purified by column chromatography (n-hexane/EtOAc=2:1) to obtain an intermediate 5a25 in the form of a white solid (470 mg, 60%). $^1H$ NMR (400 MHz, $CDCl_3$) δ: 8.26 (s, 1H), 8.19 (s, 1H), 7.87 (d, J=2.1 Hz, 1H), 7.36 (dt, J=8.6, 0.8 Hz, 1H), 7.27 (d, J=2.1 Hz, 1H), 7.25-7.22 (m, 1H), 6.54 (ddd, J=3.1, 2.0, 0.9 Hz, 1H), 4.22 (s, 2H).

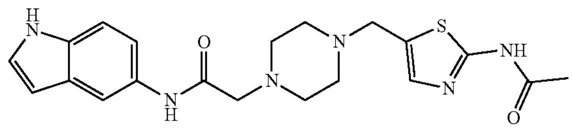 [SMILES: CC(=O)Nc1ncc(CN2CCN(CC(=O)Nc3ccc4[nH]ccc4c3)CC2)s1]

2-(4-((2-acetamidothiazol-5-yl)methyl)piperazin-1-yl)-N-(1H-indol-5-yl)acetamide (A-25): The synthesis method of the compound A-1 was performed using the intermediate 5a25 (210 mg, 1.00 mmol), the intermediate 3b (425 mg, 1.20 mmol), and $K_2CO_3$ (331 mg, 2.40 mmol) in acetonitrile, and the reaction mixture was purified by column chromatography (DCM:MOH=40:1) to obtain a compound A-25 in the form of a white solid (245 mg, 59%). Mp: 216-219° C. $^1$H NMR (400 MHz, $CDCl_3$) δ: 10.71 (s, 1H), 9.06 (s, 1H), 8.15 (s, 1H), 7.88-7.86 (m, 1H), 7.35-7.28 (m, 2H), 7.22-7.20 (m, 2H), 6.52 (ddd, J=3.1, 2.0, 0.9 Hz, 1H), 3.72 (d, J=1.0 Hz, 2H), 3.16 (s, 2H), 2.68 (d, J=4.8 Hz, 4H), 2.60 (s, 4H), 2.29 (s, 3H).

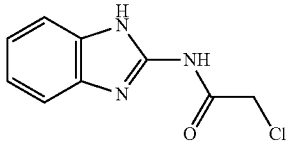 [SMILES: O=C(CCl)Nc1nc2ccccc2[nH]1]

N-(1H-benzo[d]imidazol-2-yl)-2-chloroacetamide (5a26): The synthesis method of 5a1 was performed using 2-aminobenzimidazole (500 mg, 3.76 mmol), triethylamine (417 mg, 4.13 mmol), and chloroacetyl chloride (466 mg, 4.13 mmol) in DCM and then the reaction mixture was purified by column chromatography (n-hexane/EtOAc=2:1) to obtain an intermediate 5a26 in the form of a white solid (632 mg, 80%). $^1$H NMR (400 MHz, DMSO-$d_6$) δ: 7.44 (d, J=2.7 Hz, 1H), 7.17 (dd, J=5.8, 3.2 Hz, 1H), 7.12 (d, J=2.8 Hz, 1H), 6.96 (dd, J=5.8, 3.1 Hz, 1H), 6.90 (s, 1H), 4.37 (s, 2H), 4.16 (s, 1H).

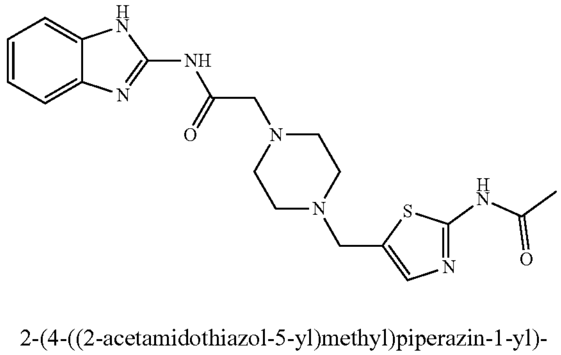

2-(4-((2-acetamidothiazol-5-yl)methyl)piperazin-1-yl)-N-(1H-benzo[d]imidazol-2-yl)acetamide (A-26): The synthesis method of the compound A-1 was performed using the intermediate 5a26 (210 mg, 1.00 mmol), the intermediate 3b (425 mg, 1.20 mmol), and $K_2CO_3$ (331 mg, 2.40 mmol) in acetonitrile, and the reaction mixture was purified by column chromatography (DCM:MOH=20:1) to obtain a compound A-26 in the form of a white solid (104 mg, 25%). Mp: 233-236° C. $^1$H NMR (400 MHz, DMSO-$d_6$) δ: 12.06 (s, 1H), 11.93 (s, 1H), 11.06 (s, 1H), 7.43 (s, 2H), 7.26 (s, 1H), 7.08 (dd, J=6.1, 3.1 Hz, 2H), 3.64 (s, 2H), 3.28 (s, 2H), 2.59 (s, 4H), 2.45 (s, 4H), 2.11 (s, 3H).

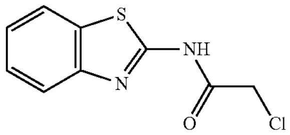 [SMILES: O=C(CCl)Nc1nc2ccccc2s1]

N-(benzo[d]thiazol-2-yl)-2-chloroacetamide (5a27): The synthesis process of 5a1 was performed using 2-aminobenzimidazole (500 mg, 3.33 mmol), triethylamine (370 mg, 3.66 mmol), and chloroacetyl chloride (413 mg, 3.66 mmol) in DCM and then the reaction mixture was purified by column chromatography (n-hexane/EtOAc=5:1) to obtain an intermediate 5a27 in the form of a white solid (477 mg, 63%). $^1$H NMR (400 MHz, $CDCl_3$) δ: 9.76 (s, 1H), 7.87-7.79 (m, 2H), 7.48 (ddd, J=8.2, 7.2, 1.3 Hz, 1H), 7.36 (ddd, J=8.2, 7.2, 1.2 Hz, 1H), 4.32 (s, 2H).

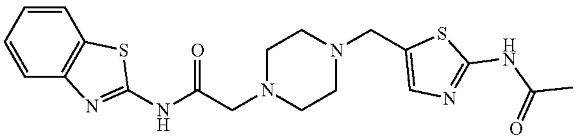 [SMILES: CC(=O)Nc1ncc(CN2CCN(CC(=O)Nc3nc4ccccc4s3)CC2)s1]

2-(4-((2-acetamidothiazol-5-yl)methyl)piperazin-1 yl)-N-(benzo[d]thiazol-2-yl)acetamide (A-27): The synthesis method of the compound A-1 was performed using the intermediate 5a27 (227 mg, 1.00 mmol), the intermediate 3b (425 mg, 1.20 mmol), and $K_2CO_3$ (331 mg, 2.40 mmol) in acetonitrile, and the reaction mixture was purified by column chromatography (DCM:MOH=40:1) to obtain a compound A-27 in the form of a white solid (129 mg, 30%). Mp: 248-249° C. $^1$H NMR (400 MHz, DMSO-$d_6$) δ: 11.94 (s, 1H), 7.97 (dd, J=7.9, 1.1 Hz, 1H), 7.74 (dd, J=8.1, 0.9 Hz, 1H), 7.43 (td, J=7.7, 1H), 7.30 (td, J=7.7, 1.2 Hz, 1H), 7.26 (s, 1H), 3.63 (s, 2H), 3.29 (s, 2H), 2.56 (s, 4H), 2.44 (s, 4H), 2.11 (s, 3H).

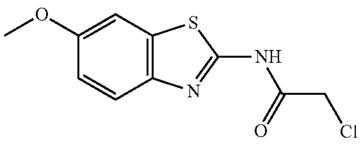 [SMILES: COc1ccc2nc(NC(=O)CCl)sc2c1]

2-chloro-N-(6-methoxybenzo[d]thiazol-2-yl)acetamide (5a28): The synthesis method of 5a1 was performed using 2-amino-6-methoxybenzothiazole (500 mg, 2.77 mmol), triethylamine (308 mg, 3.05 mmol), and chloroacetyl chloride (344 mg, 3.05 mmol) in DCM and then the reaction mixture was purified by column chromatography (n-hexane/EtOAc=5:1) to obtain an intermediate 5a28 in the form of a white solid (425 mg, 60%). $^1$H NMR (400 MHz, $CDCl_3$) δ: 9.66 (s, 1H), 7.71 (d, J=8.9 Hz, 1H), 7.30 (d, J=2.6 Hz, 1H), 7.07 (dd, J=8.9, 2.6 Hz, 1H), 4.30 (s, 2H), 3.88 (s, 3H).

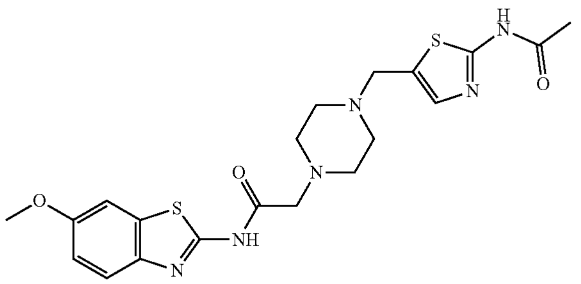 [SMILES: COc1ccc2nc(NC(=O)CN3CCN(Cc4cnc(NC(C)=O)s4)CC3)sc2c1]

2-(4-((2-acetamidothiazol-5-yl)methyl)piperazin-1 yl)-N-(6-methoxybenzo[d]thiazol-2-yl)acetamide (A-28): The synthesis method of the compound A-1 was performed using the intermediate 5a28 (256 mg, 1.00 mmol), the intermediate 3b (425 mg, 1.20 mmol), and $K_2CO_3$ (331 mg, 2.40 mmol) in acetonitrile, and the reaction mixture was purified by column chromatography (DCM:MOH=20:1) to obtain a compound A-28 in the form of a white solid (333 mg, 72%). Mp: 241-244° C. $^1$H NMR (400 MHz, DMSO-$d_6$) δ: 11.93 (s, 1H), 7.62 (d, J=8.8 Hz, 1H), 7.56 (d, J=2.6 Hz, 1H), 7.26 (s, 1H), 7.02 (dd, J=8.8, 2.6 Hz, 1H), 3.80 (s, 3H), 3.63 (d, J=1.0 Hz, 2H), 3.27 (s, 2H), 2.55 (d, J=5.6 Hz, 4H), 2.44 (s, 4H), 2.11 (s, 3H).

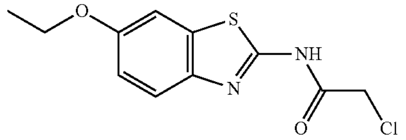 [SMILES: CCOc1ccc2nc(NC(=O)CCl)sc2c1]

2-chloro-N-(6-ethoxybenzo[d]thiazol-2-yl)acetamide (5a29): The synthesis method of 5a1 was performed using 2-amino-6-ethoxybenzothiazole (500 mg, 2.57 mmol), triethylamine (288 mg, 2.83 mmol), and chloroacetyl chloride (319 mg, 2.83 mmol) in DCM and then the reaction mixture was purified by column chromatography (n-hexane/EtOAc=1:1) to obtain an intermediate 5a29 in the form of a white solid (660 mg, 96%). $^1$H NMR (400 MHz, $CDCl_3$) δ: 7.69 (dd, J=8.9, 0.4 Hz, 1H), 7.29 (d, J=2.5 Hz, 1H), 7.06 (dd, J=8.9, 2.5 Hz, 1H), 4.30 (s, 2H), 4.09 (q, J=7.0 Hz, 2H), 1.45 (t, J=7.0 Hz, 3H).

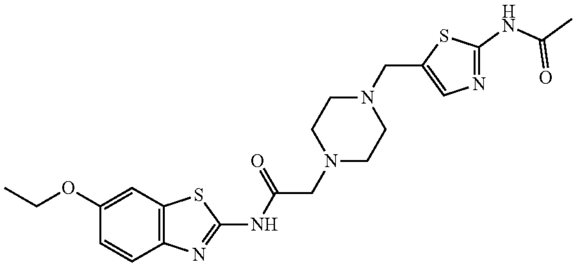 [SMILES: CCOc1ccc2nc(NC(=O)CN3CCN(Cc4cnc(NC(C)=O)s4)CC3)sc2c1]

2-(4-((2-acetamidothiazol-5 yl)methyl)piperazin-1 yl)-N-(6-ethoxybenzo[d]thiazol-2-yl)acetamide (A-29): The synthesis method of the compound A-1 was performed using the intermediate 5a29 (270 mg, 1.00 mmol), the intermediate 3b (425 mg, 1.20 mmol), and $K_2CO_3$ (331 mg, 2.40 mmol) in acetonitrile, and the reaction mixture was purified by column chromatography (DCM MOH=20:1) to obtain a compound A-29 in the form of a white solid (240 mg, 51%). Mp: 244-246° C. $^1$H NMR (400 MHz, DMSO-$d_6$) δ: 11.94 (s, 1H), 7.61 (d, J=8.8 Hz, 1H), 7.54 (d, J=2.6 Hz, 1H), 7.26 (s, 1H), 7.01 (dd, J=8.8, 2.6 Hz, 1H), 4.07 (q, J=7.0 Hz, 2H), 3.63 (s, 2H), 3.30 (s, 2H), 2.58-2.52 (m, 4H), 2.44 (s, 4H), 2.11 (s, 3H), 1.35 (t, J=7.0 Hz, 3H).

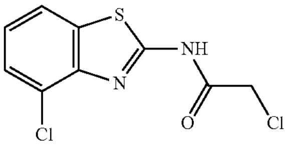 [SMILES: O=C(CCl)Nc1nc2c(Cl)cccc2s1]

2-chloro-N-(4-chlorobenzo[d]thiazol-2-yl)acetamide (5a30): The synthesis method of 5a1 was performed using 2-amino-4-chlorobenzothiazole (500 mg, 2.70 mmol), triethylamine (303 mg, 2.98 mmol), and chloroacetyl chloride (336 mg, 2.98 mmol) in DCM and then the reaction mixture was purified by column chromatography (n-hexane/EtOAc=5:1) to obtain an intermediate 5a30 in the form of a white solid (350 mg, 49%). $^1$H NMR (400 MHz, $CDCl_3$) δ: 9.94 (s, 1H), 7.74 (dd, J=8.0, 1.1 Hz, 1H), 7.50 (dd, J=7.8, 1.0 Hz, 1H), 7.29 (t, J=7.9 Hz, 1H), 4.33 (s, 2H).

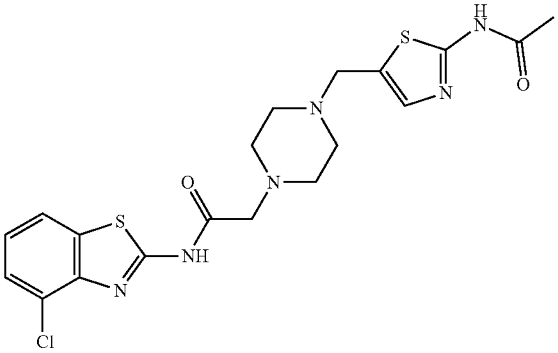 [SMILES: CC(=O)Nc1ncc(CN2CCN(CC(=O)Nc3nc4c(Cl)cccc4s3)CC2)s1]

2-(4-((2-acetamidothiazol-5-yl)methyl)piperazin-1-yl)-N-(4-chlorobenzo[d]thiazol-2-yl)acetamide (A-30): The synthesis method of the compound A-1 was performed using the intermediate 5a30 (262 mg, 1.00 mmol), the intermediate 3b (425 mg, 1.20 mmol), and $K_2CO_3$ (331 mg, 2.40 mmol) in acetonitrile, and the reaction mixture was purified by column chromatography (DCM:MOH=20:1) to obtain a compound A-30 in the form of a white solid (88 mg, 19%). Mp: 255-257° C. $^1$H NMR (400 MHz, DMSO-$d_6$) δ: 11.94 (s, 1H), 7.95 (dd, J=8.0, 1.1 Hz, 1H), 7.52 (dd, J=7.8, 1.1 Hz, 1H), 7.30 (t, J=7.9 Hz, 1H), 7.26 (s, 1H), 3.34 (s, 2H), 2.57-2.55 (m, 4H), 2.44 (s, 4H), 2.12 (s, 3H).

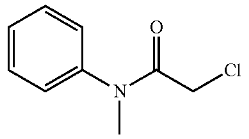

2-chloro-N-methyl-N-phenylacetamide (6): NaH (318 mg, 2.12 mmol) was slowly added to a solution of the compound 5a1 (300 mg, 1.77 mmol) in DMF (20 mL) at 0° C. and then added with iodomethane (51 mg, 2.12 mmol). The reaction mixture was stirred at room temperature for 1 hour. The mixture was extracted with EtOAc oil to obtain an intermediate 6 (233 mg, 70%). $^1H$ NMR (400 MHz, $CDCl_3$) δ: 7.49-7.37 (m, 4H), 7.24 (dd, J=1.8, 1.1 Hz, 1H), 3.85 (s, 2H), 3.32 (s, 3H).

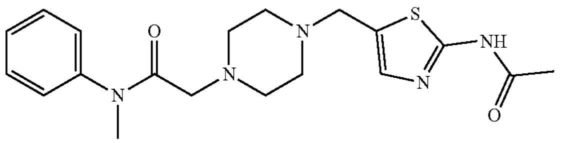 [SMILES: CC(=O)Nc1ncc(CN2CCN(CC(=O)N(C)c3ccccc3)CC2)s1]

2-(4-((2-acetamidothiazol-5-yl)methyl)piperazin-1-yl)-N-methyl-N-phenylacetamide (A-31): The synthesis method of the compound A-1 was performed using the intermediate 6a1 (183 mg, 1.00 mmol), the intermediate 3b (425 mg, 1.20 mmol), and $K_2CO_3$ (331 mg, 2.40 mmol) in acetonitrile, and the reaction mixture was purified by column chromatography (DCM:MOH=30:1) to obtain a compound A-31 in the form of a white solid (105 mg, 31%). Mp: 208-210° C. $^1H$ NMR (400 MHz, $CDCl_3$) δ: 12.25 (s, 1H), 7.41 (dd, J=8.3, 6.6 Hz, 2H), 7.34 (t, J=7.2 Hz, 1H), 7.20 (d, J=1.6 Hz, 1H), 7.18 (d, J=0.9 Hz, 2H), 3.63 (s, 2H), 3.26 (s, 3H), 2.91 (s, 2H), 2.47 (d, J=13.9 Hz, 8H), 2.30 (s, 3H).

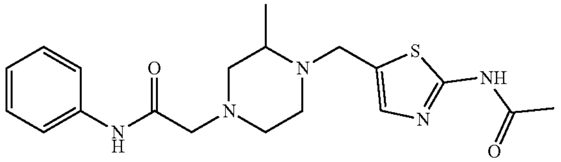 [SMILES: CC(=O)Nc1ncc(CN2CCN(CC(=O)Nc3ccccc3)CC2C)s1]

2-(4-((2-acetamidothiazol-5 yl)methyl)-3-methylpiperazin-1-yl)-N-phenylacetamide (A-32): The synthesis method of the compound A-1 was performed using the intermediate 5a1 (255 mg, 1.51 mmol), the intermediate 3c (460 mg, 1.81 mmol), and $K_2CO_3$ (250 mg, 1.81 mmol) in acetonitrile, and the reaction mixture was purified by column chromatography (DCM:MOH=30:1) to obtain a compound A-32 in the form of a white solid (173 mg, 30%). Mp: 174-176° C. $^1H$ NMR (400 MHz, $CDCl_3$) δ: 10.91 (s, 1H), 9.06 (s, 1H), 7.56-7.54 (m, 2H), 7.35-7.31 (m, 2H), 7.22 (s, 1H), 7.13-7.08 (m, 1H), 4.04 (d, J=14.3 Hz, 1H), 3.70 (d, J=14.5 Hz, 1H), 3.10 (d, J=2.8 Hz, 2H), 2.84-2.81 (m, 1H), 2.75-2.72 (m, 2H), 2.62 (s, 1H), 2.54-2.40 (m, 2H), 2.31 (s, 3H), 2.26-2.25 (m, 1H), 1.19 (d, J=6.2 Hz, 3H).

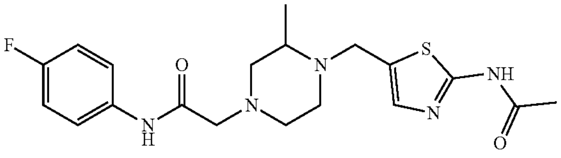 [SMILES: CC(=O)Nc1ncc(CN2CCN(CC(=O)Nc3ccc(F)cc3)CC2C)s1]

2-(4-((2-acetamidothiazol-5-yl)methyl)-3-methylpiperazin-1-yl)-N-(4-fluorophenyl)acetamide (A-33): The synthesis method of the compound A-1 was performed using the intermediate 5a11 (200 mg, 1.06 mmol), the intermediate 3c (323 mg, 1.27 mmol), and $K_2CO_3$ (175 mg, 1.27 mmol) in acetonitrile, and the reaction mixture was purified by column chromatography (DCM:MOH=50:1) to obtain a compound A-33 in the form of a light yellow solid (130 mg, 30%). Mp: 102-105° C. $^1H$ NMR (400 MHz, $CDCl_3$) δ: 11.15 (s, 1H), 9.04 (s, 1H), 7.53-7.49 (m, 2H), 7.22 (s, 1H), 7.04-7.00 (m, 2H), 4.04 (d, J=14.6 Hz, 1H), 3.72 (d, J=14.6 Hz, 1H), 3.10 (d, J=2.7 Hz, 2H), 2.82 (dd, J=11.1, 3.1 Hz, 1H), 2.73 (d, J=7.3 Hz, 2H), 2.65-2.60 (m, 1H), 2.51 (t, J=10.1 Hz, 1H), 2.46-2.40 (m, 1H), 2.31 (s, 3H), 2.26 (d, J=9.6 Hz, 1H), 1.19 (d, J=6.2 Hz, 3H).

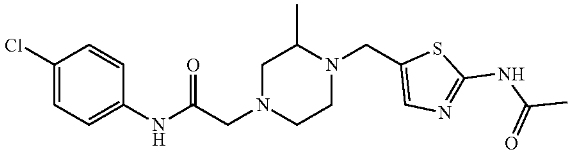 [SMILES: CC(=O)Nc1ncc(CN2CCN(CC(=O)Nc3ccc(Cl)cc3)CC2C)s1]

2-(4-((2-acetamidothiazol-5 yl)methyl)-3-methylpiperazin-1-yl)-N-(4-chlorophenyl)acetamide (A-34): The synthesis method of the compound A-1 was performed using the intermediate 5a12 (200 mg, 0.98 mmol), the intermediate 3c (295 mg, 1.16 mmol), and $K_2CO_3$ (163 mg, 1.16 mmol) in acetonitrile, and the reaction mixture was purified by column chromatography (DCM:MOH=50:1) to obtain a compound A-34 in the form of a white solid (120 mg, 30%). Mp: 184-187° C. $^1H$ NMR (400 MHz, $CDCl_3$) δ: 12.51 (d, J=11.3 Hz, 1H), 9.09 (s, 1H), 7.54-7.48 (m, 2H), 7.30-7.26 (m, 2H), 7.23 (s, 1H), 4.05 (d, J=14.5 Hz, 1H), 3.72 (d, J=14.6 Hz, 1H), 3.11 (d, J=2.9 Hz, 2H), 2.84 (dt, J=11.6, 2.9 Hz, 1H), 2.73 (dt, J=10.2, 4.3 Hz, 2H), 2.66-2.60 (m, 1H), 2.54-2.41 (m, 2H), 2.34 (s, 3H), 2.30-2.24 (m, 1H), 1.19 (d, J=6.1 Hz, 3H).

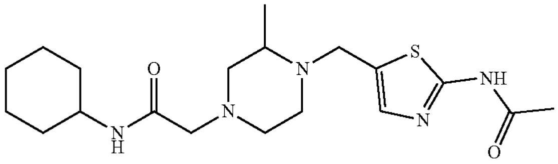 [SMILES: CC(=O)Nc1ncc(CN2CCN(CC(=O)NC3CCCCC3)CC2C)s1]

2-(4-((2-acetamidothiazol-5-yl)methyl)-3-methylpiperazin-1-yl)-N-cyclohexylacetamide (A-35): The synthesis method of the compound A-1 was performed using the intermediate 5a20 (200 mg, 1.14 mmol), the intermediate 3c (348 mg, 1.37 mmol), and $K_2CO_3$ (169 mg, 1.37 mmol) in acetonitrile, and the reaction mixture was purified by column chromatography (DCM:MOH=50:1) to obtain a compound A-35 in the form of a white solid (120 mg, 27%). Mp: 184-187° C. $^1H$ NMR (400 MHz, $CDCl_3$) δ: 12.34 (s, 1H), 7.21 (s, 1H), 7.00 (d, J=8.7 Hz, 1H), 4.01 (d, J=14.5 Hz, 1H), 3.78 (dtd, J=14.1, 10.0, 8.4, 4.2 Hz, 1H), 3.69 (d, J=14.6 Hz, 1H), 3.49-3.48 (m, 1H), 3.01-2.88 (m, 2H), 2.82-2.74 (m, 1H), 2.63 (dd, J=10.1, 3.2 Hz, 2H), 2.57 (d, J=9.3 Hz, 1H), 2.43-2.35 (m, 2H), 2.32 (s, 3H), 2.21-2.12 (m, 2H), 1.87 (dt, J=13.0, 4.2 Hz, 2H), 1.69 (d, J=15.1 Hz, 2H), 1.60 (dt, J=13.0, 3.8 Hz, 1H), 1.41-1.31 (m, 2H), 1.22-1.17 (m, 2H), 1.15 (d, J=6.1 Hz, 3H).

Scheme 3. Synthesis of intermediate 4a31

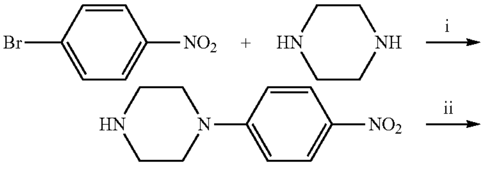

8a31

-continued

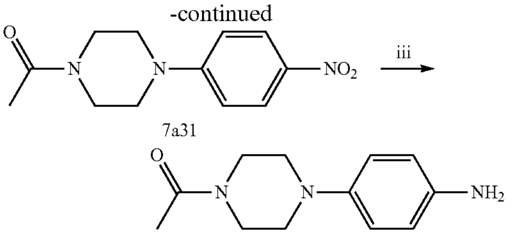

7a31

4a31

Reagents and conditions: (i) $K_2CO_3$, DMSO, 80° C., 6 h; (ii) acetyl chloride, TEA, DCM, r.t., 1 h.

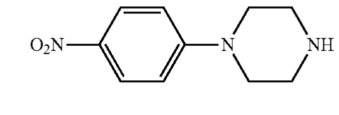 [SMILES: O=[N+]([O-])c1ccc(N2CCNCC2)cc1]

1-(4-nitrophenyl)piperazine (8a31): 4-bromo-1-nitrobenze (3.00 g, 14.58 mmol) was added to gusxirdor of piperazine (1.92 g, 22.28 mmol) and $K_2CO_3$ (3.08 g, 22.28 mmol) in DMSO (80 mL). The reaction mixture was stirred at 80° C. for 8 hours. The reaction mixture was cooled at room temperature and extracted with EtOAc to obtain an intermediate 8a31 in the form of a yellow solid (1.94 g, 65%). $^1H$ NMR (400 MHz, $CDCl_3$) δ: 8.15-8.11 (m, 2H), 6.85-6.82 (m, 2H), 3.44 (t, J=5.1 Hz, 4H), 3.07 (s, 4H).

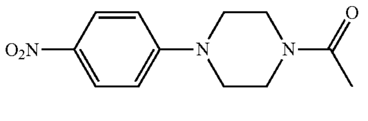

1-(4-(4-nitrophenyl)piperazin-1-yl)ethan-1-one (7a31): Acetyl chloride (418 mg, 5.31 mmol) in DCM (50 mL) was added dropwise to a solution of the intermediate 8a31 (1.00 g, 4.83 mmol) and trimethylamine (541 mg, 5.31 mmol) in DCM at 0° C. The reaction mixture was stirred at room temperature for 1 hour. DCM was evaporated in vacuum and the resulting residue was purified by column chromatography (DCM:MeOH=30:1) to obtain an intermediate 7a31 in the form of a yellow solid (1.16 g, 96%). $^1H$ NMR (500 MHz, $CDCl_3$) δ: 8.20-8.13 (m, 2H), 6.88-6.80 (m, 2H), 3.82 (t, J=5.4 Hz, 2H), 3.68 (t, J=5.2 Hz, 2H), 3.47 (dt, J=21.4, 5.6 Hz, 4H), 2.17 (s, 3H).

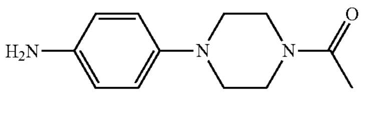 [SMILES: CC(=O)N1CCN(c2ccc([N+](=O)[O-])cc2)CC1]

1-(4-(4-aminophenyl)piperazin-1-yl)ethan-1-one (4a31): The intermediate 7a31 (1.16 g, 4.64 mg) was added to a solution of 10% palladium (98 mg, 0.93 mmol) on carbon in anhydrous MeOH (50 mL). The reaction mixture was stirred at room temperature overnight under hydrogen. The reaction mixture was filtered through celite, the residue was washed with EtOH, and the filtrate was evaporated in vacuum to obtain an intermediate 4a31 in the form of a white solid (1.13 g, 99%). $^1H$ NMR (400 MHz, $CDCl_3$) δ: 6.84-6.79 (m, 2H), 6.70-6.63 (m, 2H), 3.78-3.72 (m, 2H), 3.63-3.58 (m, 2H), 3.00 (dt, J=12.8, 5.2 Hz, 4H), 2.13 (s, 3H).

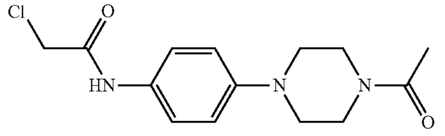 [SMILES: CC(=O)N1CCN(c2ccc(NC(=O)CCl)cc2)CC1]

N-(4-(4-acetylpiperazin-1-yl)phenyl)-2-chloroacetamide (5a31): The synthesis method of 5a1 was performed using the intermediate 4a31 (1.13 mg, 5.16 mmol), triethylamine (579 mg, 5.68 mmol), and chloroacetyl chloride (641 mg, 5.68 mmol) in DCM and then the reaction mixture was purified by column chromatography (DCM/MeOH=30:1) to obtain an intermediate 5a31 in the form of a green solid (1.13 mg, 74%). $^1H$ NMR (400 MHz, $CDCl_3$) δ: 8.14 (s, 1H), 7.49-7.41 (m, 2H), 6.93 (d, J=8.6 Hz, 2H), 4.19 (s, 2H), 3.78 (t, J=5.2 Hz, 2H), 3.63 (t, J=5.2 Hz, 2H), 3.15 (dt, J=13.9, 5.3 Hz, 4H), 2.14 (s, 3H).

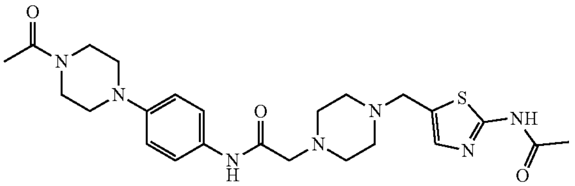 [SMILES: CC(=O)Nc1ncc(CN2CCN(CC(=O)Nc3ccc(N4CCN(C(C)=O)CC4)cc3)CC2)s1]

2-(4-((2-acetamidothiazol-5 yl)methyl)piperazin-1-yl)-N-(4-(4-acetylpiperazin-1-yl)phenyl)acetamide (A-36): The synthesis method of the compound A-1 was performed using the intermediate 5a31 (295 mg, 1.00 mmol), the intermediate 3b (425 mg, 1.20 mmol), and $K_2CO_3$ (165 mg, 1.20 mmol) in acetonitrile, and the reaction mixture was purified by column chromatography (DCM:MOH=30:1) to obtain a compound A-36 in the form of a white solid (51 mg, 10%). Mp: 180-182° C. $^1H$ NMR (500 MHz, $CDCl_3$) δ: 11.77 (s, 1H), 8.97 (s, 1H), 7.48-7.46 (m, 2H), 7.23 (s, 1H), 6.91 (d, J=8.5 Hz, 2H), 3.78 (t, J=5.2 Hz, 2H), 3.72 (s, 2H), 3.63 (t, J=5.0 Hz, 2H), 3.15-3.09 (m, 6H), 2.66 (s, 4H), 2.59 (s, 4H), 2.18 (s, 6H).

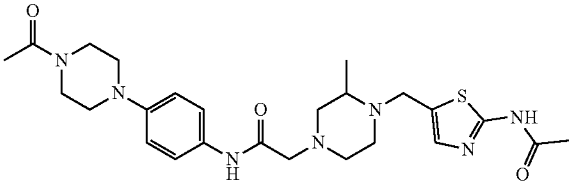 [SMILES: CC(=O)Nc1ncc(CN2CCN(CC(=O)Nc3ccc(N4CCN(C(C)=O)CC4)cc3)CC2C)s1]

2-(4-((2-acetamidothiazol-5-yl)methyl)-3-methylpiperazin-1-yl)-N-(4-(4-acetylpiperazin-1-yl)phenyl)acetamide (A-37): The synthesis method of the compound A-1 was performed using the intermediate 5a31 (295 mg, 1.00 mmol), the intermediate 3c (305 mg, 1.20 mmol), and $K_2CO_3$ (165 mg, 1.20 mmol) in acetonitrile, and the reaction mixture was purified by column chromatography (DCM: MOH=20:1) to obtain a compound A-37 in the form of a light yellow solid (204 mg, 40%). Mp: 232-232° C. $^1H$ NMR (500 MHz, $CDCl_3$) δ: 12.28 (s, 1H), 8.91 (s, 1H), 7.43 (d, J=8.5 Hz, 2H), 6.86 (d, J=8.5 Hz, 2H), 4.01 (d, J=14.5 Hz, 1H), 3.73 (t, J=5.1 Hz, 2H), 3.68 (d, J=14.5 Hz, 1H), 3.59 (t, J=5.1 Hz, 2H), 3.16-3.01 (m, 6H), 2.81-2.76 (m, 1H), 2.69 (d, J=10.0 Hz, 2H), 2.48-2.43 (m, 1H), 2.39 (t, J=10.2

Hz, 1H), 2.29 (s, 3H), 2.23 (dd, J=20.4, 10.5 Hz, 2H), 2.11 (s, 3H), 1.15 (d, J=6.2 Hz, 3H).

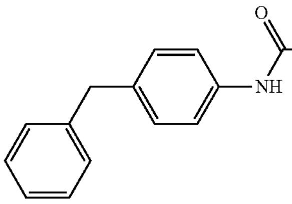

N-(4-benzylphenyl)-2-chloroacetamide (5a32): The synthesis method of 5a1 was performed using 4-aminodiphenylmethane (300 mg, 1.64 mmol), triethylamine (184 mg, 1.80 mmol), and chloroacetyl chloride (203 mg, 1.80 mmol) in DCM and then the reaction mixture was purified by column chromatography (n-hexane/EtOAc=5:1) to obtain an intermediate 5a32 in the form of a purple solid (1.13 mg, 74%). $^{1}$H NMR (400 MHz, $CDCl_3$) δ: 8.25 (s, 1H), 7.49-7.44 (m, 2H), 7.31-7.27 (m, 2H), 7.23-7.14 (m, 5H), 4.19 (s, 2H), 3.96 (s, 2H).

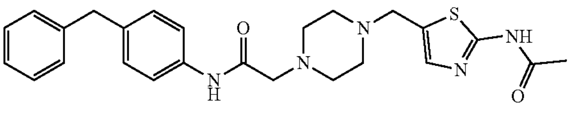 [SMILES: CC(=O)Nc1ncc(CN2CCN(CC(=O)Nc3ccc(Cc4ccccc4)cc3)CC2)s1]

2-(4-((2-acetamidothiazol-5-yl)methyl)piperazin-1-yl)-N-(4-benzylphenyl)acetamide (A-38): The synthesis method of the compound A-1 was performed using the compound 5a32 (414 mg, 1.60 mmol), the intermediate 3b (676 mg, 1.91 mmol), and $K_2CO_3$ (264 mg, 1.91 mmol) in acetonitrile, and the reaction mixture was purified by column chromatography (DCM:MOH=40:1) to obtain a compound A-38 in the form of a light yellow solid (70 mg, 15%). Mp: 132-134° C. $^{1}$H NMR (400 MHz, $CDCl_3$) δ: 11.10 (s, 1H), 9.02 (s, 1H), 7.49-7.45 (m, 2H), 7.27 (d, J=1.4 Hz, 1H), 7.25 (d, J=0.7 Hz, 1H), 7.21 (d, J=1.0 Hz, 1H), 7.21-7.18 (m, 1H), 7.18-7.14 (m, 4H), 3.95 (s, 2H), 3.71 (d, J=1.0 Hz, 2H), 3.13 (s, 2H), 2.64 (s, 4H), 2.57 (s, 4H), 2.30 (s, 3H).

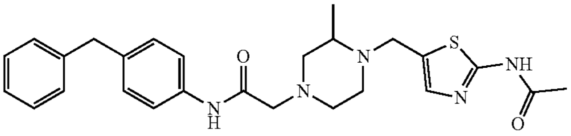 [SMILES: CC(=O)Nc1ncc(CN2CCN(CC(=O)Nc3ccc(Cc4ccccc4)cc3)CC2C)s1]

2-(4-((2-acetamidothiazol-5-yl)methyl)-3-methylpiperazin-1-yl)-N-(4-benzylphenyl)acetamide (A-39): The synthesis method of the compound A-1 was performed using the intermediate 5a32 (400 mg, 1.54 mmol), the intermediate 3c (468 mg, 1.84 mmol), and $K_2CO_3$ (255 mg, 1.84 mmol) in acetonitrile, and the reaction mixture was purified by column chromatography (DCM:MOH=30:1) to obtain a compound A-39 in the form of a light yellow solid (157 mg, 33%). Mp: 193-195° C. $^{1}$H NMR (400 MHz, $CDCl_3$) δ: 11.96 (s, 1H), 9.00 (s, 1H), 7.48-7.44 (m, 2H), 7.27 (d, J=1.4 Hz, 1H), 7.25 (q, J=1.4 Hz, 1H), 7.21 (d, J=0.9 Hz, 1H), 7.21-7.18 (m, 1H), 7.17-7.13 (m, 4H), 4.04 (d, J=14.6 Hz, 1H), 3.94 (s, 2H), 3.69 (d, J=14.5 Hz, 1H), 3.09 (d, J=2.7 Hz, 2H), 2.84-2.78 (m, 1H), 2.72 (dd, J=9.8, 2.8 Hz, 2H), 2.61 (s, 1H), 2.52-2.38 (m, 2H), 2.32 (s, 3H), 2.29-2.23 (m, 1H), 1.18 (d, J=6.2 Hz, 3H).

Scheme 4. Synthesis of intermediate 4a33

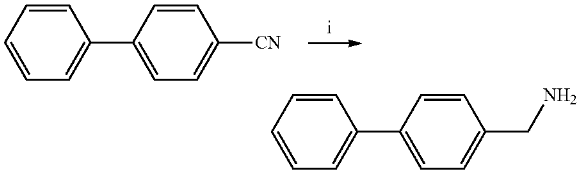

4a33

Reagents and conditions: (i) $LiAlH_4$, THF, 0° C.-r.t., 1.5 h.

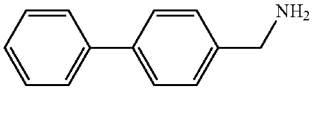

[1,1'-biphenyl]-4-ylmethanamine (4a33): Lithium aluminum hydride (424 mg, 11.16 mmol) was added portionwise to a solution of 4-cyanobiphenyl (500 mg, 2.79 mmol) in THF (30 mL) at 0° C. The reaction mixture was stirred at room temperature for 0.5 hours. The mixture was extracted with DCM to obtain an intermediate 4a33 in the form of a white solid (450 mg, 88%). $^{1}$H NMR (400 MHz, $CDCl_3$) δ: 7.58 (ddt, J=7.6, 6.3, 1.7 Hz, 4H), 7.45-7.32 (m, 5H), 3.92 (s, 2H).

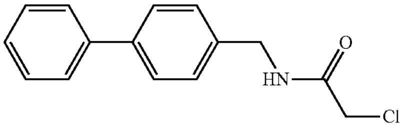 [SMILES: O=C(CCl)NCc1ccc(-c2ccccc2)cc1]

N-([1,1'-biphenyl]-4-ylmethyl)-2-chloroacetamide (5a33): The synthesis method of 5a1 was performed using intermediate 4a33 (300 mg, 1.64 mmol), triethylamine (184 mg, 1.80 mmol), and chloroacetyl chloride (203 mg, 1.80 mmol) in DCM and then the reaction mixture was purified by column chromatography (n-hexane/EtOAc=1:1) to obtain an intermediate 5a33 in the form of a white solid (472 mg, 100%). $^{1}$H NMR (400 MHz, $CDCl_3$) δ: 8.25 (s, 1H), 7.49-7.44 (m, 2H), 7.31-7.27 (m, 2H), 7.23-7.14 (m, 5H), 4.19 (s, 2H), 3.96 (s, 2H). $^{1}$H NMR (400 MHz, $CDCl_3$) δ: 7.62-7.56 (m, 4H), 7.48-7.42 (m, 2H), 7.41-7.32 (m, 3H), 6.92 (s, 1H), 4.55 (d, J=5.9 Hz, 2H), 4.14 (s, 2H).

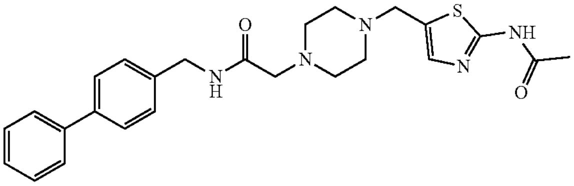 [SMILES: CC(=O)Nc1ncc(CN2CCN(CC(=O)NCc3ccc(-c4ccccc4)cc3)CC2)s1]

N-([1,1'-biphenyl]-4-ylmethyl)-2-(4-((2-acetamidothiazol-5-yl)methyl)piperazin-1-yl)acetamide (A-40): The synthesis method of the compound A-1 was performed using the intermediate 5a33 (290 mg, 1.12 mmol), the intermediate 3b (475 mg, 1.34 mmol), and $K_2CO_3$ (171 mg, 1.34 mmol) in acetonitrile, and the reaction mixture was purified by column chromatography (DCM:MOH=30:1) to obtain a compound A-40 in the form of a light yellow solid (32 mg, 6%). Mp: 167-170° C. $^1$H NMR (500 MHz, $CDCl_3$) δ: 10.38 (s, 1H), 7.59 (dd, J=8.0, 6.4 Hz, 4H), 7.45 (t, J=7.5 Hz, 2H), 7.35 (d, J=7.9 Hz, 3H), 7.19 (s, 1H), 4.53 (d, J=6.0 Hz, 2H), 3.68 (s, 2H), 3.10 (s, 2H), 2.59 (s, 4H), 2.51 (s, 4H), 2.28 (s, 3H).

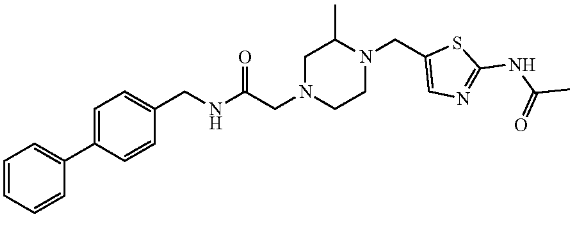 [SMILES: CC(=O)Nc1ncc(CN2CCN(CC(=O)NCc3ccc(-c4ccccc4)cc3)CC2C)s1]

N-([1,1'-biphenyl]-4-ylmethyl)-2-(4-((2-acetamidothiazol-5-yl)methyl)-3-methylpiperazin-1-yl)acetamide (A-41): The synthesis method of the compound A-1 was performed using the intermediate 5a33 (290 mg, 1.12 mmol), the intermediate 3c (340 mg, 1.34 mmol), and $K_2CO_3$ (171 mg, 1.34 mmol) in acetonitrile, and the reaction mixture was purified by column chromatography (DCM: MOH=40:1) to obtain a compound A-41 in the form of a light yellow solid (37 mg, 7%). Mp: 215-216° C. $^1$H NMR (500 MHz, $CDCl_3$) δ: 9.86 (s, 1H), 7.58 (t, J=8.9 Hz, 4H), 7.44 (d, J=7.6 Hz, 2H), 7.35 (dd, J=11.4, 7.6 Hz, 3H), 7.18 (s, 1H), 4.52 (d, J=5.1 Hz, 2H), 3.99 (d, J=14.5 Hz, 1H), 3.69 (d, J=14.6 Hz, 1H), 3.06 (s, 2H), 2.71 (dd, J=45.1, 11.9 Hz, 4H), 2.39 (dt, J=37.8, 10.5 Hz, 3H), 2.26 (s, 3H), 1.11 (d, J=6.2 Hz, 3H).

Example 2

Synthesis of Compound of Chemical Formula 3

A compound of Chemical Formula 3 below was prepared by the following process.

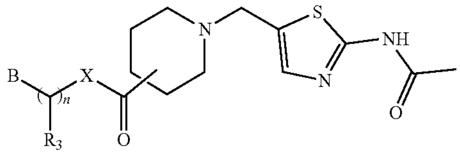

Scheme 5. Synthesis of B-1 to B-12

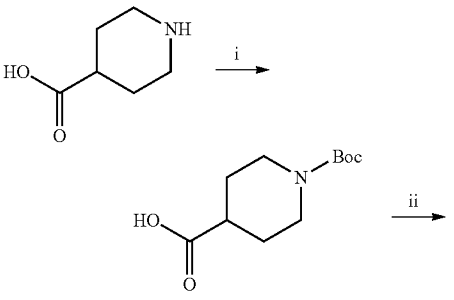

b1

-continued

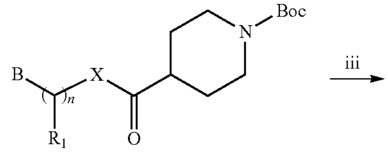

b2a-b2l

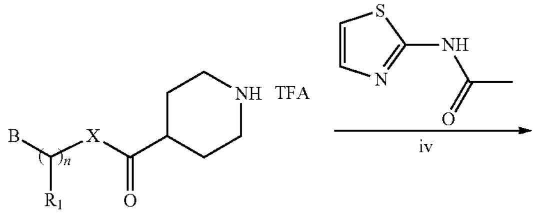

b3a-b3l

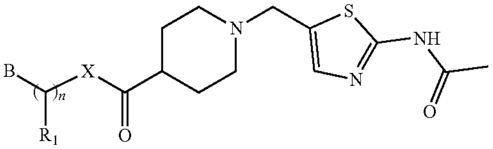

B-1~B-12

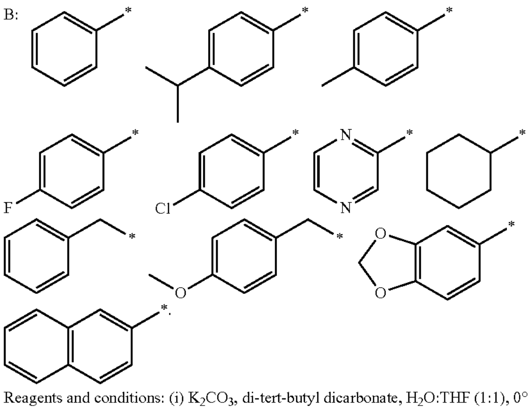

Reagents and conditions: (i) $K_2CO_3$, di-tert-butyl dicarbonate, $H_2O$:THF (1:1), 0° C.-r.t., overnight; (ii) amine compounds, EDCI, DMAP, DCM, 0° C.-r.t., overnight (iii) TFA, DCM, r.t., overnight; (iv) paraformaldehyde, AcOH, 100° C., 4 h

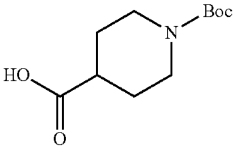

1-(tert-butoxycarbonyl)piperidine-4-carboxylic acid (b1): Di-tert-butyl dicarbonate (845 mg, 3.87 mmol) in THF (8 mL) was added dropwise to a suspension of 4-piperidine carboxylic acid (500 mg, 3.87 mmol) and $K_2CO_3$ (1.07 g, 7.74 mmol) in water (8 mL) at 0° C. The reaction mixture was stirred overnight at room temperature. The THF was removed in vacuum, the water layer was washed with DCM and then the water layer was acidified with 1 N HCl (pH=4). The reaction mixture was filtered to obtain an intermediate b1 in the form of a white solid (770 mg, 87%). $^1$H NMR (400 MHz, $CDCl_3$): δ: 4.02 (d, J=13. 1 Hz, 2H), 2.86 (t, J=12. 5 Hz, 2H), 2.49 (tt, J=10.9, 3.9 Hz, 1H), 1.65 (dtd, J=13.4, 11.2, 4.2 Hz, 2H), 1.46 (s, 9H).

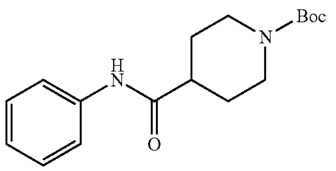 [SMILES: CC(C)(C)OC(=O)N1CCC(C(=O)Nc2ccccc2)CC1]

tert-butyl 4-(phenylcarbamoyl)piperidine-1-carboxylate (b2a): 1 portion of intermediate b1 and 1 portion of EDCI (326 mg, 1.70 mmol) were added to a solution of aniline (122 mg, 1.31 mmol) and DMAP (208 mg, 1.70 mmol) in DCM (30 mL) at room temperature. The reaction mixture was stirred overnight at room temperature. The reaction was quenched with $TH_2O$ and extracted with DCM, and then the DCM layer was washed with brine, dried over $NaSO_4$, and filtered in vacuum and concentrated. The concentrate was purified by flash column chromatography (DCM: MeOH=98:2) to obtain an intermediate b2a in the form of a white solid (374 mg, 94%). $^1$H NMR (400 MHz, $CDCl_3$): δ: 7.51 (d, J=7.9 Hz, 2H), 7.32 (dd, J=8.5, 7.4 Hz, 2H), 7.18 (s, 1H), 7.11 (t, J=7.4 Hz, 1H), 4.19 (bs, 2H), 2.79 (t, J=12.6 Hz, 2H), 2.38 (tt, J=11.5, 3.8 Hz, 1H), 1.75 (dtd, J=13.3, 11.8, 4.4 Hz, 2H), 1.47 (s, 9H).

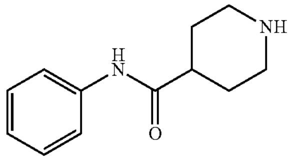 [SMILES: O=C(Nc1ccccc1)C1CCNCC1]

N-phenylpiperidine-4-carboxamide (b3a): TFA (1.39 g, 12.16 mmol) was added to a solution of the intermediate b2a (370 mg, 1.22 mmol) in DCM (30 mL) at room temperature. The reaction mixture was stirred overnight at room temperature. DCM was evaporated in vacuum and the resulting residue reacted with $NaHCO_3$ in DCM. After filtration, an intermediate b3b was obtained in the form of a white solid (232 mg, 94%). $^1$H NMR (400 MHz, DMSO-$d_6$): δ: 10.02 (s, 1H), 7.59 (d, J=7.9 Hz, 2H), 7.32-7.27 (m, 3H), 7.05 (t, J=7.3 Hz, 1H), 2.93 (td, J=12.6, 3.2 Hz, 3H), 2.63 (tt, J=11.1, 3.9 Hz, 1H), 2.00-1.91 (m, 3H), 1.80 (dtd, J=14.8, 11.9, 4.0 Hz, 3H).

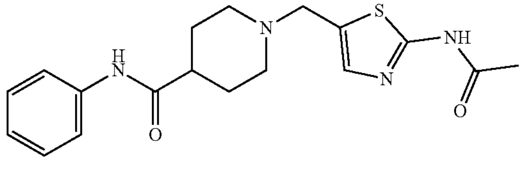 [SMILES: CC(=O)Nc1ncc(CN2CCC(C(=O)Nc3ccccc3)CC2)s1]

1-((2-acetamidothiazol-5-yl)methyl)N-phenylpiperidine-4-carboxamide (B-1): Paraformaldehyde (338 mg, 11.26 mmol) was added to a solution of 2-acetamidothiazole (240 mg, 1.69 mmol) and the intermediate b3a (230 mg, 1.13 mmol) in acetic acid (20 mL) while stirring at 100° C. The reaction mixture was stirred at 100° C. for 4 hours. Acetic acid was evaporated in vacuum. The resulting residue was purified by flash column chromatography (DCM: MeOH=20:1) to obtain a compound B-1 in the form of a white solid (180 mg, 45%). Mp: 172-174° C. $^1$H NMR (400 MHz, DMSO-$d_6$): δ: 11.94 (s, 1H), 9.82 (s, 1H), 7.64-7.51 (m, 2H), 7.32-7.20 (m, 3H), 7.05-6.96 (m, 1H), 3.63 (s, 2H), 2.90 (dt, J=11.8, 3.3 Hz, 2H), 2.30 (tt, J=11.4, 3.7 Hz, 1H), 2.12 (s, 3H), 1.97 (td, J=11.7, 2.6 Hz, 2H), 1.81-1.57 (m, 4H).

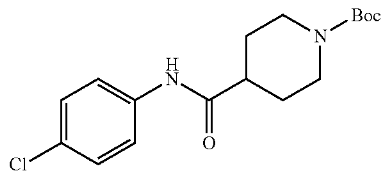 [SMILES: CC(C)(C)OC(=O)N1CCC(C(=O)Nc2ccc(Cl)cc2)CC1]

tert-butyl 4-((4-chlorophenyl)carbamoyl)piperidine-1-carboxylate (b2b): The synthesis method of the intermediate b2a was performed using the intermediate b1 (500 mg, 2.18 mmol), 4-chloroaniline (278 mg, 2.18 mmol), EDCI (502 mg, 2.62 mmol), and DMAP (320 mg, 2.62 mmol) in DCM, and then the reaction mixture was purified by flash column chromatography (n-hexane:EtOAc=5:1) to obtain an intermediate b2b in the form of a white solid (645 mg, 87%). $^1$H NMR (400 MHz, $CDCl_3$) δ: 7.51-7.43 (m, 2H), 7.30-7.27 (m, 2H), 7.18 (s, 1H), 4.18 (bs, 2H), 2.79 (t, J=12.8 Hz, 2H), 2.37 (tt, J=11.5, 3.8 Hz, 1H), 1.90 (d, J=12.4 Hz, 2H), 1.74 (dtd, J=13.3, 11.8, 4.4 Hz, 2H), 1.47 (s, 9H).

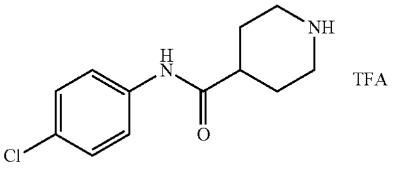 [SMILES: O=C(Nc1ccc(Cl)cc1)C1CCNCC1]

N-(4-chlorophenyl)piperidine-4-carboxamide compound with 2,2,2-trifluoroacetaldehyde (1:1) (b3b): TFA (2.09 g, 18.30 mmol) was added to a solution of the intermediate b2b (620 mg, 1.83 mmol) in DCM (30 mL) at room temperature. The reaction mixture was stirred overnight at room temperature. DCM was evaporated in vacuum. The resulting residue was washed with MeOH (2 mL) and filtered to obtain an intermediate b3b in the form of a white solid (610 mg, 99%). $^1$H NMR (400 MHz, DMSO-$d_6$): δ: 10.18 (s, 1H), 8.53 (d, J=111.5 Hz, 1H), 7.66-7.59 (m, 2H), 7.40-7.30 (m, 2H), 2.93 (t, J=12.4 Hz, 2H), 2.63 (tt, J=11.0, 3.7 Hz, 1H), 2.01-1.72 (m, 4H).

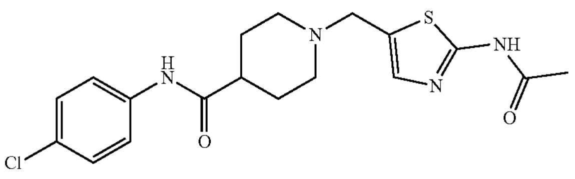 [SMILES: CC(=O)Nc1ncc(CN2CCC(C(=O)Nc3ccc(Cl)cc3)CC2)s1]

1-((2-acetamidothiazol-5-yl)methyl)-N-(4-chlorophenyl) piperidine-4-carboxamide (B-2): The synthesis method of the compound b-1 was performed using 2-acetamidothiazole (127 mg, 0.89 mmol), the intermediate b2b (200 mg, 0.60 mmol), and paraformaldehyde (89 mg, 2.98 mmol) in acetic acid and then the reaction mixture was purified by flash column chromatography (n-hexane:EtOAc=2:1) to obtain a compound B-2 in the form of a white solid (194 mg, 83%). Mp: 258-260° C. $^1$H NMR (400 MHz, DMSO-$d_6$): δ: 11.93

(s, 1H), 9.97 (s, 1H), 7.66-7.57 (m, 2H), 7.38-7.28 (m, 2H), 7.25 (s, 1H), 3.62 (s, 2H), 2.95-2.84 (m, 2H), 2.29 (ddt, J=11.5, 8.0, 3.9 Hz, 1H), 2.12 (s, 3H), 1.97 (td, J=11.7, 2.8 Hz, 2H), 1.80-1.72 (m, 2H), 1.63 (qd, J=12.2, 3.8 Hz, 2H).

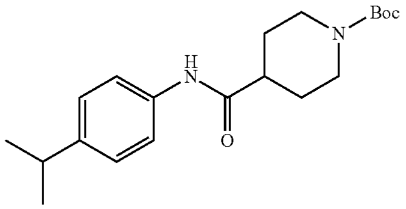 [SMILES: CC(C)c1ccc(NC(=O)C2CCN(C(=O)OC(C)(C)C)CC2)cc1]

tert-butyl 4-((4-isopropylphenyl)carbamoyl)piperidine-1-carboxylate (b2c): The synthesis method of the intermediate b2a was performed using the intermediate b1 (500 mg, 2.18 mmol), 4-isopropylaniline (295 mg, 2.18 mmol), EDCI (502 mg, 2.62 mmol), and DMAP (320 mg, 2.62 mmol) in DCM, and then the reaction mixture was purified by flash column chromatography (n-hexane:EtOAc=10:1) to obtain an intermediate b2c in the form of a white solid (708 mg, 94%). $^{1}$H NMR (400 MHz, $CDCl_3$): δ: 7.44-7.40 (m, 2H), 7.19-7.15 (m, 2H), 4.18 (s, 2H), 2.93-2.73 (m, 3H), 2.36 (tt, J=11.5, 3.8 Hz, 1H), 1.74 (dtd, J=13.3, 11.8, 4.4 Hz, 2H), 1.47 (s, 9H), 1.22 (d, J=7.0 Hz, 6H).

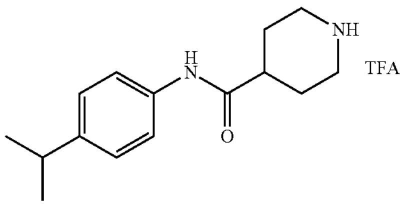 [SMILES: CC(C)c1ccc(NC(=O)C2CCNCC2)cc1]

N-(4-isopropylphenyl)piperidine-4-carboxamide compound with 2,2,2-trifluoroacetaldehyde (1:1) (b3c): The synthesis method of the intermediate b3b was performed using the intermediate b2c (650 mg, 1.88 mmol) and TFA (2.14 g, 18.80 mmol) in DCM to obtain an intermediate b3c in the form of a white solid (570 mg, 89%). $^{1}$H NMR (400 MHz, DMSO-$d_6$): δ: 9.95 (s, 1H), 8.54 (d, J=110.6 Hz, 1H), 7.54-7.42 (m, 2H), 7.22-7.11 (m, 2H), 3.33 (d, J=2.0 Hz, 2H), 2.98-2.79 (m, 3H), 2.62 (tt, J=11.1, 3.8 Hz, 1H), 2.01-1.73 (m, 4H), 1.17 (d, J=6.9 Hz, 6H).

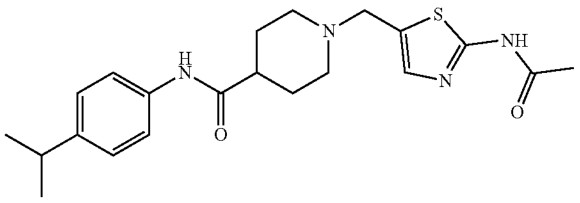 [SMILES: CC(=O)Nc1ncc(CN2CCC(C(=O)Nc3ccc(C(C)C)cc3)CC2)s1]

1-((2-acetamidothiazol-5-yl)methyl)-N-(4-isopropylphenyl)piperidine-4-carboxamide (B-3): The synthesis method of the compound b-1 was performed using 2-acetamidothiazole (124 mg, 0.87 mmol), the intermediate b3c (200 mg, 0.58 mmol), and paraformaldehyde (87 mg, 2.91 mmol) in acetic acid (20 mL) and then the reaction mixture was purified by flash column chromatography (DCM:MeOH=20:1) to obtain a compound B-3 in the form of a white solid (20 mg, 9%). Mp: 257-258° C. $^{1}$H NMR (400 MHz, DMSO-$d_6$) δ: 11.93 (s, 1H), 9.73 (s, 1H), 7.53-7.45 (m, 2H), 7.25 (s, 1H), 7.17-7.10 (m, 2H), 3.62 (s, 2H), 2.93-2.77 (m, 3H), 2.12 (s, 3H), 2.01-1.92 (m, 2H), 1.77-1.57 (m, 5H), 1.16 (d, J=6.9 Hz, 6H).

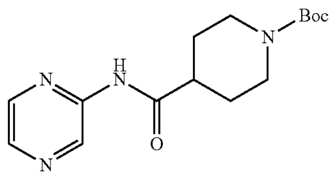 [SMILES: CC(C)(C)OC(=O)N1CCC(C(=O)Nc2cnccn2)CC1]

tert-butyl4-(pyrazin-2-ylcarbamoyl)piperidine-1-carboxylate (b2d): The synthesis method of the intermediate b2a was performed using the intermediate b1 (500 mg, 2.18 mmol), 2-aminopyrazine (207 mg, 2.18 mmol), EDCI (502 mg, 2.62 mmol), and DMAP (320 mg, 2.62 mmol) in DCM, and then the reaction mixture was purified by flash column chromatography (n-hexane:EtOAc=5:1) to obtain an intermediate b2d in the form of a white solid (627 mg, 94%). $^{1}$H NMR (400 MHz, $CDCl_3$) δ: 9.59 (d, J=1.6 Hz, 1H), 8.65 (s, 1H), 8.37 (d, J=2.6 Hz, 1H), 8.19 (dd, J=2.7, 1.6 Hz, 1H), 4.19 (s, 2H), 2.83 (t, J=12.7 Hz, 2H), 2.52 (tt, J=11.4, 3.8 Hz, 1H), 1.91 (s, 2H), 1.76 (dtd, J=13.4, 11.8, 4.4 Hz, 3H), 1.47 (s, 9H).

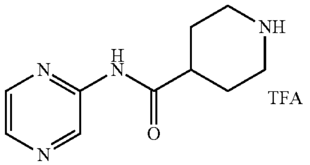 [SMILES: O=C(Nc1cnccn1)C1CCNCC1]

N-(pyrazin-2-yl)piperidine-4-carboxamide compound with 2,2,2-trifluoroacetaldehyde (1:1) (b3d): The synthesis method of the intermediate b3b was performed using the intermediate b2d (600 mg, 1.96 mmol) and TFA (2.23 g, 19.58 mmol) in DCM to obtain an intermediate b3d in the form of a white solid (530 mg, 89%). $^{1}$H NMR (400 MHz, DMSO-$d_6$): δ: 10.88 (s, 1H), 9.32 (d, J=1.5 Hz, 1H), 8.71-8.58 (m, 1H), 8.41 (dd, J=2.6, 1.5 Hz, 1H), 8.37 (d, J=2.6 Hz, 1H), 3.34 (s, 2H), 2.98-2.78 (m, 3H), 2.05-1.94 (m, 2H), 1.81 (qd, J=14.4, 13.1, 4.1 Hz, 2H).

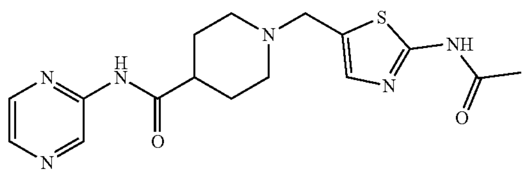 [SMILES: CC(=O)Nc1ncc(CN2CCC(C(=O)Nc3cnccn3)CC2)s1]

1-((2-acetamidothiazol-5-yl)methyl)-N-(pyrazin-2-yl)piperidine-4-carboxamide (B-4): The synthesis method of the compound b-1 was performed using 2-acetamidothiazole (141 mg, 0.99 mmol), the intermediate b3d (200 mg, 0.66 mmol), and paraformaldehyde (99 mg, 3.30 mmol) in acetic acid (20 mL) and then the reaction mixture was purified by flash column chromatography (DCM:MeOH=20:1) to obtain a compound B-4 in the form of a white solid (108 mg, 45%). Mp: 178-180° C. $^{1}$H NMR (400 MHz, DMSO-$d_6$): δ:

11.94 (s, 1H), 10.70 (s, 1H), 9.32 (d, J=1.5 Hz, 1H), 8.38 (dd, J=2.6, 1.6 Hz, 1H), 8.34 (d, J=2.6 Hz, 1H), 7.26 (s, 1H), 3.64 (s, 2H), 2.92-2.86 (m, 2H), 2.12 (s, 3H), 2.02-1.93 (m, 3H), 1.79 (d, J=11.8 Hz, 2H), 1.62 (qd, J=12.1, 3.7 Hz, 2H).

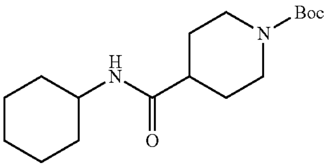 [SMILES: CC(C)(C)OC(=O)N1CCC(C(=O)NC2CCCCC2)CC1]

tert-butyl 4-(cyclohexylcarbamoyl)piperidine-1-carboxylate (b2e): The synthesis method of the intermediate b2a was performed using the intermediate b1 (500 mg, 2.18 mmol), cyclohexylamine (216 mg, 2.18 mmol), EDCI (502 mg, 2.62 mmol), and DMAP (320 mg, 2.62 mmol) in DCM, and then the reaction mixture was purified by flash column chromatography (n-hexane:EtOAc=1:1) to obtain an intermediate b2e in the form of a white solid (619 mg, 91%). $^1$H NMR (400 MHz, $CDCl_3$): δ: 5.27 (d, J=8.1 Hz, 1H), 3.76 (dddd, J=14.7, 10.7, 8.0, 3.9 Hz, 1H), 2.73 (t, J=12.8 Hz, 2H), 2.16 (tt, J=11.6, 3.8 Hz, 1H), 1.79 (dd, J=13.1, 3.5 Hz, 2H), 1.73-1.60 (m, 4H), 1.45 (s, 9H), 1.42-1.30 (m, 2H), 1.22-1.03 (m, 3H).

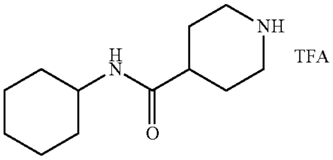 [SMILES: O=C(NC1CCCCC1)C1CCNCC1]

N-cyclohexylpiperidine-4-carboxamide compound with 2,2,2-trifluoroacetaldehyde (1:1) (b3e): The synthesis method of the intermediate b3b was performed using the intermediate b2e (590 mg, 1.90 mmol) and TFA (2.16 g, 19.00 mmol) in DCM to obtain an intermediate b3e in the form of a white solid (540 mg, 92%). $^1$H NMR (400 MHz, DMSO-$d_6$): δ: 8.44 (d, J=75.4 Hz, 1H), 7.80 (d, J=7.9 Hz, 1H), 3.28 (dt, J=12.9, 3.7 Hz, 3H), 2.86 (td, J=12.5, 3.3 Hz, 2H), 2.37 (tt, J=11.0, 3.9 Hz, 1H), 1.85-1.50 (m, 9H), 1.30-1.07 (m, 5H).

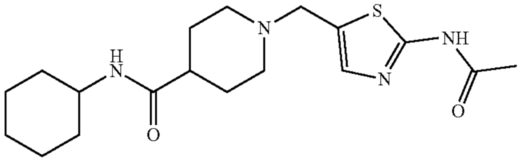 [SMILES: CC(=O)Nc1ncc(CN2CCC(C(=O)NC3CCCCC3)CC2)s1]

1-((2-acetamidothiazol-5-yl)methyl)-N-cyclohexylpiperidine-4-carboxamide (B-5): The synthesis method of the compound b-1 was performed using 2-acetamidothiazole (139 mg, 0.98 mmol), the intermediate b3e (200 mg, 0.65 mmol), and paraformaldehyde (98 mg, 3.25 mmol) in acetic acid (20 mL) and then the reaction mixture was purified by flash column chromatography (DCM:MeOH=40:1) to obtain a compound B-5 in the form of a white solid (80 mg, 34%). Mp: 231-232° C. $^1$H NMR (400 MHz, DMSO-$d_6$): δ: 11.93 (s, 1H), 7.60 (d, J=7.9 Hz, 1H), 7.24 (s, 1H), 2.83 (d, J=11.2 Hz, 2H), 2.12 (s, 3H), 1.96-1.87 (m, 3H), 1.66 (td, J=9.2, 4.0 Hz, 4H), 1.60-1.51 (m, 5H), 1.27-1.06 (m, 7H).

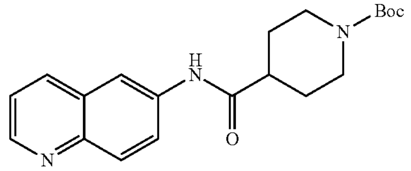 [SMILES: CC(C)(C)OC(=O)N1CCC(C(=O)Nc2ccc3ncccc3c2)CC1]

tert-butyl 4-(quinolin-6-ylcarbamoyl)piperidine-1-carboxylate (b2f): The synthesis method of the intermediate b2a was performed using the intermediate b1 (500 mg, 2.18 mmol), 6-aminoquinoline (314 mg, 2.18 mmol), EDCI (502 mg, 2.62 mmol), and DMAP (320 mg, 2.62 mmol) in DCM, and then the reaction mixture was purified by flash column chromatography (DCM:MeOH=20:1) to obtain an intermediate b2f in the form of a white solid (665 mg, 86%). $^1$H NMR (400 MHz, $CDCl_3$): δ: 8.84 (dd, J=4.2, 1.7 Hz, 1H), 8.40 (d, J=2.4 Hz, 1H), 8.168.01 (m, 2H), 7.53 (dd, J=9.0, 2.4 Hz, 1H), 7.44 (s, 1H), 7.39 (dd, J=8.3, 4.2 Hz, 1H), 4.21 (s, 2H), 2.83 (t, J=12.7 Hz, 2H), 2.46 (tt, J=11.4, 3.8 Hz, 1H), 1.95 (d, J=12.1 Hz, 2H), 1.871.73 (m, 2H), 1.48 (s, 9H).

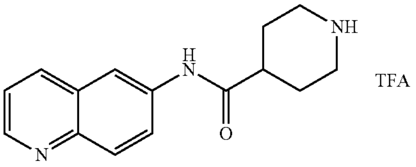 [SMILES: O=C(Nc1ccc2ncccc2c1)C1CCNCC1]

N-(quinolin-6-yl)piperidine-4-carboxamide compound with 2,2,2-trifluoroacetaldehyde (1:1) (b3j): The synthesis method of the intermediate b3b was performed using the intermediate b2f (640 mg, 1.80 mmol) and TFA (2.05 g, 18.00 mmol) in DCM to obtain a compound b3f in the form of a yellow solid (620 mg, 98%). $^1$H NMR (400 MHz, DMSO-$d_6$): δ: 10.58 (s, 1H), 8.95 (dd, J=4.6, 1.6 Hz, 1H), 8.77 (d, J=11.3 Hz, 1H), 8.62 (dd, J=8.5, 1.5 Hz, 1H), 8.55 (d, J=2.3 Hz, 1H), 8.51-8.42 (m, 1H), 8.09 (d, J=9.1 Hz, 1H), 7.94 (dd, J=9.1, 2.3 Hz, 1H), 7.71 (dd, J=8.4, 4.6 Hz, 1H), 3.39 (dt, J=13.2, 3.4 Hz, 2H), 2.98 (dtd, J=12.7, 9.9, 2.6 Hz, 2H), 2.75 (tt, J=11.1, 3.8 Hz, 1H), 2.12-1.75 (m, 4H).

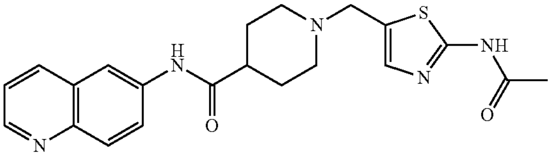 [SMILES: CC(=O)Nc1ncc(CN2CCC(C(=O)Nc3ccc4ncccc4c3)CC2)s1]

1-((2-acetamidothiazol-5 yl)methyl)-N-(quinolin-6-yl)piperidine-4-carboxamide (B-6): The synthesis method of the compound b-1 was performed using 2-acetamidothiazole (121 mg, 0.85 mmol), the intermediate b3f (200 mg, 0.57 mmol), and paraformaldehyde (85 mg, 2.84 mmol) in acetic acid (20 mL) and then the reaction mixture was purified by flash column chromatography (DCM:MeOH=20:1) to obtain a compound B-6 in the form of a white solid (215 mg, 93%). Mp: 234-236° C. $^1$H NMR (400 MHz, DMSO-$d_6$): δ: 12.21 (s, 1H), 10.39 (s, 1H), 8.76 (d, J=3.8 Hz, 1H), 8.34 (d, J=2.3 Hz, 1H), 8.25 (d, J=8.0 Hz, 1H), 7.95 (d, J=9.1 Hz, 1H), 7.78 (dd, J=9.2, 2.4 Hz, 1H), 7.54-7.44 (m, 2H), 4.31 (s, 2H), 3.32 (d, J=11.2 Hz, 2H), 2.82-2.57 (m, 3H), 2.15 (s, 3H), 2.05-1.95 (m, 2H), 1.88 (d, J=11.4 Hz, 2H).

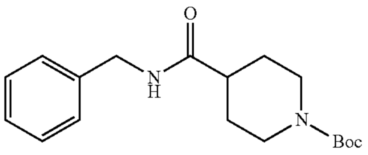 [SMILES: CC(C)(C)OC(=O)N1CCC(C(=O)NCc2ccccc2)CC1]

tert-butyl 4-(benzylcarbamoyl)piperidine-1-carboxylate (b2g): The synthesis method of the intermediate b2a was performed using the intermediate b1 (500 mg, 2.18 mmol), benzyl amine (234 mg, 2.18 mmol), EDCI (502 mg, 2.62 mmol), and DMAP (320 mg, 2.62 mmol) in DCM, and then the reaction mixture was purified by flash column chromatography (DCM:MeOH=40:1) to obtain an intermediate b2g in the form of a white solid (690 mg, 99%). $^1$H NMR (400 MHz, $CDCl_3$): δ: 7.37-7.24 (m, 5H), 5.74 (s, 1H), 4.45 (d, J=5.6 Hz, 2H), 4.12 (bs, J=7.2 Hz, 1H), 2.74 (s, 2H), 2.26 (tt, J=11.6, 3.8 Hz, 1H), 1.88-1.78 (m, 2H), 1.72-1.63 (m, 2H), 1.45 (s, 9H).

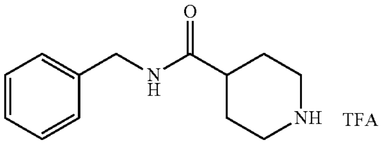 [SMILES: O=C(NCc1ccccc1)C1CCNCC1]

N-benzylpiperidine-4-carboxamide compound with 2,2,2-trifluoro-I13-ethan-1-one (1:1) (b3g): The synthesis method of the intermediate b3b was performed using the intermediate b2g (650 mg, 2.04 mmol) and TFA (2.33 g, 20.41 mmol) in DCM to obtain an intermediate b3g in the form of a yellow solid (640 mg, quantitative yield). $^1$H NMR (400 MHz, DMSO-$d_6$) δ: 8.67-8.26 (m, 3H), 7.39-7.16 (m, 5H), 4.27 (d, J=5.9 Hz, 2H), 3.30 (dt, J=12.7, 3.3 Hz, 2H), 2.90 (dtd, J=12.6, 9.8, 2.8 Hz, 2H), 2.50-2.42 (m, 1H), 1.93-1.68 (m, 4H).

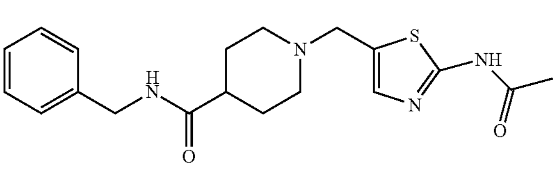 [SMILES: CC(=O)Nc1ncc(CN2CCC(C(=O)NCc3ccccc3)CC2)s1]

1-((2-acetamidothiazol-5-yl)methyl)-N-benzylpiperidine-4-carboxamide (B-7): The synthesis method of the compound b-1 was performed using 2-acetamidothiazole (135 mg, 0.95 mmol), the intermediate b3g (200 mg, 0.63 mmol), and paraformaldehyde (95 mg, 3.17 mmol) in acetic acid (20 mL) and then the reaction mixture was purified by flash column chromatography (DCM:MeOH=50:1) to obtain a compound B-7 in the form of a white solid (100 mg, 42%). Mp: 176-178° C. $^1$H NMR (400 MHz, DMSO-$d_6$): δ: 11.95 (s, 1H), 8.27 (t, J=6.0 Hz, 1H), 7.34-7.18 (m, 5H), 4.25 (d, J=5.9 Hz, 2H), 3.60 (s, 2H), 2.85 (d, J=11.2 Hz, 2H), 2.11 (s, 4H), 1.93 (m, 2H), 1.71-1.51 (m, 4H).

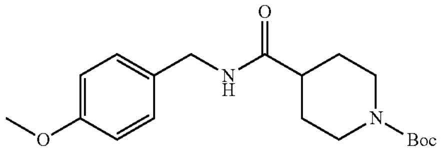 [SMILES: COc1ccc(CNC(=O)C2CCN(C(=O)OC(C)(C)C)CC2)cc1]

tert-butyl 4-((4-methoxybenzyl)carbamoyl)piperidine-1-carboxylate (b2h): The synthesis method of the intermediate b2a was performed using the intermediate b1 (300 mg, 1.32 mmol), 4-methoxybenzylamine (179 mg, 1.31 mmol), EDCI (301 mg, 1.57 mmol), and DMAP (192 mg, 1.57 mmol) in DCM, and then the reaction mixture was purified by flash column chromatography (DCM:MeOH=20:1) to obtain an intermediate b2h in the form of a white solid (346 mg, 76%). $^1$H NMR (400 MHz, $CDCl_3$): δ: 7.21-7.15 (m, 2H), 6.89-6.83 (m, 2H), 5.70 (s, 1H), 4.37 (d, J=5.5 Hz, 2H), 4.12 (q, J=7.2 Hz, 2H), 3.80 (s, 3H), 2.73 (s, 2H), 2.24 (tt, J=11.6, 3.7 Hz, 1H), 1.65 (dtd, J=13.3, 11.9, 4.5 Hz, 2H), 1.45 (s, 9H).

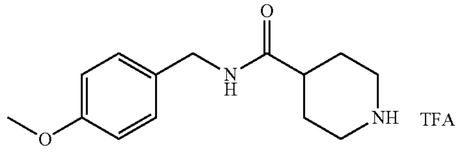 [SMILES: COc1ccc(CNC(=O)C2CCNCC2)cc1]

N-(4-methoxybenzyl)piperidine-4-carboxamide compound with 2,2,2-trifluoroacetaldehyde (1:1) (b3h) The synthesis method of the intermediate b3b was performed using the intermediate b2h (310 mg, 0.89 mmol) and TFA (1.01 g, 8.89 mmol) in DCM to obtain an intermediate b3h in the form of a yellow solid (320 mg, quantitative yield). $^1$H NMR (400 MHz, DMSO-$d_6$): δ: 8.60 (s, 1H), 8.39 (t, J=5.9 Hz, 1H), 8.31 (s, 1H), 7.18-7.12 (m, 2H), 6.92-6.83 (m, 2H), 4.19 (d, J=5.8 Hz, 2H), 3.72 (s, 5H), 3.29 (d, J=12.5 Hz, 2H), 2.88 (td, J=12.5, 9.7 Hz, 2H), 2.44 (dt, J=11.0, 3.9 Hz, 1H), 1.91-1.65 (m, 4H).

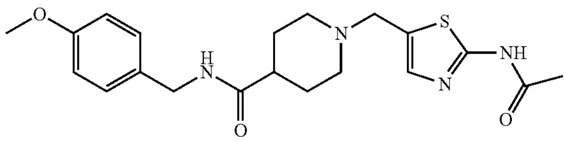 [SMILES: COc1ccc(CNC(=O)C2CCN(Cc3cnc(NC(C)=O)s3)CC2)cc1]

1-((2-acetamidothiazol-5-yl)methyl)-N-(4-methoxybenzyl)piperidine-4-carboxamide (B-8): The synthesis method of the compound b-1 was performed using 2-acetamidothiazole (148 mg, 1.04 mmol), the intermediate b3h (240 mg, 0.69 mmol), and paraformaldehyde (104 mg, 3.47 mmol) in acetic acid (20 mL) and then the reaction mixture was purified by flash column chromatography (DCM:MeOH=50:1) to obtain a compound B-8 in the form of a white solid (90 mg, 32%). Mp: 215-217° C. $^1$H NMR (400 MHz, $CDCl_3$): δ: 11.42 (s, 1H), 7.24-7.12 (m, 3H), 6.88-6.79 (m, 2H), 6.60 (s, 1H), 4.34 (d, J=5.6 Hz, 2H), 3.79 (s, 3H), 3.66 (s, 2H), 2.95 (d, J=11.2 Hz, 2H), 2.21 (s, 3H), 2.02 (d, J=8.2 Hz, 2H).

Scheme 6. Synthesis of 4i to 4j

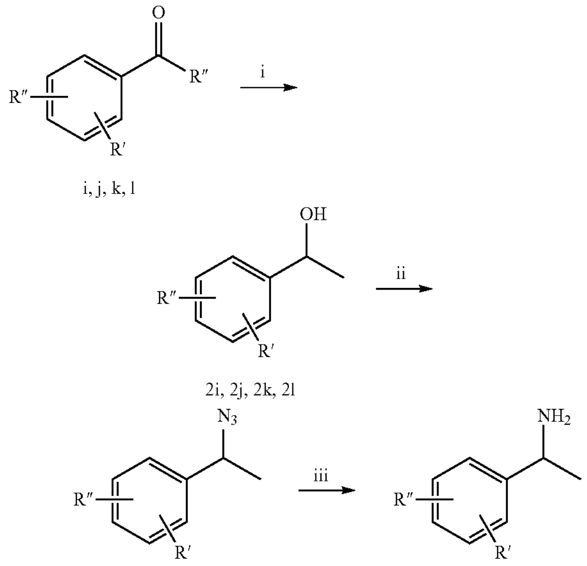

i, j, k, l 2i, 2j, 2k, 2l 3i, 3j, 3k, 3l 4i, 4j, 4k, 4l

Reagents and conditions: (i) MeMgBr, THF, -10° C.-r.t., 3 h or $NaBH_4$, MeOH, 0° C.-r.t., 1 h; (ii) TFA, $NaN_3$, DCM, 0° C.-r.t., 6 h; (iii) $PPh_3$, THF, 0° C.-r.t., 1 day.

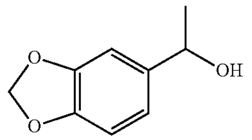

1-(benzo[d][1,3]dioxol-5-yl)ethan-1-ol (176A) (2i): MeMgBr (3.57 g, 29.94 mmol) was added dropwise to a solution of 1,3-benzodioxole-5-carboxaldehyde (3.00 g, 19.98 mmol) in anhydrous THF (100 mL) at −10° C. and the reaction mixture was stirred at room temperature for 3 hours. Thereafter, the reaction was quenched with a saturated $NH_4Cl$ solution and extracted with EtOAc, and then the EtOAc layer was washed with saturated brine, dried over $Na_2SO_4$, filtered and concentrated in vacuum. The concentrate was purified by flash column chromatography (n-hexane:EtOAc=10:1) to obtain a compound 176A in the form of a white solid (3.24 g, 98%). $^1H$ NMR (400 MHz, $CDCl_3$): δ: 6.89 (d, J=1.6 Hz, 1H), 6.84-6.74 (m, 2H), 5.94 (s, 2H), 4.81 (q, J=6.4 Hz, 1H), 1.92 (s, 1H).

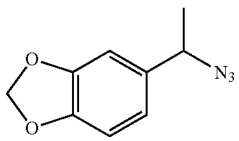

5-(1-azidoethyl)benzo[d][1,3]dioxole (3i): TFA (2.06 g, 18.05 mmol) and $NaN_3$ (313 mg, 4.81 mmol) were added to a stirred solution of the intermediate 2i (200 mg, 1.20 mmol) in DCM (30 mL) at 0° C. The reaction mixture was stirred at room temperature for 6 hours. Thereafter, the reaction was quenched with a saturated $NaHCO_3$ solution and extracted with DCM, and then the DCM layer was washed with saturated brine, dried over $Na_2SO_4$, filtered and concentrated in vacuum to obtain a syrup (200 mg, 87%). $^1H$ NMR (400 MHz, $CDCl_3$): δ: 6.84-6.82 (m, 1H), 6.78 (t, J=0.9 Hz, 2H), 5.97 (s, 2H), 4.53 (q, J=6.8 Hz, 1H), 1.48 (d, J=6.8 Hz, 3H).

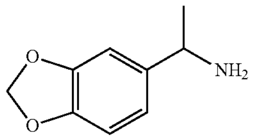

1-(benzo[d][1,3]dioxol-5-yl)ethan-1-amine (4i): $PPh_3$ (521 mg, 1.99 mmol) was added to a stirred solution of the intermediate 3i (190 mg, 0.99 mmol) in THF (40 mL) at 0° C., stirred for 30 minutes, and then added with $H_2O$. The reaction mixture was stirred at room temperature for 24 hours. Thereafter, the reaction mixture was diluted with $H_2O$ and extracted with EtOAcm, and then the EtOAc layer was washed with saturated brine, dried over $Na_2SO_4$, filtered and concentrated in vacuum. The concentrate was purified by flash column chromatography (DCM:MeOH=20:1) to obtain an intermediate 4i in the form of a white solid (199 mg, 99%). $^1H$ NMR (400 MHz, $CDCl_3$): δ: 6.90 (d, J=1.8 Hz, 1H), 6.82 (dd, J=8.0, 1.8 Hz, 1H), 6.75 (d, J=8.0 Hz, 1H), 5.93 (s, 2H), 4.18 (q, J=6.8 Hz, 1H), 1.50 (s, 3H).

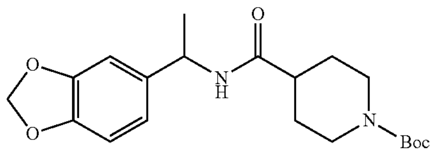 [SMILES: CC(NC(=O)C1CCN(C(=O)OC(C)(C)C)CC1)c1ccc2c(c1)OCO2]

tert-butyl 4-((1-(benzo[d][1,3]dioxol-5-yl)ethyl)carbamoyl)piperidine-1-carboxylate (b2i): The synthesis method of the intermediate b2a was performed using the intermediate b1 (250 mg, 1.09 mmol), the intermediate 4i (180 mg, 1.09 mmol), EDCI (251 mg, 1.31 mmol), and DMAP (160 mg, 1.31 mmol) in DCM, and then the reaction mixture was purified by flash column chromatography (n-hexane EtOAc=10:1) to obtain an intermediate b2i in the form of a white solid (110 mg, 27%). $^1H$ NMR (400 MHz, $CDCl_3$): δ: 6.80-6.73 (m, 3H), 5.94 (s, 2H), 5.59 (d, J=7.7 Hz, 1H), 5.03 (p, J=7.0 Hz, 1H), 4.13 (s, 2H), 2.73 (t, J=12.8 Hz, 2H), 2.20 (tt, J=11.6, 3.8 Hz, 1H), 1.66-1.57 (m, 4H), 1.44 (d, J=5.9 Hz, 12H).

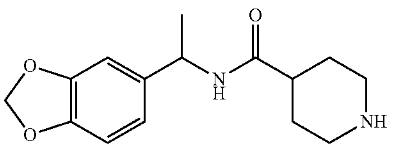 TFA

N-(1-(benzo[d][1,3]dioxol-5-yl)ethyl)piperidine-4-carboxamide compound with 2,2,2-trifluoroacetaldehyde (1:1) (b3i): The synthesis method of the intermediate b3b was performed using the intermediate b2i (100 mg, 0.27 mmol) and TFA (303 mg, 2.66 mmol) in DCM to obtain a compound b3i in the form of a yellow solid (99 mg, 98%). $^1H$ NMR (400 MHz, DMSO-$d_6$): δ: 8.52 (s, 1H), 8.28 (d, J=8.0 Hz, 2H), 6.89-6.70 (m, 3H), 5.97 (s, 2H), 4.81 (p, J=7.1 Hz, 1H), 3.28 (s, 2H), 2.87 (s, 2H), 2.44 (tt, J=11.0, 3.8 Hz, 1H), 1.87-1.58 (m, 4H), 1.29 (d, J=7.0 Hz, 3H).

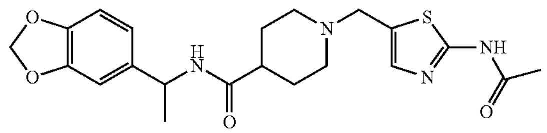 [SMILES: CC(=O)Nc1ncc(CN2CCC(C(=O)NC(C)c3ccc4c(c3)OCO4)CC2)s1]

1-((2-acetamidothiazol-5-yl)methyl)-N-(1-(benzo[d][1,3]dioxol-5-yl)ethyl)piperidine-4-carboxamide (B-9): The synthesis method of the compound b-1 was performed using 2-acetamidothiazole (57 mg, 0.40 mmol), the intermediate b3i (100 mg, 0.27 mmol), and paraformaldehyde (40 mg, 1.34 mmol) in acetic acid (20 mL) and then the reaction mixture was purified by flash column chromatography (DCM:MeOH=20:1) to obtain a compound B-9 in the form of a white solid (52 mg, 45%). Mp:211-213° C. $^1$H NMR (400 MHz, DMSO-$d_6$): δ: 11.93 (s, 1H), 8.07 (d, J=8.2 Hz, 1H), 7.23 (s, 1H), 6.88-6.68 (m, 3H), 5.96 (s, 2H), 4.81 (p, J=7.0 Hz, 1H), 3.59 (s, 2H), 2.88-2.79 (m, 2H), 2.11 (s, 3H), 1.95-1.87 (m, 3H), 1.68-1.45 (m, 4H), 1.27 (d, J=7.0 Hz, 3H).

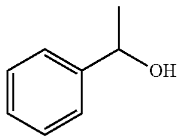

1-phenylethan-1-ol (2j): $NaBH_4$ (315 mg, 8.32 mmol) was added to a solution of acetophenone (1.00 g, 8.32 mmol) in MeOH (50 mL) at 0° C. The reaction mixture was stirred at room temperature for 1 hour. MeOH was evaporated in vacuum and the residue was washed with $H_2O$ and extracted with EtOAc, and then the EtOAc layer was washed with saturated brine, dried over $Na_2SO_4$, filtered and concentrated to obtain an intermediate 2j in the form of a syrup (989 mg, 97%). $^1$H NMR (400 MHz, $CDCl_3$): δ: 7.40-7.26 (m, 5H), 4.89 (q, J=6.5 Hz, 1H), 1.89 (s, 1H), 1.49 (d, J=6.5 Hz, 3H).

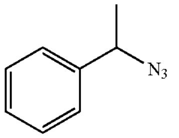

(1-azidoethyl)benzene (3j): The synthesis method of the intermediate 3i was performed using the intermediate 2j (900 mg, 7.37 mmol), TFA (12.60 g, 110.52 mmol), and $NaN_3$ (1.92 g, 29.47 mmol) in DCM (50 mL) and then the reaction mixture was purified by flash column chromatography (DCM:MeOH=20:1) to obtain an intermediate 3j in the form of a white solid (1.00 g, 92%). $^1$H NMR (400 MHz, $CDCl_3$): δ: 7.41-7.34 (m, 4H), 7.34-7.29 (m, 1H), 4.61 (q, J=6.8 Hz, 1H), 1.53 (d, J=6.9 Hz, 3H).

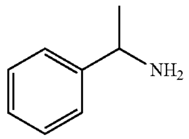

1-phenylethan-1-amine (4j): The synthesis method of the intermediate 4i was performed using the intermediate 3j (1.00 g, 6.79 mmol) and $PPh_3$ (3.56 g, 13.59 mmol) in THF and then the reaction mixture was purified by flash column chromatography (DCM:MeOH=20:1) to obtain an intermediate 4j in the form of a white solid (382 mg, 38%). $^1$H NMR (400 MHz, $CDCl_3$): δ: 7.39-7.31 (m, 4H), 7.20-7.11 (m, 1H), 4.19 (q, J=6.7 Hz, 1H), 1.48 (d, J=6.7 Hz, 3H).

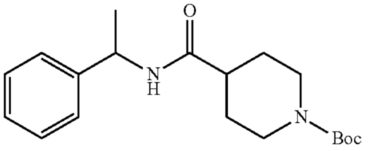 [SMILES: CC(NC(=O)C1CCN(C(=O)OC(C)(C)C)CC1)c1ccccc1]

tert-butyl 4-((1-phenylethyl)carbamoyl)piperidine-1-carboxylate (b2j): The synthesis method of the intermediate b2a was performed using the intermediate b1 (1.44 g, 6.27 mmol), the intermediate 4j (760 mg, 6.27 mmol), EDCI (1.44 g, 7.53 mmol), and DMAP (919 mg, 7.53 mmol) in DCM, and then the reaction mixture was purified by flash column chromatography (n-hexane:EtOAc=10:1) to obtain an intermediate b2j in the form of a white solid (157 mg, 7%). $^1$H NMR (400 MHz, $CDCl_3$): δ: 7.38-7.27 (m, 5H), 5.65 (d, J=7.8 Hz, 1H), 5.13 (p, J=7.1 Hz, 1H), 4.13 (s, 2H), 2.73 (s, 2H), 2.21 (tt, J=11.6, 3.8 Hz, 1H), 1.71-1.61 (m, 2H), 1.49 (d, J=6.8 Hz, 3H), 1.45 (s, 9H).

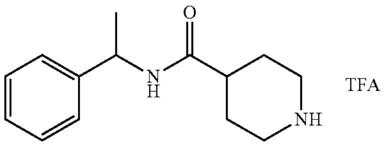 [SMILES: CC(NC(=O)C1CCNCC1)c1ccccc1]

N-(1-phenylethyl)piperidine-4-carboxamide compound with 2,2,2-trifluoroacetaldehyde (1:1) (b3j): The synthesis method of the intermediate b3b was performed using the intermediate b2j (150 mg, 0.45 mmol) and TFA (514 mg, 4.51 mmol) in DCM to obtain an b3j in the form of a white solid (150 mg, quantitative yield). $^1$H NMR (400 MHz, DMSO-$d_6$): δ: 8.58-8.19 (m, 3H), 7.35-7.17 (m, 5H), 4.89 (p, J=7.1 Hz, 1H), 3.28 (s, 3H), 2.87 (ddd, J=9.6, 6.4, 3.2 Hz, 2H), 2.45 (dt, J=10.9, 3.9 Hz, 1H), 1.89-1.60 (m, 4H), 1.34 (d, J=7.0 Hz, 3H).

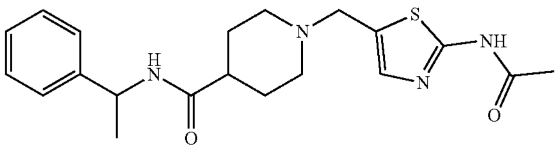 [SMILES: CC(=O)Nc1ncc(CN2CCC(C(=O)NC(C)c3ccccc3)CC2)s1]

1-((2-acetamidothiazol-5-yl)methyl)-N-(1-phenylethyl)piperidine-4-carboxamide (B-10): The synthesis method of the compound b-1 was performed using 2-acetamidothiazole (97 mg, 0.68 mmol), b3j (150 mg, 0.46 mmol), and paraformaldehyde (68 mg, 2.28 mmol) in acetic acid (20 mL) and then the reaction mixture was purified by flash column chromatography (DCM:MeOH=30:1) to obtain a compound B-10 in the form of a white solid (112 mg, 64%). Mp: 178-179° C. $^1$H NMR (400 MHz, DMSO-$d_6$): δ: 11.93 (s, 1H), 8.17 (d, J=8.1 Hz, 1H), 7.33-7.17 (m, 6H), 4.88 (p, J=7.1 Hz, 1H), 3.62-3.55 (m, 2H), 2.89-2.80 (m, 2H), 2.11 (s, 3H), 1.96-1.88 (m, 2H), 1.69-1.46 (m, 4H), 1.31 (d, J=7.0 Hz, 3H).

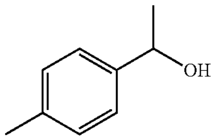

1-(p-tolyl)ethan-1-ol (2k): The synthesis method of the intermediate 2j was performed using 4-methylacetophenone (2.00 g, 14.91 mmol) and $NaBH_4$ (564 mg, 14.91 mmol) in MeOH (50 mL) to obtain 2k in the form of a syrup (1.60 g, 79%). $^1$H NMR (400 MHz, $CDCl_3$): δ: 7.27 (d, J=6.1 Hz, 2H), 7.19-7.11 (m, 2H), 4.86 (q, J=6.5 Hz, 1H), 2.34 (s, 3H), 1.48 (d, J=6.4 Hz, 3H).

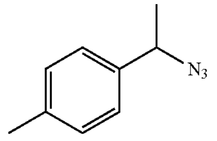

1-(1-azidoethyl)-4-methylbenzene (3k): The synthesis method of the intermediate 3i was performed using the intermediate 2k (1.00 g, 7.34 mmol), TFA (8.73 g, 73.42 mmol) and $NaN_3$ (1.91 g, 29.37 mmol) in DCM (80 mL) to obtain 3k in the form of a syrup (1.15 g, 97%). $^1$H NMR (400 MHz, $CDCl_3$): δ: 7.24-7.16 (m, 4H), 4.58 (q, J=6.8 Hz, 1H), 2.35 (s, 3H), 1.51 (d, J=6.8 Hz, 3H).

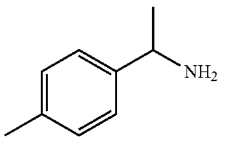

1-(p-tolyl)ethan-1-amine (4k): The synthesis method of the intermediate 4i was performed using 3k (1.10 g, 6.82 mmol) and $PPh_3$ (3.56 g, 13.65 mmol) in THF and then the reaction mixture was purified by flash column chromatography (DCM:MeOH=20:1) to obtain 4k in the form of a white solid (911 mg, 99%). $^1$H NMR (400 MHz, $CDCl_3$): δ: 7.30-7.22 (m, 2H), 7.18-7.10 (m, 2H), 6.02 (s, 2H), 4.14 (q, J=6.7 Hz, 1H), 2.33 (s, 3H), 1.47 (d, J=6.7 Hz, 3H).

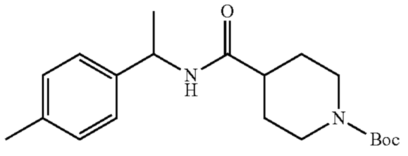 [SMILES: Cc1ccc(C(C)NC(=O)C2CCN(C(=O)OC(C)(C)C)CC2)cc1]

tert-butyl 4-((1-(p-tolyl)ethyl)carbamoyl)piperidine-1-carboxylate (b2k): The synthesis method of the intermediate b2a was performed using the intermediate b1 (1.42 g, 6.21 mmol), 4k (840 mg, 6.21 mmol), EDCI (1.43 g, 7.46 mmol), and DMAP (911 mg, 7.46 mmol) in DCM, and then the reaction mixture was purified by flash column chromatography (n-hexane:EtOAc=10:1) to obtain b2k in the form of a white solid (360 mg, 17%). $^1$H NMR (400 MHz, $CDCl_3$): δ: 7.21-7.11 (m, 4H), 5.60 (d, J=7.9 Hz, 1H), 5.09 (p, J=7.0 Hz, 1H), 2.72 (s, 2H), 2.33 (s, 3H), 2.19 (tt, J=11.6, 3.8 Hz, 1H), 1.69-1.59 (m, 2H), 1.46 (d, J=11.4 Hz, 12H).

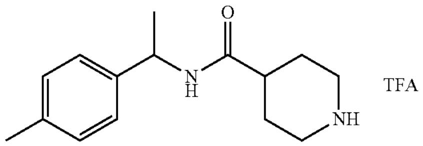 [SMILES: Cc1ccc(C(C)NC(=O)C2CCNCC2)cc1]

N-(1-(p-tolyl)ethyl)piperidine-4-carboxamide compound with 2,2,2-trifluoroacetaldehyde (1:1) (b3k): The synthesis method of the intermediate b3b was performed using b2k (340 mg, 0.98 mmol) and TFA (1.12 mg, 9.81 mmol) in DCM to obtain b3k in the form of a white solid (150 mg, quantitative yield). $^1$H NMR (400 MHz, DMSO-$d_6$): δ: 8.31 (d, J=8.0 Hz, 1H), 7.21-7.05 (m, 4H), 4.85 (p, J=7.1 Hz, 1H), 3.29-3.20 (m, 3H), 2.86 (tdd, J=12.4, 6.7, 3.2 Hz, 2H), 2.45 (ddd, J=11.1, 7.2, 3.9 Hz, 1H), 2.26 (s, 3H), 1.91-1.57 (m, 4H), 1.31 (d, J=7.0 Hz, 3H).

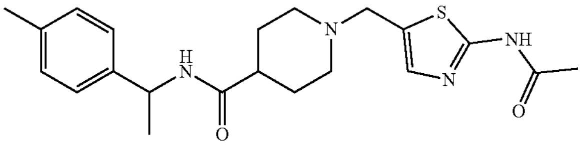 [SMILES: CC(=O)Nc1ncc(CN2CCC(C(=O)NC(C)c3ccc(C)cc3)CC2)s1]

1-((2-acetamidothiazol-5-yl)methyl)-N-(1-(p-tolyl)ethyl) piperidine-4-carboxamide (B-11): The synthesis method of the compound b-1 was performed using 2-acetamidothiazole (124 mg, 0.87 mmol), b3k (200 mg, 0.58 mmol), and paraformaldehyde (87 mg, 2.91 mmol) in acetic acid (20 mL) and then the reaction mixture was purified by flash column chromatography (DCM:MeOH=40:1) to obtain a compound B-11 in the form of oil (60 mg, 3%). $^1$H NMR (400 MHz, DMSO-$d_6$): δ: 11.93 (s, 1H), 8.12 (d, J=8.1 Hz, 1H), 7.23 (s, 1H), 7.17-7.07 (m, 4H), 4.84 (p, J=7.1 Hz, 1H), 3.59 (s, 2H), 2.25 (s, 3H), 2.11 (s, 4H), 1.97-1.86 (m, 2H), 1.67-1.44 (m, 4H), 1.29 (d, J=7.0 Hz, 3H).

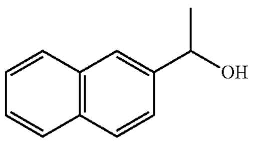

1-(naphthalen-2-yl)ethan-1-ol (2l): The synthesis method of the intermediate 2j was performed using 2'-acetonaphthone (2.00 g, 11.75 mmol) and $NaBH_4$ (445 mg, 11.75 mmol) in MeOH (50 mL) to obtain 2l in the form of a white solid (2.00 g, 99%). $^1$H NMR (400 MHz, $CDCl_3$): δ 7.83 (ddd, J=7.4, 4.9, 2.9 Hz, 4H), 7.56-7.40 (m, 3H), 5.08 (q, J=6.4 Hz, 1H), 1.59 (d, J=6.5 Hz, 3H).

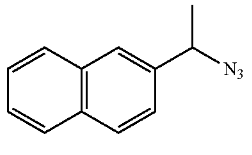

2-(1-azidoethyl)naphthalene (31): The synthesis method of the intermediate 3i was performed using 21 (2.00 mg, 11.51 mmol), TFA (13.24 g, 116.12 mmol), and $NaN_3$ (3.02g, 46.45 mmol) in DCM (80 mL) and then the reaction mixture was purified by flash column chromatography (DCM:MeOH=50:1) to obtain 31 in the form of a syrup (1.86 g, 81%). $^1$H NMR (400 MHz, $CDCl_3$): δ: 7.93-7.73 (m, 4H), 7.54-7.41 (m, 3H), 4.79 (q, J=6.8 Hz, 1H), 1.61 (d, J=6.8 Hz, 3H).

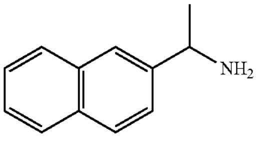

1-(naphthalen-2 yl)ethan-1-amine (41): The synthesis method of the intermediate 4i was performed using 31 (2.79 g, 14.14 mmol) and $PPh_3$ (7.42 g, 28.29 mmol) in THF and then the reaction mixture was purified by flash column chromatography (DCM:MeOH=40:1) to obtain 41 in the form of a white solid (1.21 mg, 50%). $^1$H NMR (400 MHz, $CDCl_3$): δ 7.82-7.73 (m, 4H), 7.52-7.41 (m, 3H), 5.99 (s, 2H), 4.34 (q, J=6.7 Hz, 1H), 1.56 (s, 3H).

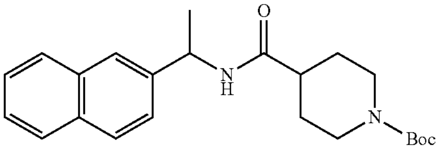 [SMILES: CC(NC(=O)C1CCN(C(=O)OC(C)(C)C)CC1)c1ccc2ccccc2c1]

tert-butyl 4-((1-(naphthalen-2-yl)ethyl)carbamoyl)piperidine-1-carboxylate (b21): The synthesis method of the intermediate b2a was performed using the intermediate b1 (3.21 g, 14.02 mmol), 41 (2.40 g, 14.02 mmol), EDCI (3.22 g, 16.82 mmol), and DMAP (2.05 g, 16.82 mmol) in DCM, and then the reaction mixture was purified by flash column chromatography (n-hexane:EtOAc=10:1) to obtain b21 in the form of a white solid (140 mg, 3%). $^1$H NMR (400 MHz, $CDCl_3$): δ: 7.85-7.70 (m, 4H), 7.52-7.37 (m, 3H), 5.73 (d, J=8.0 Hz, 1H), 5.30 (p, J=7.1 Hz, 1H), 4.13 (s, 2H), 2.24 (tt, J=11.6, 3.7 Hz, 1H), 1.82 (t, J=12.9 Hz, 2H), 1.66 (qd, J=13.0, 12.6, 4.4 Hz, 2H), 1.59 (d, J=4.5 Hz, 3H), 1.45 (s, 9H).

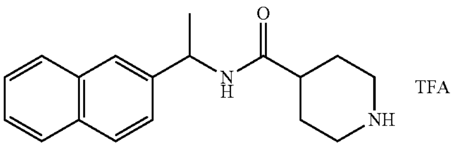 [SMILES: CC(NC(=O)C1CCNCC1)c1ccc2ccccc2c1]

N-(1-(naphthalen-2 yl)ethyl)piperidine-4-carboxamide compound with 2,2,2-trifluoroacetaldehyde (1:1) (b31): The synthesis method of the intermediate b3b was performed using 180D (140 mg, 0.37 mmol) and TFA (417 mg, 3.66 mmol) in DCM to obtain an intermediate b31 in the form of a white solid (130 mg, 94%). $^1$H NMR (500 MHz, DMSO-$d_6$): δ: 8.58 (s, 1H), 8.51 (d, J=7.9 Hz, 1H), 8.29 (s, 1H), 7.86 (dt, J=7.3, 2.8 Hz, 3H), 7.75 (s, 1H), 7.53-7.41 (m, 3H), 5.04 (p, J=7.2 Hz, 1H), 3.28 (t, J=14.9 Hz, 2H), 2.94-2.82 (m, 2H), 1.85 (d, J=11.5 Hz, 2H), 1.78-1.59 (m, 3H), 1.43 (d, J=7.1 Hz, 3H).

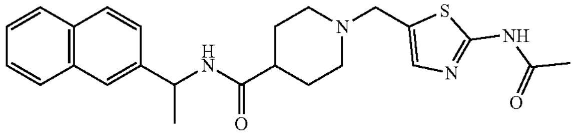 [SMILES: CC(=O)Nc1ncc(CN2CCC(C(=O)NC(C)c3ccc4ccccc4c3)CC2)s1]

1-((2-acetamidothiazol-5 yl)methyl)-N-(1-(naphthalen-2-yl)ethyl)piperidine-4-carboxamide (B-12): The synthesis method of the compound b-1 was performed using 2-acetamidothiazole (73 mg, 0.51 mmol), b31 (130 mg, 0.34 mmol), and paraformaldehyde (51 mg, 1.71 mmol) in acetic acid (20 mL) and then the reaction mixture was purified by flash column chromatography (DCM:MeOH=50:1) to obtain a compound B-12 in the form of a white solid (75 mg, 50%). $^1$H NMR (400 MHz, $CDCl_3$) δ: 11.28 (s, 1H), 7.85-7.71 (m, 4H), 7.51-7.38 (m, 3H), 7.20 (s, 1H), 5.79 (s, 1H), 5.35-5.24 (m, 1H), 3.70 (s, 2H), 3.00 (s, 2H), 2.28 (s, 3H), 1.58 (d, J=6.9 Hz, 3H).

Scheme 7. Synthesis of SB-13 to B-19

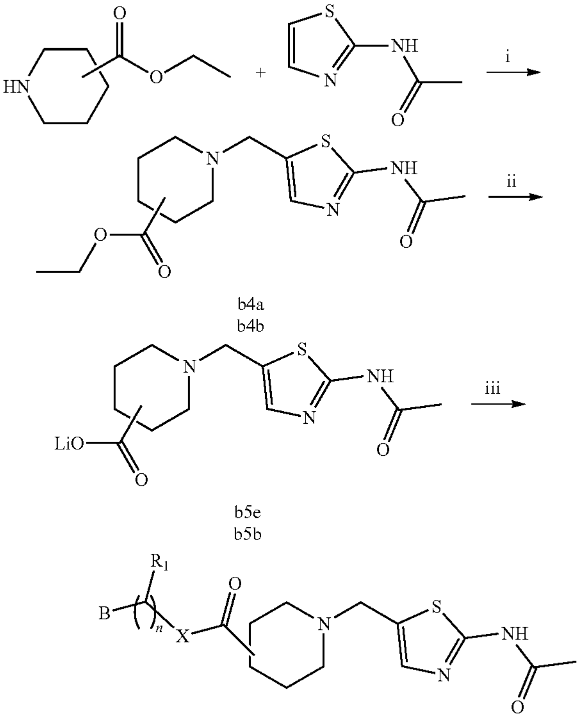

b4a
b4b b5e
b5b

B-13~B-19

Reagents and conditions: (i) paraformaldehyde, AcOH, 100° C., 4 h; (ii) lithium hydroxide anhydrous, THF:$H_2O$ (1:1), r.t., 1 d; (iii) amine compounds, EDCI, HOBt, DIPEA, DMF, 0° C.-r.t., overnight or amine compounds, EDCI, HOBt, DMF, 0° C.-r.t., overnight.

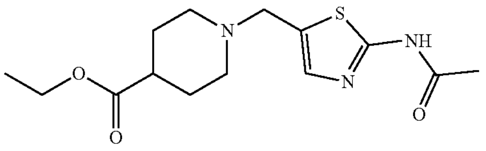 [SMILES: CCOC(=O)C1CCN(Cc2cnc(NC(C)=O)s2)CC1]

ethyl 1-((2-acetamidothiazol-5-yl)methyl)piperidine-4-carboxylate (b4a): Paraformaldehyde (382 mg, 12.72 mmol) was added to a solution of 2-acetamidothiazole (542 mg, 3.80 mmol) and ethyl 4-piperidinecarboxylate (400 mg, 2.54 mmol) in acetic acid (20 mL) while stirring at 100° C. The reaction mixture was stirred at 100° C. for 1 hour. Acetic acid was evaporated in vacuum. The resulting residue was purified by column chromatography (DCM:MeOH=20:1) to obtain b4a in the form of a white solid (750 mg, 95%). $^1$H NMR (400 MHz, $CDCl_3$): δ:12.06 (s, 1H), 7.18 (s, 1H), 4.13 (q, J=7.1 Hz, 2H), 3.66 (d, J=1.0 Hz, 2H), 2.88 (dt, J=11.7, 3.8 Hz, 2H), 2.31 (s, 3H), 2.34-2.20 (m, 1H), 2.15-2.04 (m, 2H), 1.89 (dd, J=13.4, 3.7 Hz, 2H), 1.84-1.70 (m, 2H), 1.25 (t, J=7.1 Hz, 3H).

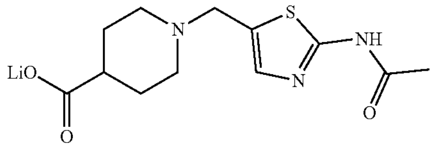

lithium 1-((2-acetamidothiazol-5-yl)methyl)piperidine-4-carboxylate (b5a): Lithium hydroxide (34 mg, 1.42 mmol) was added to a solution of an intermediate b4a in THF:$H_2O$ (1:1) at room temperature. The reaction mixture was stirred at 50° C. for 4 hours. The reaction mixture was diluted with EtOAc and the water layer was separated and evaporated in vacuum to obtain crude b5a without further purification. $^1$H NMR (400 MHz, DMSO-$d_6$): δ: 7.13 (s, 1H), 2.73 (dt, J=11.2, 3.7 Hz, 2H), 2.06 (s, 3H), 1.88 (td, J=11.4, 2.7 Hz, 2H), 1.79-1.64 (m, 3H), 1.46 (qd, J=11.8, 3.7 Hz, 2H).

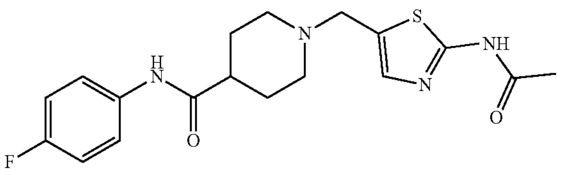 [SMILES: CC(=O)Nc1ncc(CN2CCC(C(=O)Nc3ccc(F)cc3)CC2)s1]

1-((2-acetamidothiazol-5-yl)methyl)-N-(4-fluorophenyl)piperidine-4-carboxamide (B-14): EDCI (280 mg, 1.46 mmol), HOBt (198 mg, 1.46 mmol) and DIPEA (393 mg, 3.04 mmol) were added to a solution of 4-fluoroaniline (135 mg, 1.22 mmol) and the intermediate b5a (233 mg, 1.22 mmol) in DMF (30 mL) at 0° C. The reaction mixture was stirred overnight at room temperature. The reaction mixture was added with ice water and extracted with EtOAc. The EtOAc layer was washed with saturated brine, dried over $Na_2SO_4$, and filtered and evaporated in vacuum. The filtrate was purified by flash column chromatography (n-hexane: EtOAc=3:1) to obtain a compound COA-0159 in the form of a white solid (58 mg, 13%). Mp: 254-256° C. $^1$H NMR (400 MHz, DMSO-$d_6$): δ: 11.86 (bs, 1H), 9.89 (s, 1H), 7.64-7.56 (m, 2H), 7.25 (s, 1H), 7.16-7.07 (m, 2H), 3.64-3.61 (m, 2H), 2.89 (d, J=11.1 Hz, 2H), 2.34-2.23 (m, 1H), 2.12 (s, 3H), 2.01-1.93 (m, 2H), 1.75 (d, J=11.9 Hz, 2H), 1.64 (tt, J=12.5, 6.2 Hz, 2H).

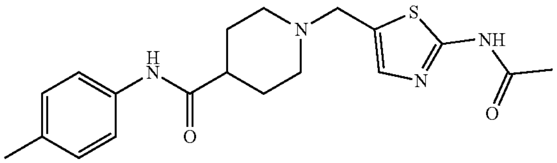 [SMILES: CC(=O)Nc1ncc(CN2CCC(C(=O)Nc3ccc(C)cc3)CC2)s1]

1-((2-acetamidothiazol-5-yl)methyl)-N-(p-tolyl)piperidine-4-carboxamide (B-15): The synthesis method of the compound B-14 was performed using p-toluidine (74 mg, 0.69 mmol), b5a (200 mg, 0.69 mmol), EDCI (159 mg, 0.83 mmol), HOBt (113 mg, 0.83 mmol), and DIPEA (223 mg, 1.73 mmol) in DMF (30 mL) and then the reaction mixture was purified by flash column chromatography (DCM: MeOH=40:1) to obtain a compound B-15 in the form of a white solid (28 mg, 11%). Mp: 262-264° C. $^1$H NMR (400 MHz, DMSO-$d_6$): δ: 11.93 (s, 1H), 9.72 (s, 1H), 7.49-7.44 (m, 2H), 7.25 (s, 1H), 7.10-7.05 (m, 2H), 3.62 (s, 2H), 2.89 (dd, J=7.7, 3.9 Hz, 2H), 2.34-2.26 (m, 1H), 2.23 (s, 3H), 2.12 (s, 3H), 2.02-1.90 (m, 2H), 1.77-1.58 (m, 4H).

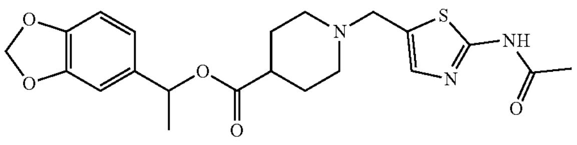 [SMILES: CC(=O)Nc1ncc(CN2CCC(C(=O)OC(C)c3ccc4c(c3)OCO4)CC2)s1]

1-(benzo[d][1,3]dioxol-5 yl)ethyl 1-((2-acetamidothiazol-5-yl)methyl)piperidine-4-carboxylate (B-13): The synthesis method of the compound B-14 was performed using the intermediate b5a (400 mg, 1.38 mmol), 2i (230 mg, 1.38 mmol), EDCI (318 mg, 1.66 mmol), and HOBt (225 mg, 1.66 mmol) in DMF, and then the reaction mixture was purified by flash column chromatography (DCM: MeOH=50:1) to obtain a compound B-13 in the form of a white solid (50 mg, 8%). Mp: 215-217° C. $^1$H NMR (400 MHz, DMSO-$d_6$): δ: 11.93 (s, 1H), 7.23 (s, 1H), 6.93-6.79 (m, 3H), 6.00 (d, J=5.5 Hz, 2H), 5.72 (dt, J=13.1, 6.7 Hz, 1H), 3.59 (s, 2H), 2.77 (dd, J=10.2, 5.2 Hz, 2H), 2.30 (ddt, J=10.7, 7.7, 3.8 Hz, 1H), 2.11 (s, 3H), 2.02 (dt, J=11.5, 3.1 Hz, 2H), 1.78 (dd, J=11.6, 7.2 Hz, 2H), 1.54 (tdd, J=13.2, 8.7, 3.4 Hz, 2H), 1.41 (d, J=6.5 Hz, 3H).

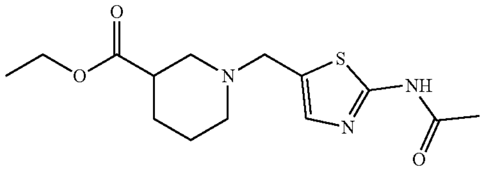 [SMILES: CCOC(=O)C1CCCN(Cc2cnc(NC(C)=O)s2)C1]

ethyl 1-((2-acetamidothiazol-5-yl)methyl)piperidine-3-carboxylate (b4b): The synthesis method of the intermediate b4a was performed using 2-acetamidothiazole (1.15 g, 8.11 mmol), ethyl nipecotate (850 mg, 5.41 mmol), and paraformaldehyde (811 mg, 27.03 mmol) in acetic acid (50 mL) and then the reaction mixture was purified by flash column chromatography (DCM:MeOH=30:1) to obtain an intermediate b4b in the form of a white solid (1.01 mg, 60%). $^1$H NMR (400 MHz, $CDCl_3$): δ: 7.13 (s, 1H), 4.12 (q, J=7.2, 2H), 3.67 (t, J=1.0 Hz, 2H), 2.97 (d, J=10.1 Hz, 1H), 2.77 (d, J=11.1 Hz, 1H), 2.57 (tt, J=10.4, 3.8 Hz, 1H), 2.27 (s, 3H), 2.23 (t, J=10.4 Hz, 1H), 2.09-2.04 (m, 1H), 1.98-1.88 (m, 1H), 1.72 (dt, J=13.0, 3.7 Hz, 1H), 1.43 (qd, J=11.7, 3.9 Hz, 1H), 1.23 (t, J=7.1 Hz, 3H).

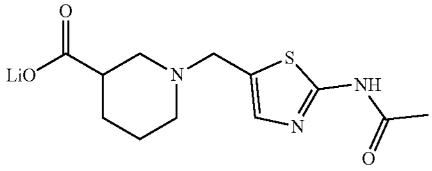

lithium 1-((2-acetamidothiazol-5-yl)methyl)piperidine-3-carboxylate (b5b): The synthesis method of the intermediate b5a was performed using b4b (200 mg, 0.64 mmol) and lithium hydroxide (34 mg, 1.41 mmol) in THF: $H_2O$ (1:1), and then a crude compound b5b was obtained without further purification. $^1$H NMR (400 MHz, DMSO-$d_6$): δ: 7.03 (s, 1H), 2.93 (dd, J=11.2, 3.7 Hz, 1H), 2.71 (d, J=10.6 Hz, 1H), 1.98 (s, 4H), 1.86-1.70 (m, 3H), 1.55 (dt, J=13.2, 3.5 Hz, 1H), 1.36 (tdt, J=12.7, 8.1, 4.0 Hz, 1H), 1.11 (qd, J=12.6, 3.9 Hz, 1H).

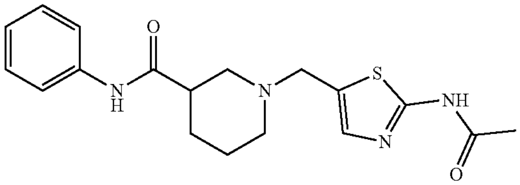 [SMILES: CC(=O)Nc1ncc(CN2CCCC(C(=O)Nc3ccccc3)C2)s1]

1-((2-acetamidothiazol-5-yl)methyl)-N-phenylpiperidine-3-carboxamide (B-16): The synthesis method of the compound B-14 was performed using the intermediate b5b (230 mg, 0.80 mmol), aniline (74 mg, 0.80 mmol), EDCI (183 mg, 0.95 mmol), and HOBt (129 mg, 0.95 mmol) in DMF, and then the reaction mixture was purified by flash column chromatography (DCM:MeOH=20:1) to obtain a compound B-16 in the form of a white solid (35 mg, 12%). Mp: 257-259° C. $^1$H NMR (400 MHz, DMSO-$d_6$): δ: 11.96 (s, 1H), 9.93 (s, 1H), 7.61-7.51 (m, 2H), 7.32-7.21 (m, 3H), 7.06-6.95 (m, 1H), 3.65 (s, 2H), 2.95-2.86 (m, 1H), 2.79 (d, J=11.2 Hz, 1H), 2.62-2.53 (m, 1H), 2.11 (s, 4H), 1.95 (t, J=10.3 Hz, 1H), 1.82 (d, J=12.3 Hz, 1H), 1.71-1.63 (m, 1H), 1.53-1.32 (m, 2H).

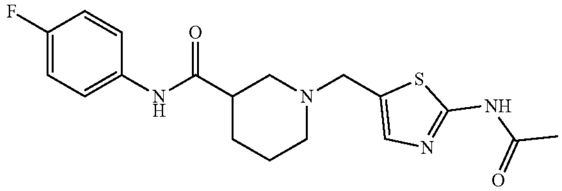 [SMILES: CC(=O)Nc1ncc(CN2CCCC(C(=O)Nc3ccc(F)cc3)C2)s1]

1-((2-acetamidothiazol-5-yl)methyl)-N-(4-fluorophenyl) piperidine-3-carboxamide (B-17): The synthesis method of the compound B-14 was performed using the intermediate b5b (200 mg, 0.69 mmol), 4-fluoroaniline (77 mg, 0.69 mmol), EDCI (159 mg, 0.83 mmol), and HOBt (113 mg, 0.83 mmol) in DMF, and then the reaction mixture was purified by flash column chromatography (DCM: MeOH=20:1) to obtain a compound B-17 in the form of a pink solid (40 mg, 15%). Mp: 127-129° C. $^1$H NMR (400 MHz, DMSO-$d_6$): δ: 11.96 (s, 1H), 9.99 (s, 1H), 7.64-7.53 (m, 2H), 7.26 (s, 1H), 7.17-7.05 (m, 2H), 3.65 (s, 2H), 2.95-2.86 (m, 1H), 2.79 (d, J=11.2 Hz, 1H), 2.53 (s, 1H), 2.11 (s, 4H), 2.02-1.90 (m, 1H), 1.81 (d, J=11.8 Hz, 1H), 1.73-1.64 (m, 1H), 1.52-1.33 (m, 2H).

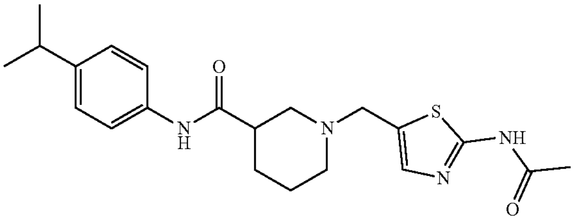 [SMILES: CC(=O)Nc1ncc(CN2CCCC(C(=O)Nc3ccc(C(C)C)cc3)C2)s1]

1-((2-acetamidothiazol-5-yl)methyl)-N-(4-isopropylphenyl)piperidine-3-carboxamide (B-18): The synthesis method of the compound B-14 was performed using the intermediate b5b (200 mg, 0.69 mmol), 4-isopropylaniline (93 mg, 0.69 mmol), EDCI (159 mg, 0.83 mmol), and HOBt (113 mg, 0.83 mmol) in DMF, and then the reaction mixture was purified by flash column chromatography (DCM: MeOH=20:1) to obtain a compound B-18 in the form of a white solid (80 mg, 29%). Mp: 234-236° C. $^1$H NMR (400 MHz, DMSO-$d_6$): δ: 11.96 (s, 1H), 9.85 (s, 1H), 7.52-7.41 (m, 2H), 7.26 (s, 1H), 7.17-7.09 (m, 2H), 3.65 (s, 2H), 2.93-2.75 (m, 3H), 2.59-2.52 (m, 1H), 2.11 (s, 4H), 1.99-1.91 (m, 1H), 1.80 (d, J=11.7 Hz, 1H), 1.67 (d, J=12.5 Hz, 1H), 1.52-1.35 (m, 2H), 1.16 (d, J=6.9 Hz, 6H).

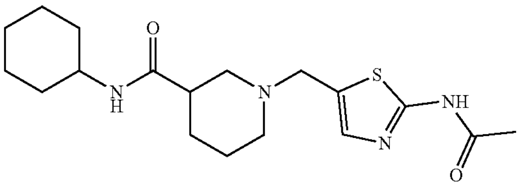 [SMILES: CC(=O)Nc1ncc(CN2CCCC(C(=O)NC3CCCCC3)C2)s1]

1-((2-acetamidothiazol-5 yl)methyl)-N-cyclohexylpiperidine-3-carboxamide (B-19): The synthesis method of the compound B-14 was performed using the intermediate b5b (200 mg, 0.69 mmol), cyclohexyl amine (69 mg, 0.69 mmol), EDCI (159 mg, 0.83 mmol), and HOBt (113 mg, 0.83 mmol) in DMF, and then the reaction mixture was purified by flash column chromatography (DCM: MeOH=20:1) to obtain a compound B-19 in the form of a white solid (25 mg, 7%). Mp: 265-267° C. $^1$H NMR (400 MHz, DMSO-$d_6$) δ 11.96 (s, 1H), 7.68 (d, J=7.9 Hz, 1H), 7.24 (s, 1H), 3.63-3.53 (m, 2H), 3.47 (s, 1H), 2.69 (d, J=10.6 Hz, 2H), 2.35-2.25 (m, 1H), 2.11 (s, 3H), 2.09-1.92 (m, 2H), 1.64 (dt, J=13.3, 3.5 Hz, 5H), 1.44-1.29 (m, 2H), 1.26-1.05 (m, 5H).

Example 3

Synthesis of Compound of Chemical Formula 4

A compound of Chemical Formula 4 below was prepared by the following process.

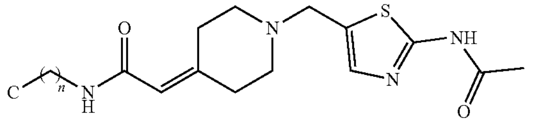 [SMILES: CCNC(=O)C=C1CCN(Cc2cnc(NC(C)=O)s2)CC1]

Scheme 8: Synthesis of C-1 to C-8

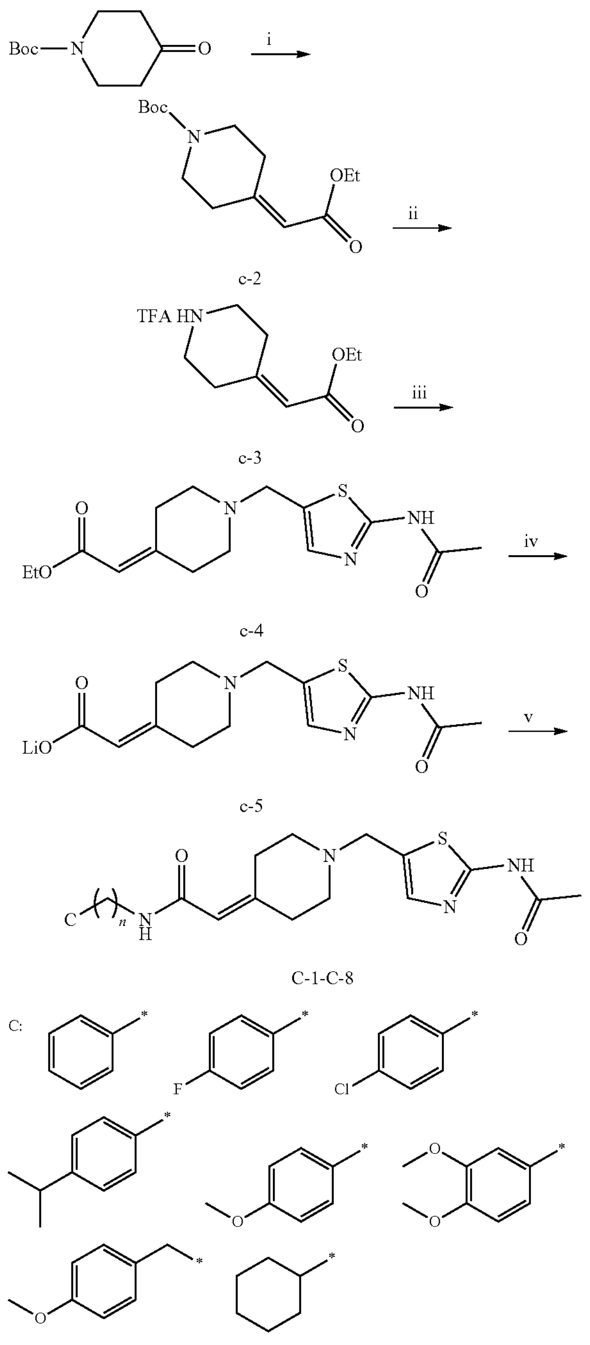

Reagents and conditions: (i) triethylphosphonoacetate, NaH, THF, 0° C.-r.t., overnight; (ii) TFA, DCM, r.t., overnight; (iii) 2-acetamidothiazole, paraformaldehyde, AcOH, 100° C., 1 h; (iv) lithium hydroxide, THF:$H_2O$ (1:1), r.t., 1 d; (v) amine compounds, EDCI, HOBt, DMF, 0° C.-r.t., overnight.

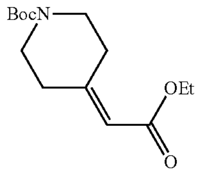 [SMILES: CCOC(=O)C=C1CCN(C(=O)OC(C)(C)C)CC1]

tert-butyl 4-(2-ethoxy-2-oxoethylidene)piperidine-1-carboxylate (c-2): Triethylphosphonoacetate (292 mg, 1.30 mmol) was added dropwise to a stirred solution of NaH (48 mg, 1.20 mmol) in THF (5 mL) at 0° C. After stirring at room temperature for 30 minutes, 1-boc-4-piperidone (200 mg, 1.00 mmol) in THF (2 mL) was added dropwise. The reaction mixture was stirred at room temperature overnight, and then diluted with $H_2O$ (5 mL) and extracted with EtOAc (2×5 mL). The bound organic layer was washed with brine (5 mL), dried over $Na_2SO_4$, filtered and concentrated. The crude residue was purified by flash column chromatography (n-hexane:EtOAc=10:1) to obtain a compound 1 in the form of a white solid (200 mg, 74%). $^1$H NMR (400 MHz, $CDCl_3$) δ: 5.71 (p, J=1.2 Hz, 1H), 4.16 (q, J=7.1 Hz, 2H), 3.49 (dt, J=11.4, 6.0 Hz, 4H), 2.97-2.89 (m, 2H), 2.28 (t, J=5.7 Hz, 2H), 1.47 (s, 9H), 1.28 (t, J=7.2 Hz, 3H).

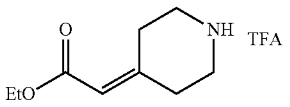 [SMILES: CCOC(=O)C=C1CCNCC1]

ethyl 2-(piperidin-4-ylidene)acetate compound with 2,2,2-trifluoroacetaldehyde (1:1) (c-3): TFA (974 mg, 8.54 mmol) was added to a stirred solution of the compound c-2 (230 mg, 1.00 mmol) in DCM (30 mL) at room temperature and the reaction mixture was stirred at room temperature for 4 hours. DCM was evaporated in vacuum to obtain a compound c-2 in the form of a white solid (quantitative yield). $^1$H NMR (400 MHz, DMSO-$d_6$): δ: 8.89 (s, 2H), 5.85 (t, J=1.3 Hz, 1H), 4.10 (q, J=7.1 Hz, 2H), 3.05 (t, J=6.3 Hz, 2H), 1.20 (t, J=7.1 Hz, 3H).

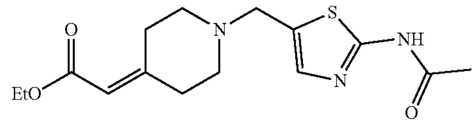

ethyl 2-(1-((2-acetamidothiazol-5-yl)methyl)piperidin-4-ylidene)acetate (c-4): Paraformaldehyde was added to a stirred solution of the compound c-3 (235 mg, 0.88 mmol) and 2-acetamidothiazole (188 mg, 1.32 mmol) in acetic acid (20 mL) at room temperature. The reaction mixture was stirred at 100° C. for 1 hour. Acetic acid was evaporated in vacuum. The resulting residue was purified by column chromatography (n-hexane:EtOAc=2:1) to obtain a compound c-3 in the form of a light yellow solid (200 mg, 70%). $^1$H NMR (400 MHz, $CDCl_3$) δ: 11.74 (s, 1H), 7.31 (s, 1H), 5.69 (s, 1H), 4.15 (q, J=7.1 Hz, 2H), 3.92 (s, 2H), 3.09 (s, 3H), 2.76 (s, 3H), 2.45 (s, 2H), 2.31 (s, 3H), 1.27 (t, J=7.2 Hz, 3H).

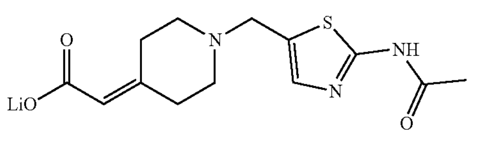

lithium 2-(1-((2-acetamidothiazol-5-yl)methyl)piperidin-4-ylidene)acetate (c-5): Lithium hydroxide anhydrous (5 Ml, 8.66 mmol) was added to a stirred solution of the compound c-4 (280 mg, 0.87 mmol) in THF: $H_2O$ (1:1) at room temperature. The reaction mixture was stirred at room temperature for 1 hour. The reaction mixture was diluted with EtOAc and the water layer was separated. The water was evaporated in vacuum to obtain a compound c-4. $^1H$ NMR (400 MHz, DMSO-$d_6$): δ: 5.50 (s, 1H), 3.57 (s, 2H), 2.87 (s, 2H), 2.38 (dt, J=18.7, 5.6 Hz, 4H), 2.10 (t, J=5.5 Hz, 2H), 2.05 (s, 3H).

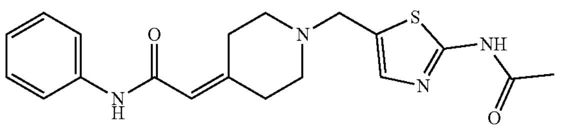 [SMILES: CC(=O)Nc1ncc(CN2CCC(=CC(=O)Nc3ccccc3)CC2)s1]

2-(1-((2-acetamidothiazol-5-yl)methyl)piperidin-4-ylidene)-N-phenylacetamide (C-1): The synthesis method of the compound B-14 was performed using the intermediate c-5 (324 mg, 1.07 mmol), aniline (200 mg, 2.15 mmol), EDCI (494 mg, 2.58 mmol), and HOBt (350 mg, 2.58 mmol) in DMF, and then the reaction mixture was purified by flash column chromatography (DCM:MeOH=50:1) to obtain a compound C-1 in the form of a white solid (24 mg, 6%). Mp: 184-185° C. $^1H$ NMR (400 MHz, $CDCl_3$) δ: 12.07 (s, 1H), 7.56-7.49 (m, 2H), 7.32 (td, J=7.8, 5.5 Hz, 2H), 7.24-7.06 (m, 3H), 5.69 (s, 1H), 3.74 (d, J=32.0 Hz, 2H), 3.10 (s, 1H), 3.06 (d, J=5.7 Hz, 1H), 2.68-2.54 (m, 4H), 2.36-2.31 (m, 4H), 2.23 (s, 1H).

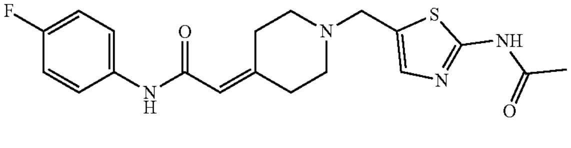 [SMILES: CC(=O)Nc1ncc(CN2CCC(=CC(=O)Nc3ccc(F)cc3)CC2)s1]

2-(1-((2-acetamidothiazol-5-yl)methyl)piperidin-4-ylidene)-N-(4-fluorophenyl)acetamide (C-2): The synthesis method of the compound B-14 was performed using the intermediate c-5 (542 mg, 1.80 mmol), 4-fluoroaniline (200 mg, 1.80 mmol), EDCI (414 mg, 2.16 mmol), and HOBt (293 mg, 2.16 mmol) in DMF, and then the reaction mixture was purified by flash column chromatography (DCM: MeOH=20:1) to obtain a compound C-2 in the form of a white solid (50 mg, 4%). Mp: 189-191° C. $^1H$ NMR (400 MHz, DMSO-$d_6$): δ: 11.97 (s, 1H), 9.97 (s, 1H), 7.70-7.52 (m, 2H), 7.26 (d, J=0.9 Hz, 1H), 7.12 (ddt, J=8.9, 6.8, 1.8 Hz, 2H), 5.82 (s, 1H), 3.74-3.58 (m, 2H), 2.95 (dd, J=14.6, 9.1 Hz, 3H), 2.45 (t, J=5.7 Hz, 2H), 2.27 (t, J=5.6 Hz, 2H), 2.11 (d, J=3.0 Hz, 4H).

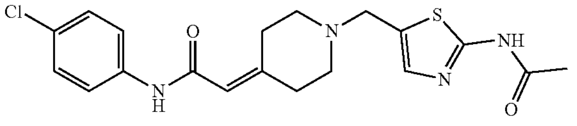

2-(1-((2-acetamidothiazol-5-yl)methyl)piperidin-4-ylidene)-N-(4-chlorophenyl)acetamide (C-3): The synthesis method of the compound B-14 was performed using the intermediate c-5 (472 mg, 1.57 mmol), 4-chloroaniline (200 mg, 1.57 mmol), EDCI (361 mg, 1.88 mmol), and HOBt (255 mg, 1.88 mmol) in DMF, and then the reaction mixture was purified by flash column chromatography (DCM: MeOH=20:1) to obtain a compound C-3 in the form of a white solid (32 mg, 5%). Mp: 225-228° C. $^1H$ NMR (500 MHz, DMSO-$d_6$): δ: 11.97 (s, 1H), 10.07 (d, J=20.5 Hz, 1H), 7.65-7.57 (m, 2H), 7.36-7.30 (m, 2H), 7.25 (s, 1H), 5.82 (s, 1H), 3.66 (d, J=5.9 Hz, 2H), 3.02-2.85 (m, 4H), 2.27 (d, J=5.9 Hz, 1H), 2.45 (s, 1H), 2.10 (t, J=7.1 Hz, 5H).

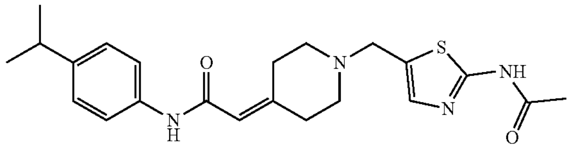 [SMILES: CC(=O)Nc1ncc(CN2CCC(=CC(=O)Nc3ccc(C(C)C)cc3)CC2)s1]

2-(1-((2-acetamidothiazol-5-yl)methyl)piperidin-4-ylidene)-N-(4-isopropylphenyl)acetamide (C-4): The synthesis method of the compound B-14 was performed using the intermediate c-5 (446 mg, 1.48 mmol), 4-isopropylaniline (200 mg, 1.48 mmol), EDCI (340 mg, 1.78 mmol), and HOBt (241 mg, 1.78 mmol) in DMF, and then the reaction mixture was purified by flash column chromatography (DCM:MeOH=20:1) to obtain a compound C-4 in the form of a white solid (20 mg, 3%). Mp: 232-236° C. $^1H$ NMR (500 MHz, DMSO-$d_6$) δ:11.93 (s, 1H), 9.81 (d, J=16.0 Hz, 1H), 7.49 (dd, J=15.3, 8.2 Hz, 2H), 7.25 (s, 1H), 7.19-7.08 (m, 2H), 5.82 (s, 1H), 3.66 (d, J=6.8 Hz, 2H), 2.93 (d, J=23.7 Hz, 3H), 2.82 (p, J=6.9 Hz, 1H), 2.45 (t, J=5.7 Hz, 2H), 2.25 (s, 2H), 2.11 (d, J=4.1 Hz, 4H), 1.16 (d, J=6.9 Hz, 6H).

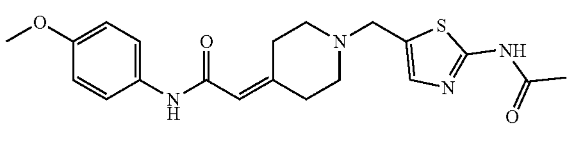 [SMILES: COc1ccc(NC(=O)C=C2CCN(Cc3cnc(NC(C)=O)s3)CC2)cc1]

2-(1-((2-acetamidothiazol-5-yl)methyl)piperidin-4 ylidene)-N-(4-methoxyphenyl)acetamide (C-5): The synthesis method of the compound B-14 was performed using the intermediate c-5 (489 mg, 1.62 mmol), 4-methoxylaniline (200 mg, 1.62 mmol), EDCI (374 mg, 1.95 mmol), and HOBt (264 mg, 1.95 mmol) in DMF, and then the reaction mixture was purified by flash column chromatography (DCM:MeOH=20:1) to obtain a compound C-5 in the form of a white solid (80 mg, 12%). Mp: 212-214° C. $^1H$ NMR (500 MHz, DMSO-$d_6$): δ: 11.96 (s, 1H), 9.76 (s, 1H), 7.51 (d, J=8.8 Hz, 2H), 7.25 (s, 1H), 6.85 (d, J=8.8 Hz, 2H), 5.79 (s, 1H), 3.70 (d, J=1.3 Hz, 3H), 3.65 (s, 2H), 3.16 (d, J=4.6 Hz, 1H), 2.95 (d, J=7.4 Hz, 3H), 2.44 (t, J=5.7 Hz, 2H), 2.24 (t, J=5.4 Hz, 2H), 2.11 (s, 3H).

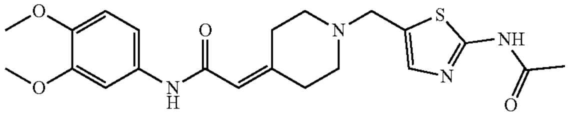 [SMILES: COc1ccc(NC(=O)C=C2CCN(Cc3cnc(NC(C)=O)s3)CC2)cc1OC]

2-(1-((2-acetamidothiazol-5-yl)methyl)piperidin-4-ylidene)-N-(3,4-dimethoxyphenyl)acetamide (C-6): The synthesis method of the compound B-14 was performed using the intermediate c-5 (393 mg, 1.31 mmol), 3,4-dimethoxylaniline (200 mg, 1.31 mmol), EDCI (300 mg, 1.57 mmol), and HOBt (213 mg, 1.57 mmol) in DMF, and then the reaction mixture was purified by flash column chromatography (DCM:MeOH=20:1) to obtain a compound C-6 in the form of a white solid (20 mg, 4%). Mp: 214-219° C. $^1$H NMR (500 MHz, DMSO-$d_6$): δ: 11.97 (s, 1H), 9.77 (s, 1H), 7.37 (d, J=2.3 Hz, 1H), 7.25 (s, 1H), 7.07 (dd, J=8.8, 2.3 Hz, 1H), 6.85 (d, J=8.7 Hz, 1H), 5.79 (s, 1H), 3.70 (d, J=3.8 Hz, 6H), 3.65 (s, 2H), 2.96 (s, 3H), 2.43 (d, J=6.2 Hz, 2H), 2.25 (s, 2H), 2.10 (d, J=3.8 Hz, 4H).

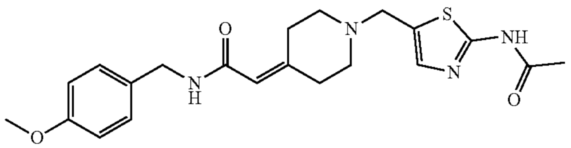 [SMILES: COc1ccc(CNC(=O)C=C2CCN(Cc3cnc(NC(C)=O)s3)CC2)cc1]

2-(1-((2-acetamidothiazol-5-yl)methyl)piperidin-4-ylidene)-N-(4-methoxybenzyl)acetamide (C-7): The synthesis method of the compound B-14 was performed using the intermediate c-5 (439 mg, 1.46 mmol), 4-methoxylbenzylamine (200 mg, 1.46 mmol), EDCI (335 mg, 1.75 mmol), and HOBt (237 mg, 1.75 mmol) in DMF, and then the reaction mixture was purified by flash column chromatography (DCM:MeOH=20:1) to obtain a compound C-7 in the form of a white solid (44 mg, 7%). Mp: 222-224° C. $^1$H NMR (500 MHz, DMSO-$d_6$): δ: 11.97 (s, 1H), 8.27 (t, J=6.0 Hz, 1H), 7.24 (s, 1H), 7.15 (d, J=8.5 Hz, 2H), 6.86 (d, J=8.5 Hz, 2H), 5.65 (s, 1H), 4.18 (d, J=5.9 Hz, 2H), 3.71 (s, 3H), 3.63 (s, 2H), 2.92 (s, 2H), 2.42 (dt, J=21.4, 5.8 Hz, 4H), 2.21-2.15 (m, 2H), 2.11 (s, 3H).

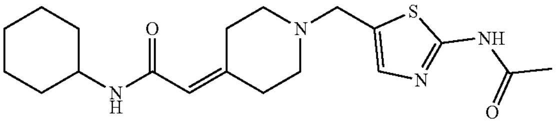 [SMILES: CC(=O)Nc1ncc(CN2CCC(=CC(=O)NC3CCCCC3)CC2)s1]

2-(1-((2-acetamidothiazol-5-yl)methyl)piperidin-4-ylidene)-N-cyclohexylacetamide (C-8): The synthesis method of the compound B-14 was performed using the intermediate c-5 (451 mg, 1.50 mmol), cyclohexyl amine (148 mg, 1.50 mmol), EDCI (345 mg, 1.80 mmol), and HOBt (244 mg, 1.80 mmol) in DMF, and then the reaction mixture was purified by flash column chromatography (DCM:MeOH=20:1) to obtain a compound C-8 in the form of a white solid (25 mg, 4%). Mp: 222-224° C. $^1$H NMR (500 MHz, DMSO-$d_6$): δ: 11.96 (s, 1H), 7.68 (d, J=7.9 Hz, 1H), 7.24 (s, 1H), 5.59 (s, 1H), 3.62 (s, 2H), 3.52 (d, J=9.7 Hz, 1H), 2.89 (s, 2H), 2.41 (dt, J=26.1, 5.7 Hz, 4H), 2.15 (t, J=5.7 Hz, 2H), 2.10 (s, 3H), 1.68 (t, J=17.3 Hz, 4H), 1.53 (d, J=12.7 Hz, 1H), 1.23 (q, J=12.5 Hz, 2H), 1.15-1.05 (m, 3H).

Example 4

Enzyme Activity Assay

Human OGA (recombinant hOGA protein, advanced Protein Technologies corp., Korea) enzyme reaction was performed in a reaction solution containing 25 mM Tris/HCl and 0.1 mg/ml bovine serum albumin (pH 7.5) using 2 mM 4-Methylumbelliferyl N-acetyl-β-D-glucosaminide (69585; Sigma) dissolved in DMSO as a substrate. The amount of the human OGA enzyme used in the reaction was 8 ng/well. Various amounts of the compounds of Examples 1 to 3 were added to the enzyme before the reaction started. The reaction was performed in a 384-well plate at 37° C. for 20 minutes, and then started by adding the substrate. An increase in fluorescence was measured using a SAFIRE (Tecan, Switzerland) fluorometer and detected at excitation and emission wavelengths set at 360 nm and 460 nm, respectively. The detected enzyme activity was shown in Table 1 below.

TABLE 1

| Code | Structure | % of inhibition | $IC_{50}$(μM) |
|---|---|---|---|
| A-1 | 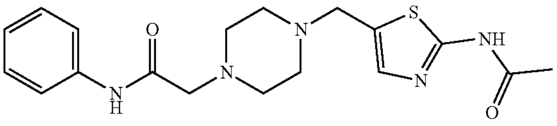 [SMILES: CC(=O)Nc1ncc(CN2CCN(CC(=O)Nc3ccccc3)CC2)s1] | 78.3 | 2.60 |
| A-2 | 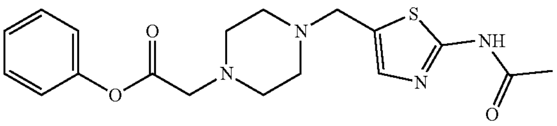 [SMILES: CC(=O)Nc1ncc(CN2CCN(CC(=O)Oc3ccccc3)CC2)s1] | 34.6 | N.D.[a] |
| A-3 | 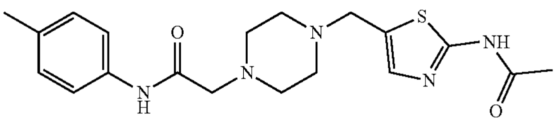 [SMILES: CC(=O)Nc1ncc(CN2CCN(CC(=O)Nc3ccc(C)cc3)CC2)s1] | 70.7 | N.D. |

TABLE 1-continued
| Code | Structure | % of inhibition | $IC_{50}$(μM) |
| --- | --- | --- | --- |
| A-4 | 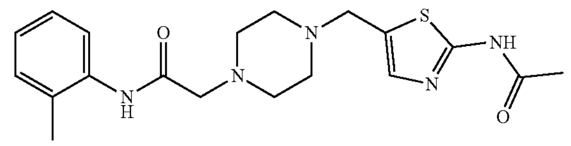 [SMILES: CC(=O)Nc1ncc(CN2CCN(CC(=O)Nc3ccccc3C)CC2)s1] | 47.6 | N.D. |
| A-5 | 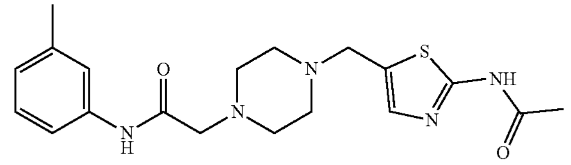 [SMILES: CC(=O)Nc1ncc(CN2CCN(CC(=O)Nc3cccc(C)c3)CC2)s1] | 62.4 | N.D. |
| A-6 | 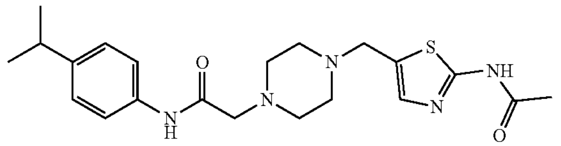 [SMILES: CC(=O)Nc1ncc(CN2CCN(CC(=O)Nc3ccc(C(C)C)cc3)CC2)s1] | 79.2 | N.D. |
| A-7 | 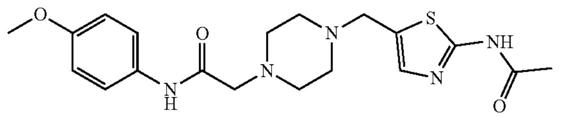 [SMILES: COc1ccc(NC(=O)CN2CCN(Cc3cnc(NC(C)=O)s3)CC2)cc1] | 84.2 | 0.84 |
| A-8 | 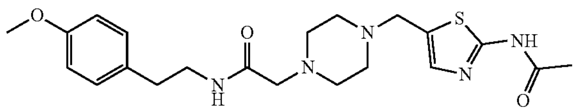 [SMILES: COc1ccc(CCNC(=O)CN2CCN(Cc3cnc(NC(C)=O)s3)CC2)cc1] | 85.4 | 0.63 |
| A-9 | 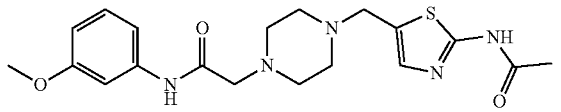 [SMILES: COc1cccc(NC(=O)CN2CCN(Cc3cnc(NC(C)=O)s3)CC2)c1] | 59.9 | N.D. |
| A-10 | 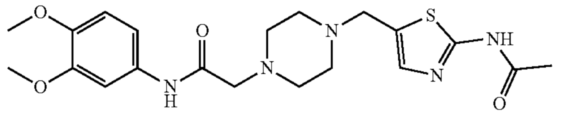 [SMILES: COc1ccc(NC(=O)CN2CCN(Cc3cnc(NC(C)=O)s3)CC2)cc1OC] | 62.4 | N.D. |
| A-11 | 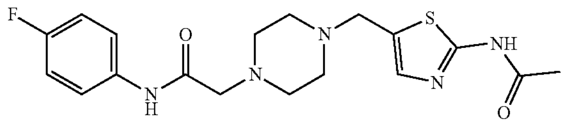 [SMILES: CC(=O)Nc1ncc(CN2CCN(CC(=O)Nc3ccc(F)cc3)CC2)s1] | 85.7 | 2.61 |
| A-12 | 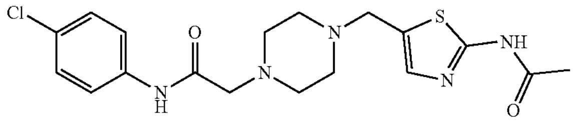 [SMILES: CC(=O)Nc1ncc(CN2CCN(CC(=O)Nc3ccc(Cl)cc3)CC2)s1] | 81.6 | 1.99 |
| A-13 | 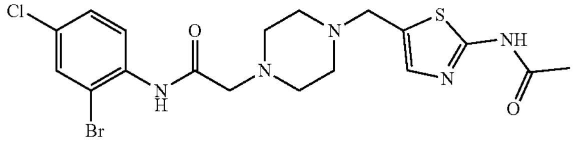 [SMILES: CC(=O)Nc1ncc(CN2CCN(CC(=O)Nc3ccc(Cl)cc3Br)CC2)s1] | 85.2 | 1.70 |
| A-14 | 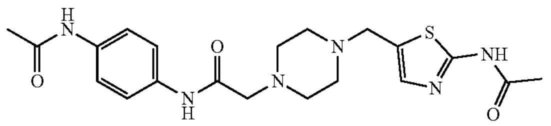 [SMILES: CC(=O)Nc1ccc(NC(=O)CN2CCN(Cc3cnc(NC(C)=O)s3)CC2)cc1] | 80.0 | 1.25 |

TABLE 1-continued
| Code | Structure | % of inhibition | IC$_{50}$(μM) |
|---|---|---|---|
| A-15 | 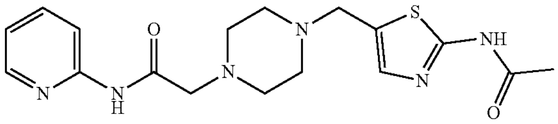 [SMILES: CC(=O)Nc1ncc(CN2CCN(CC(=O)Nc3ccccn3)CC2)s1] | 90.9 | 1.40 |
| A-16 | 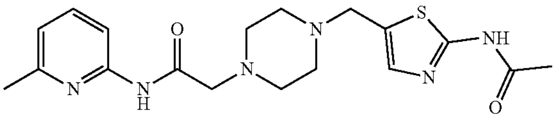 [SMILES: CC(=O)Nc1ncc(CN2CCN(CC(=O)Nc3cccc(C)n3)CC2)s1] | 38.6 | N.D |
| A-17 | 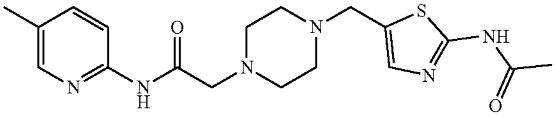 [SMILES: CC(=O)Nc1ncc(CN2CCN(CC(=O)Nc3ccc(C)cn3)CC2)s1] | 64.3 | N.D. |
| A-18 | 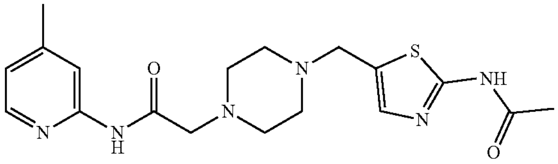 | 48.8 | N.D. |
| A-19 | 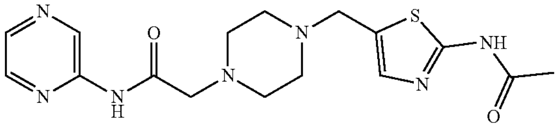 [SMILES: CC(=O)Nc1ncc(CN2CCN(CC(=O)Nc3cnccn3)CC2)s1] | 74.7 | N.D. |
| A-20 | 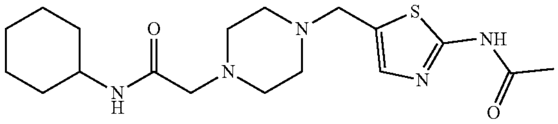 [SMILES: CC(=O)Nc1ncc(CN2CCN(CC(=O)NC3CCCCC3)CC2)s1] | 89.0 | 1.40 |
| A-21 | 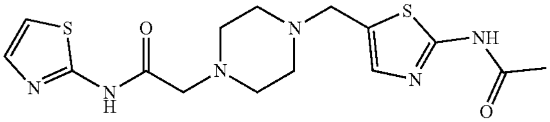 [SMILES: CC(=O)Nc1ncc(CN2CCN(CC(=O)Nc3nccs3)CC2)s1] | 59.1 | N.D. |
| A-22 | 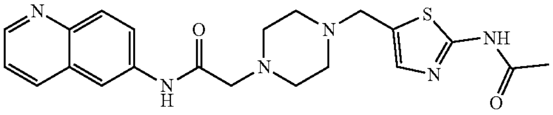 | 97.5 | 0.90 |
| A-23 | 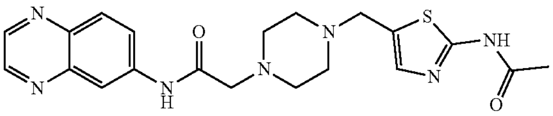 [SMILES: CC(=O)Nc1ncc(CN2CCN(CC(=O)Nc3ccc4nccnc4c3)CC2)s1] | 70.1 | N.D. |
| A-24 | 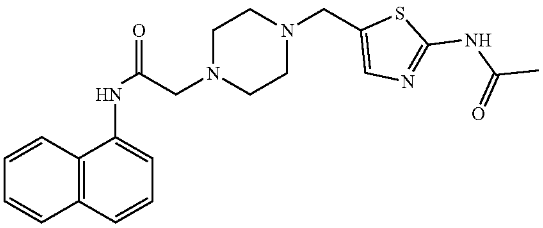 [SMILES: CC(=O)Nc1ncc(CN2CCN(CC(=O)Nc3cccc4ccccc34)CC2)s1] | 71.3 | N.D. |

TABLE 1-continued
| Code | Structure | % of inhibition | $IC_{50}$(μM) |
|---|---|---|---|
| A-25 | 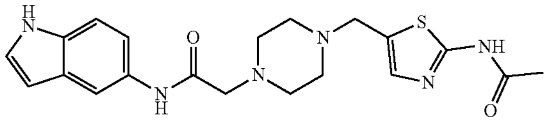 [SMILES: CC(=O)Nc1ncc(CN2CCN(CC(=O)Nc3ccc4[nH]ccc4c3)CC2)s1] | 59.2 | N.D. |
| A-26 | 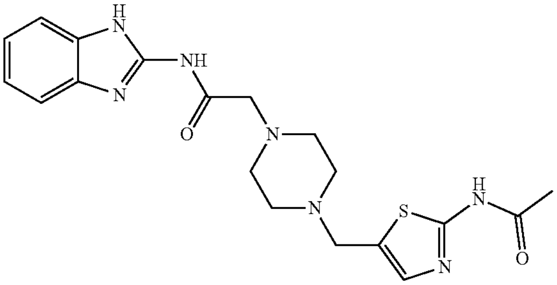 [SMILES: CC(=O)Nc1ncc(CN2CCN(CC(=O)Nc3nc4ccccc4[nH]3)CC2)s1] | 62.6 | N.D. |
| A-27 | 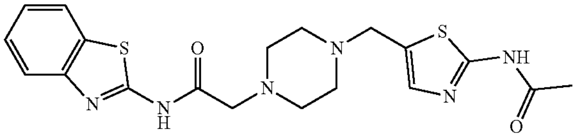 [SMILES: CC(=O)Nc1ncc(CN2CCN(CC(=O)Nc3nc4ccccc4s3)CC2)s1] | 46.2 | N.D. |
| A-28 | 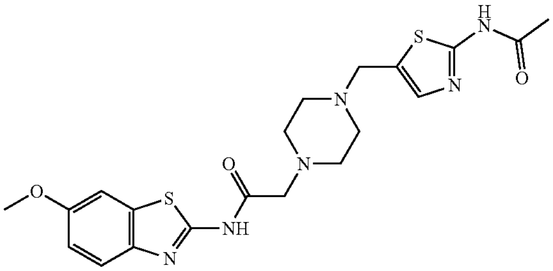 [SMILES: COc1ccc2nc(NC(=O)CN3CCN(Cc4cnc(NC(C)=O)s4)CC3)sc2c1] | 19.2 | N.D. |
| A-29 | 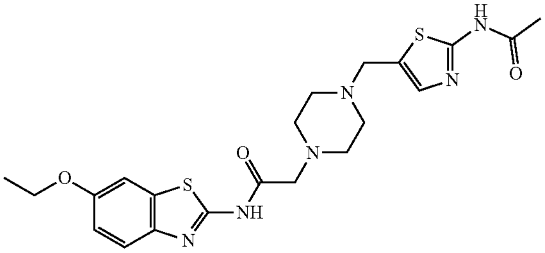 [SMILES: CCOc1ccc2nc(NC(=O)CN3CCN(Cc4cnc(NC(C)=O)s4)CC3)sc2c1] | 44.6 | N.D. |
| A-30 | 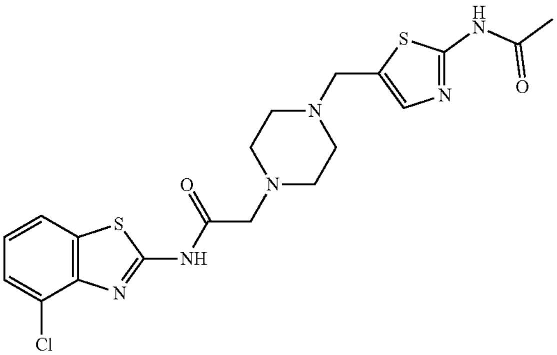 [SMILES: CC(=O)Nc1ncc(CN2CCN(CC(=O)Nc3nc4c(Cl)cccc4s3)CC2)s1] | 42.6 | N.D. |

TABLE 1-continued
| Code | Structure | % of inhibition | $IC_{50}$(μM) |
|---|---|---|---|
| A-31 | 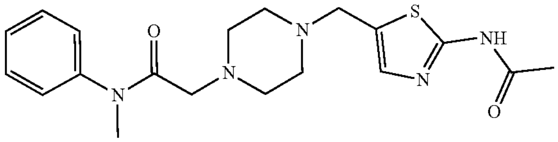 [SMILES: CC(=O)Nc1ncc(CN2CCN(CC(=O)N(C)c3ccccc3)CC2)s1] | 50.4 | N.D. |
| A-32 | 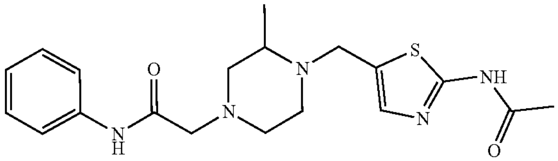 [SMILES: CC(=O)Nc1ncc(CN2CCN(CC(=O)Nc3ccccc3)CC2C)s1] | 97.0 | 0.24 |
| A-33 | 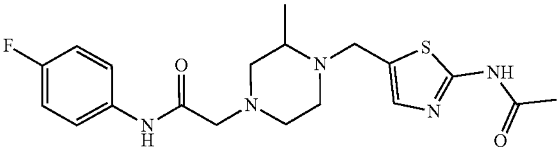 [SMILES: CC(=O)Nc1ncc(CN2CCN(CC(=O)Nc3ccc(F)cc3)CC2C)s1] | 97.9 | 0.23 |
| A-34 | 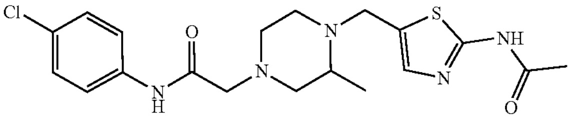 [SMILES: CC(=O)Nc1ncc(CN2CCN(CC(=O)Nc3ccc(Cl)cc3)CC2C)s1] | 98.4 | 0.05 |
| A-35 | 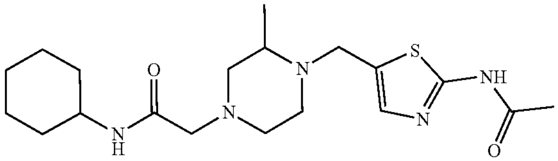 [SMILES: CC(=O)Nc1ncc(CN2CCN(CC(=O)NC3CCCCC3)CC2C)s1] | 98.4 | 0.10 |
| A-36 | 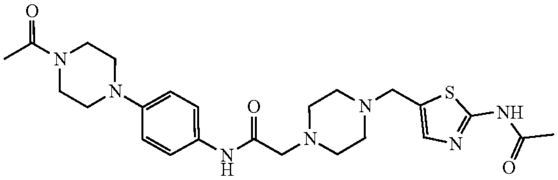 [SMILES: CC(=O)Nc1ncc(CN2CCN(CC(=O)Nc3ccc(N4CCN(C(C)=O)CC4)cc3)CC2)s1] | 96.2 | 1.04 |
| A-37 | 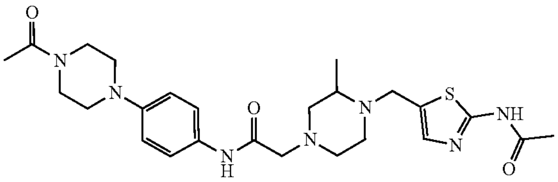 [SMILES: CC(=O)Nc1ncc(CN2CCN(CC(=O)Nc3ccc(N4CCN(C(C)=O)CC4)cc3)CC2C)s1] | 98.4 | 0.07 |
| A-38 | 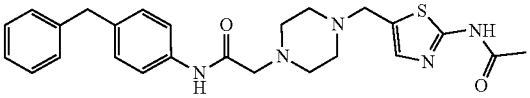 [SMILES: CC(=O)Nc1ncc(CN2CCN(CC(=O)Nc3ccc(Cc4ccccc4)cc3)CC2)s1] | 90.8 | 0.37 |
| A-39 | 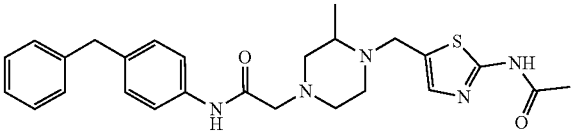 [SMILES: CC(=O)Nc1ncc(CN2CCN(CC(=O)Nc3ccc(Cc4ccccc4)cc3)CC2C)s1] | 98.8 | 0.06 |

TABLE 1-continued
| Code | Structure | % of inhibition | IC50(μM) |
|---|---|---|---|
| A-40 | 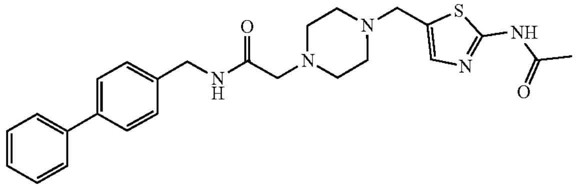 [SMILES: CC(=O)Nc1ncc(CN2CCN(CC(=O)NCc3ccc(-c4ccccc4)cc3)CC2)s1] | 97.7 | 0.21 |
| A-41 | 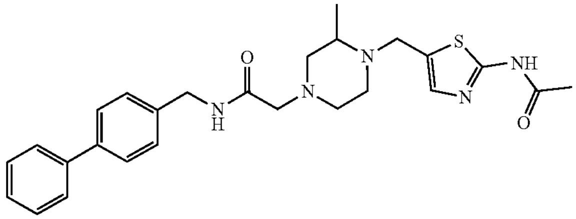 [SMILES: CC(=O)Nc1ncc(CN2CCN(CC(=O)NCc3ccc(-c4ccccc4)cc3)CC2C)s1] | 99.6 | 0.03 |
| B-1 | 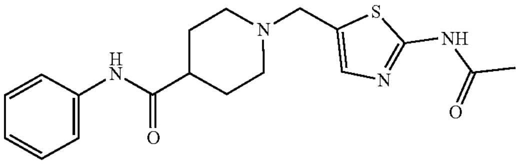 [SMILES: CC(=O)Nc1ncc(CN2CCC(C(=O)Nc3ccccc3)CC2)s1] | 87.0 | 0.87 |
| B-2 | 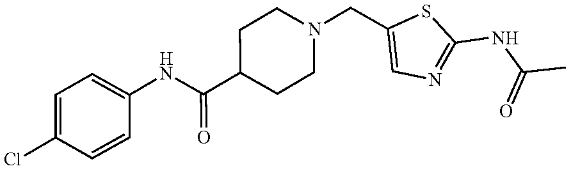 [SMILES: CC(=O)Nc1ncc(CN2CCC(C(=O)Nc3ccc(Cl)cc3)CC2)s1] | 91.0 | 0.27 |
| B-3 | 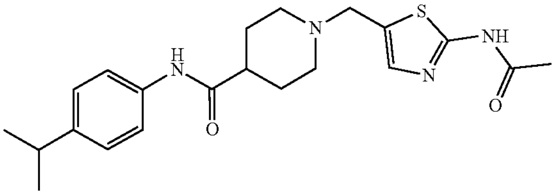 [SMILES: CC(=O)Nc1ncc(CN2CCC(C(=O)Nc3ccc(C(C)C)cc3)CC2)s1] | 91.8 | 0.68 |
| B-4 | 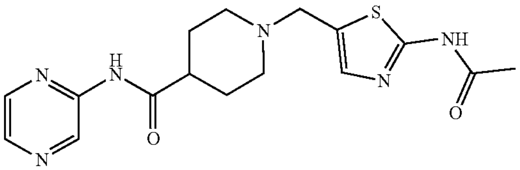 [SMILES: CC(=O)Nc1ncc(CN2CCC(C(=O)Nc3cnccn3)CC2)s1] | 66.9 | N.D. |
| B-5 | 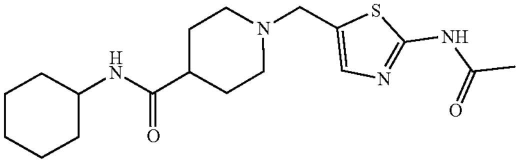 [SMILES: CC(=O)Nc1ncc(CN2CCC(C(=O)NC3CCCCC3)CC2)s1] | 46.7 | N.D. |
| B-6 | 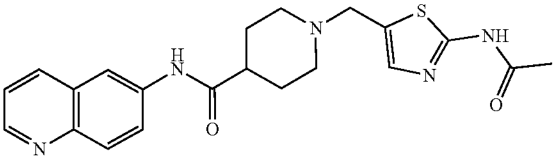 [SMILES: CC(=O)Nc1ncc(CN2CCC(C(=O)Nc3ccc4ncccc4c3)CC2)s1] | 91.4 | 0.32 |

TABLE 1-continued
| Code | Structure | % of inhibition | $IC_{50}$(μM) |
|---|---|---|---|
| B-7 | 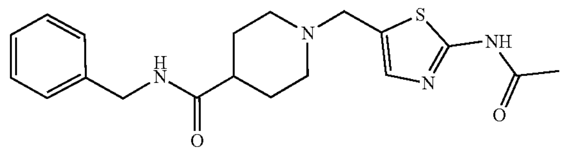 [SMILES: CC(=O)Nc1ncc(CN2CCC(C(=O)NCc3ccccc3)CC2)s1] | 88.2 | 1.00 |
| B-8 | 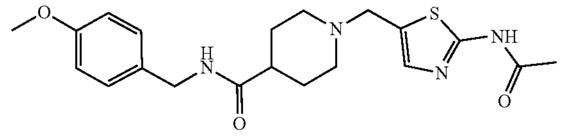 [SMILES: COc1ccc(CNC(=O)C2CCN(Cc3cnc(NC(C)=O)s3)CC2)cc1] | 93.9 | 0.86 |
| B-9 | 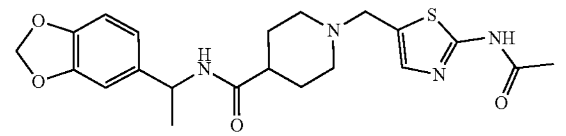 [SMILES: CC(=O)Nc1ncc(CN2CCC(C(=O)NC(C)c3ccc4c(c3)OCO4)CC2)s1] | 93.1 | 1.01 |
| B-10 | 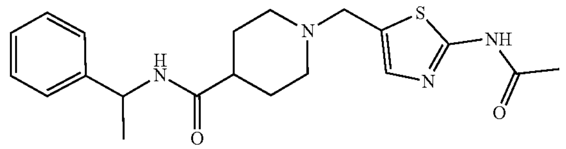 [SMILES: CC(=O)Nc1ncc(CN2CCC(C(=O)NC(C)c3ccccc3)CC2)s1] | 93.3 | 0.90 |
| B-11 | 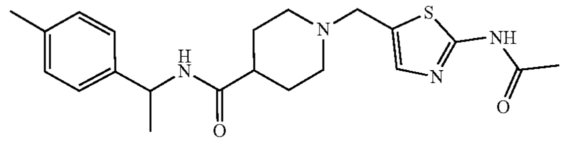 [SMILES: CC(=O)Nc1ncc(CN2CCC(C(=O)NC(C)c3ccc(C)cc3)CC2)s1] | 93.3 | 0.83 |
| B-12 | 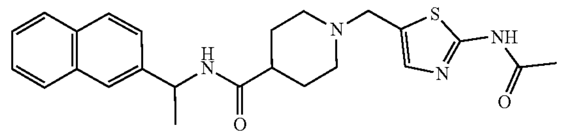 [SMILES: CC(=O)Nc1ncc(CN2CCC(C(=O)NC(C)c3ccc4ccccc4c3)CC2)s1] | 96.8 | 0.25 |
| B-13 | 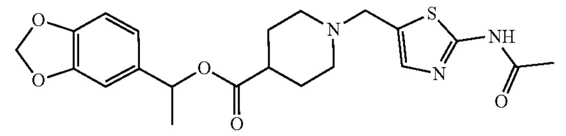 [SMILES: CC(=O)Nc1ncc(CN2CCC(C(=O)OC(C)c3ccc4c(c3)OCO4)CC2)s1] | 98.9 | 0.06 |
| B-14 | 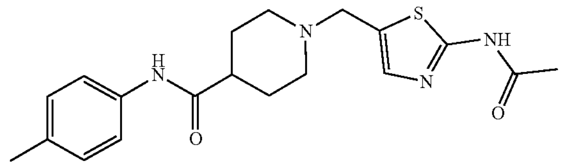 [SMILES: CC(=O)Nc1ncc(CN2CCC(C(=O)Nc3ccc(C)cc3)CC2)s1] | 89.0 | 0.30 |
| B-15 | 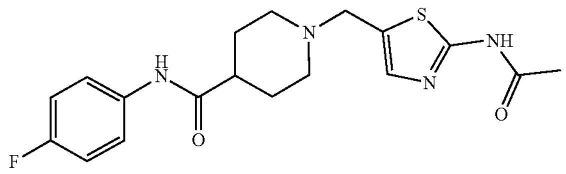 [SMILES: CC(=O)Nc1ncc(CN2CCC(C(=O)Nc3ccc(F)cc3)CC2)s1] | 91.2 | 0.16 |

TABLE 1-continued
| Code | Structure | % of inhibition | $IC_{50}$(μM) |
|---|---|---|---|
| B-16 | 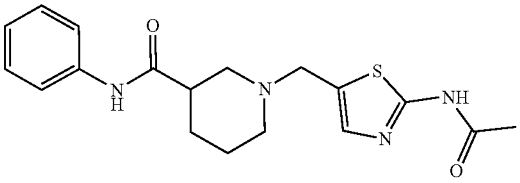 [SMILES: CC(=O)Nc1ncc(CN2CCCC(C(=O)Nc3ccccc3)C2)s1] | 95.5 | 0.23 |
| B-17 | 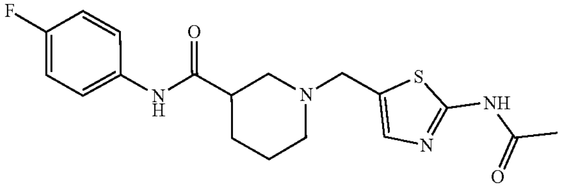 [SMILES: CC(=O)Nc1ncc(CN2CCCC(C(=O)Nc3ccc(F)cc3)C2)s1] | 96.7 | 0.34 |
| B-18 | 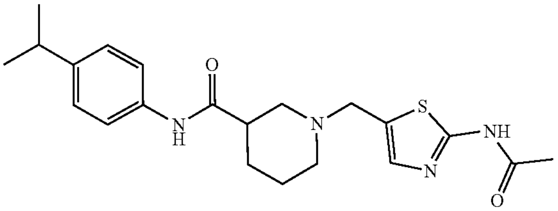 [SMILES: CC(=O)Nc1ncc(CN2CCCC(C(=O)Nc3ccc(C(C)C)cc3)C2)s1] | 96.4 | 0.24 |
| B-19 | 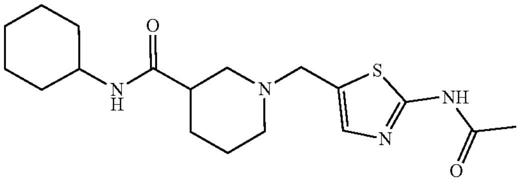 [SMILES: CC(=O)Nc1ncc(CN2CCCC(C(=O)NC3CCCCC3)C2)s1] | 97.6 | 0.45 |
| C-1 | 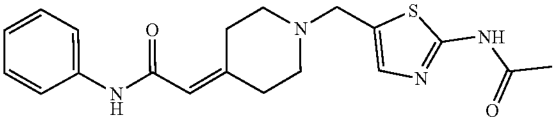 [SMILES: CC(=O)Nc1ncc(CN2CCC(=CC(=O)Nc3ccccc3)CC2)s1] | 96.2 | 0.31 |
| C-2 | 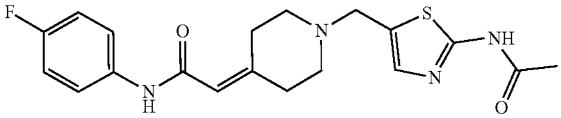 [SMILES: CC(=O)Nc1ncc(CN2CCC(=CC(=O)Nc3ccc(F)cc3)CC2)s1] | 97.1 | 0.17 |
| C-3 | 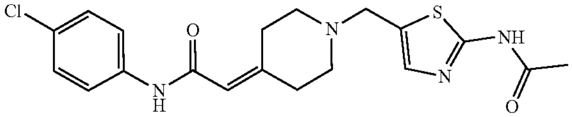 [SMILES: CC(=O)Nc1ncc(CN2CCC(=CC(=O)Nc3ccc(Cl)cc3)CC2)s1] | 97.3 | 0.14 |
| C-4 | 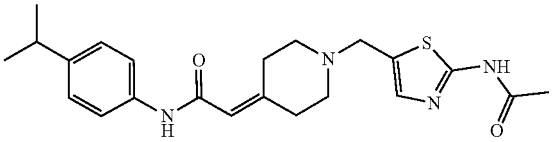 [SMILES: CC(=O)Nc1ncc(CN2CCC(=CC(=O)Nc3ccc(C(C)C)cc3)CC2)s1] | 97.0 | 0.23 |
| C-5 | 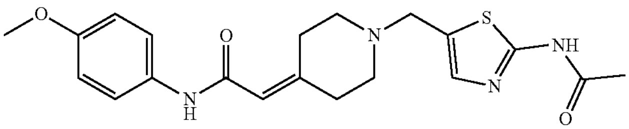 [SMILES: COc1ccc(NC(=O)C=C2CCN(Cc3cnc(NC(C)=O)s3)CC2)cc1] | 94.8 | 0.45 |

TABLE 1-continued

| Code | Structure | % of inhibition | $IC_{50}$(μM) |
|---|---|---|---|
| C-6 | 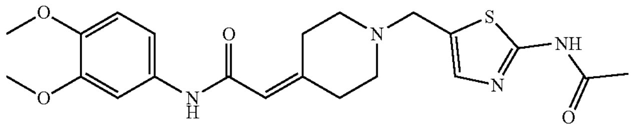 [SMILES: COc1ccc(NC(=O)C=C2CCN(Cc3cnc(NC(C)=O)s3)CC2)cc1OC] | 95.8 | 0.35 |
| C-7 | 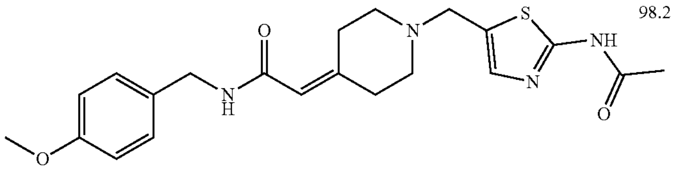 | 98.2 | 0.08 |
| C-8 | 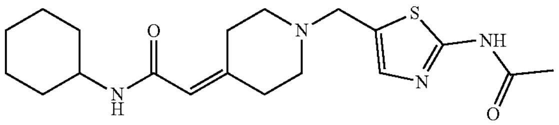 [SMILES: CC(=O)Nc1ncc(CN2CCC(=CC(=O)NC3CCCCC3)CC2)s1] | 97.7 | 0.0.3 |

*N.D.: Not determined

In addition, the concentration-specific inhibitory ability against the human OGA enzyme of the compounds A-34S and A-34R corresponding to the enantiomers of the compound A-34 was shown in the FIGURE, and the $IC_{50}$ concentration values were shown in Table 2 below.

TABLE 2

| Code | Structure | $IC_{50}$ (μM) |
|---|---|---|
| A-34 | 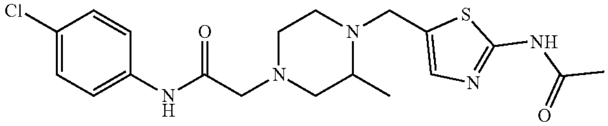 [SMILES: CC(=O)Nc1ncc(CN2CCN(CC(=O)Nc3ccc(Cl)cc3)CC2C)s1] | 0.05 |
| A-34S (S)-form | 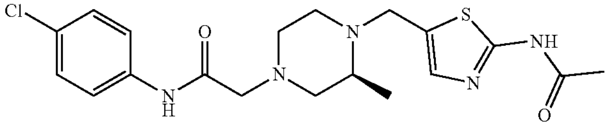 [SMILES: CC(=O)Nc1ncc(CN2CCN(CC(=O)Nc3ccc(Cl)cc3)C[C@@H]2C)s1] | 0.0061 |
| A-34R (R)-form | 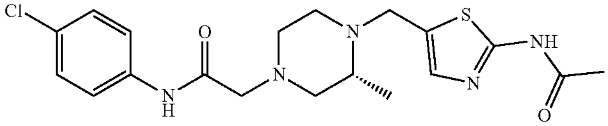 | N.D. |

*N.D.: Not determined

As shown in Table 2, it was confirmed that in the two enantiomers of the compound A-34, an (S)-form compound of A-34 was significantly excellent in the inhibitory ability against the human OGA enzyme.

Compound Name of A-34S:

(S)-2-(4-((2-acetamidothiazol-5-yl)methyl)-3-methylpiperazin-1-yl)-N-(4-chlorophenyl)acetamide Compound Name of A-34R:

(R)-2-(4-((2-acetamidothiazol-5-yl)methyl)-3-methylpiperazin-1-yl)-N-(4-chlorophenyl)acetamide Hereinabove, the present invention has been described with reference to preferred embodiments thereof. It will be understood to those skilled in the art that the present invention may be modified without departing from an essential characteristic of the present invention. Therefore, the disclosed embodiments should be considered in an illustrative viewpoint rather than a restrictive viewpoint. Therefore, the scope of the present invention is indicated by the appended claims including the foregoing description, and differences within the equivalent scope thereof should be construed as being included in the present invention.

INDUSTRIAL APPLICABILITY

The present invention relates to a novel compound having inhibitory activity against O-GlcNAcase, and may be useful as a pharmaceutical composition for treating diseases caused by hyperphosphorylation of tau.

The invention claimed is:

1. A compound represented by Chemical Formula 1 below or a pharmaceutical salt thereof:

[Chemical Formula 1]

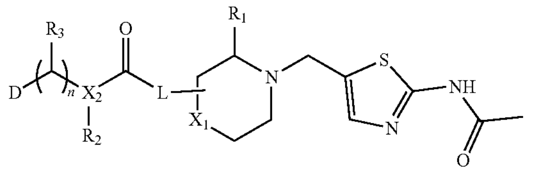

wherein,

D is a ring selected from the group consisting of substitutable C3 to C10 cycloalkyl, substitutable 5-membered unsaturated or aromatic ring, substitutable 6-membered unsaturated or aromatic ring, substitutable 5-membered unsaturated or aromatic heterocyclic ring, and substitutable 6-membered unsaturated or aromatic heterocyclic ring, or a polycyclic ring in which two or more rings selected from the group are fused, $X_1$ is C, N, O or S, $X_2$ is N or O, $R_1$, $R_2$ and $R_3$ are each independently hydrogen or C1 to C5 alkyl, L is a direct bond or a C1 to C12 alkylene group, and n is an integer of 0 to 3.

2. The compound of claim 1, wherein the compound of Chemical Formula 1 above includes compounds represented by Chemical Formulas 2 to 4 below:

[Chemical Formula 2]

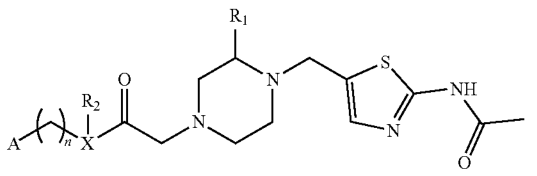

[Chemical Formula 3]

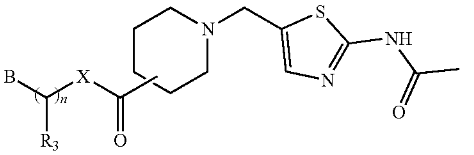

[Chemical Formula 4]

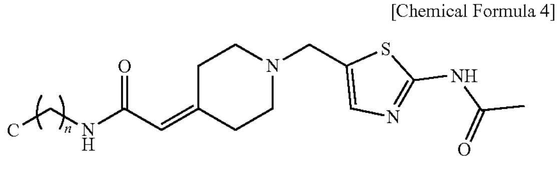

wherein,

A, B, and C are each independently a ring selected from the group consisting of substitutable C3 to C10 cycloalkyl, substitutable 5-membered unsaturated or aromatic ring, substitutable 6-membered unsaturated or aromatic ring, substitutable 5-membered unsaturated or aromatic heterocyclic ring, and substitutable 6-membered unsaturated or aromatic heterocyclic ring, or a polycyclic ring in which two or more rings selected from the group are fused, $R_1$, $R_2$, $R_3$ and n are the same as defined in claim 1 above, and X is N or O.

3. The compound of claim 2, wherein in Chemical Formula 2, A is selected from the following substituents:

A

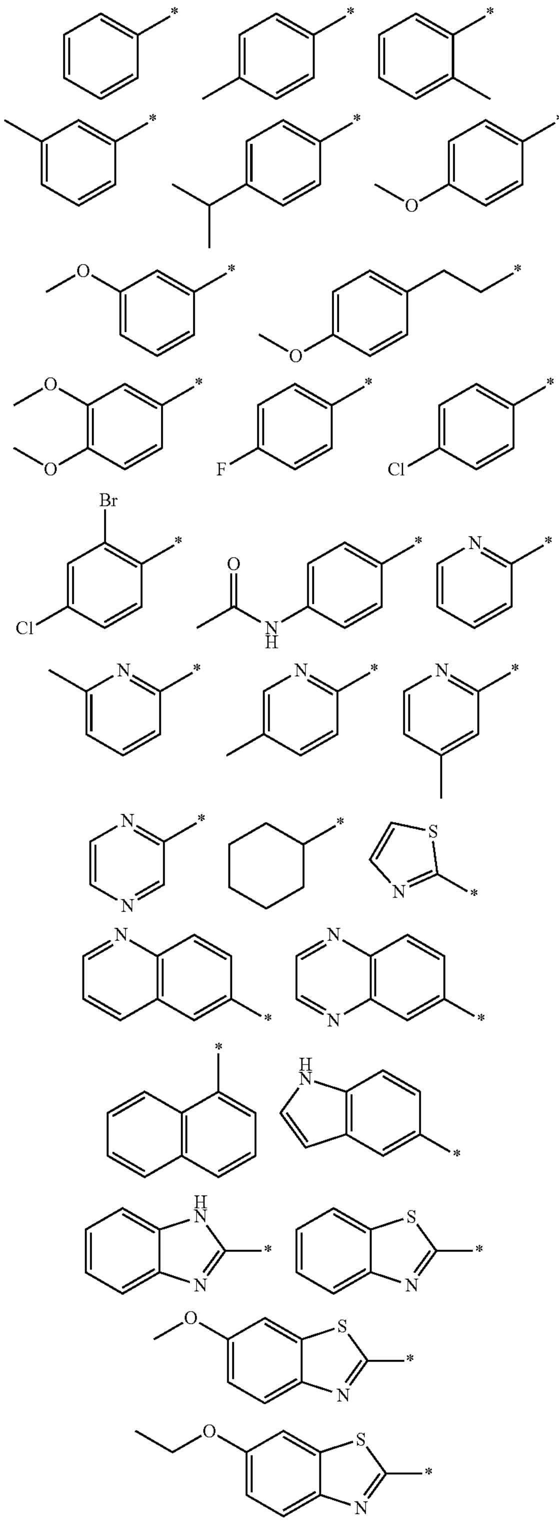

-continued

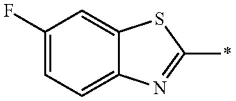
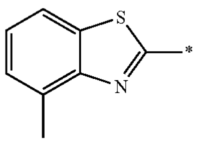
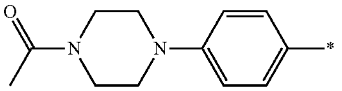
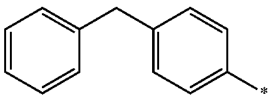
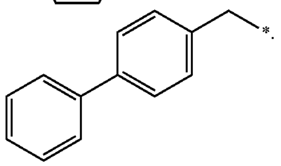

4. The compound of claim 2, wherein in Chemical Formula 3, B is selected from the following substituents:

B

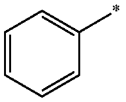
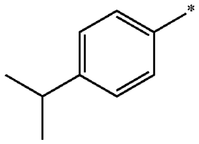
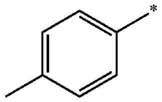
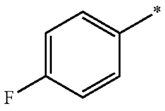
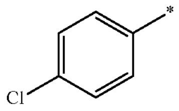
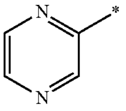
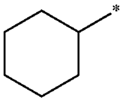
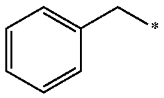
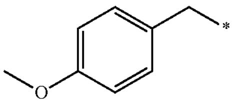

-continued

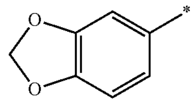
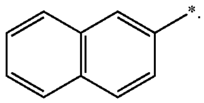

5. The compound of claim 2, wherein in Chemical Formula 4, C is selected from the following substituents:

C:

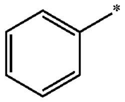
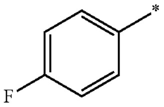
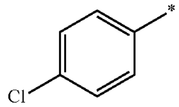
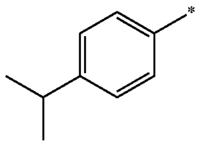
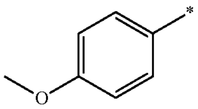
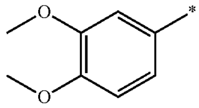
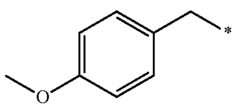
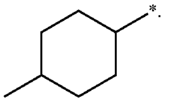

6. The compound of claim 2, wherein the compound of Chemical Formula 2 above includes compounds A-1 to A-41 below:

| Code | Structure | Name |
|---|---|---|
| A-1 | 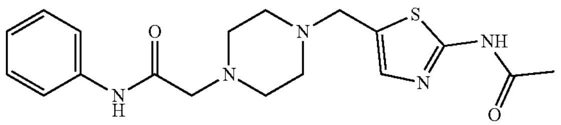 [SMILES: CC(=O)Nc1ncc(CN2CCN(CC(=O)Nc3ccccc3)CC2)s1] | 2-(4-((2-acetamidothiazol-5-yl)methyl)piperazin-1-yl)-N-phenylacetamide |
| A-2 | 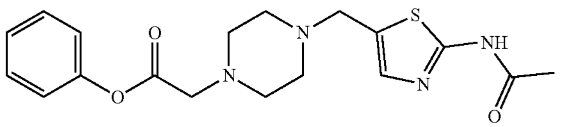 [SMILES: CC(=O)Nc1ncc(CN2CCN(CC(=O)Oc3ccccc3)CC2)s1] | phenyl 2-(4-((2-acetamidothiazol-5-yl)methyl)piperazin-1-yl) acetate |
| A-3 | 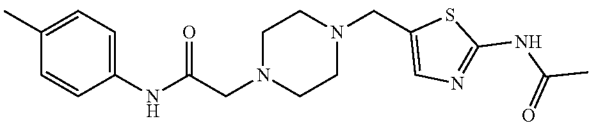 [SMILES: CC(=O)Nc1ncc(CN2CCN(CC(=O)Nc3ccc(C)cc3)CC2)s1] | 2-(4-((2-acetamidothiazol-5-yl)methyl)piperazin-1-yl)-N-(p-tolyl)acetamide |
| A-4 | 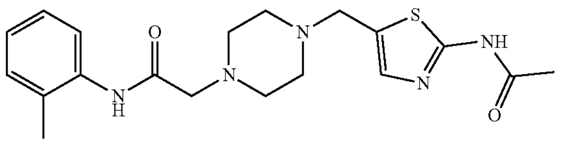 [SMILES: CC(=O)Nc1ncc(CN2CCN(CC(=O)Nc3ccccc3C)CC2)s1] | 2-(4-((2-acctamidothiazol-5-yl)methyl)piperazin-1-yl)-N-(o-tolyl)acetamide |

-continued

| Code | Structure | Name |
|---|---|---|
| A-5 | 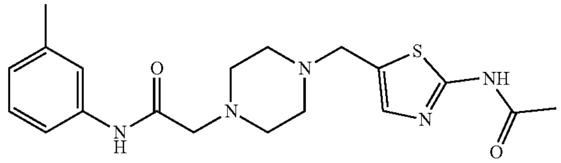 | 2-(4-((2-acetamidothiazol-5-yl)methyl)piperazin-1-yl)-N-o-tolyl)acetamide |
| A-6 | 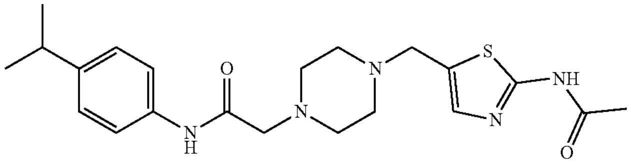 [SMILES: CC(=O)Nc1ncc(CN2CCN(CC(=O)Nc3ccc(C(C)C)cc3)CC2)s1] | 2-(4-((2-acetamidothiazol-5-yl)methyl)piperazin-1-yl)-N-(4-isopropylphenyl) acetamide |
| A-7 | 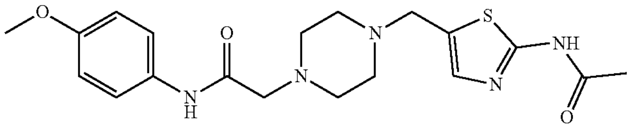 [SMILES: COc1ccc(NC(=O)CN2CCN(Cc3cnc(NC(C)=O)s3)CC2)cc1] | 2-(4-((2-acetamidothiazol-5-yl)methyl)piperazin-1-yl)-N-(4-methoxyphenyl) acetamide |
| A-8 | 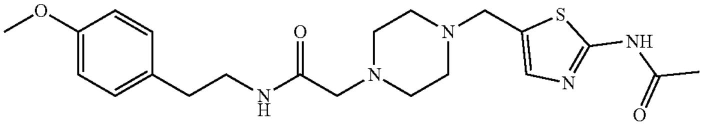 [SMILES: COc1ccc(CCNC(=O)CN2CCN(Cc3cnc(NC(C)=O)s3)CC2)cc1] | 2-(4-((2-acetamidotiazol-3-yl)methyl)piperazin-1-yl)-N-(4-methoxyphenethyl) acetamide |
| A-9 | 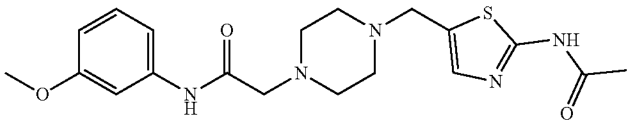 [SMILES: COc1cccc(NC(=O)CN2CCN(Cc3cnc(NC(C)=O)s3)CC2)c1] | 2-(4-((2-acetamidotiazol-5-yl)methyl)piperazin-1-yl)-N-(3-methoxyphenyl) acetamide |
| A-10 | 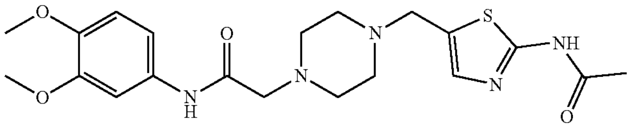 [SMILES: COc1ccc(NC(=O)CN2CCN(Cc3cnc(NC(C)=O)s3)CC2)cc1OC] | 2-(4-((2-acetamidothiazol-5-yl)methyl)piperazin-1-yl)-N-(3,4-dimethoxyphenyl)acetamide |
| A-11 | 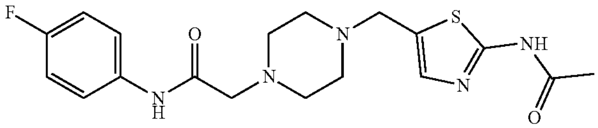 [SMILES: CC(=O)Nc1ncc(CN2CCN(CC(=O)Nc3ccc(F)cc3)CC2)s1] | 2-(4-((2-acetamidoilsazo]-5-yl)methyl)piperazin-1-yl)-N-(4-fluorophonyl)acetamide |
| A-12 | 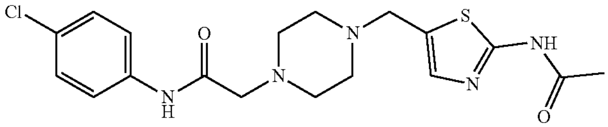 [SMILES: CC(=O)Nc1ncc(CN2CCN(CC(=O)Nc3ccc(Cl)cc3)CC2)s1] | 2-(4-((2-acetamidothiazol-5-yl)methyl)piperazin-1-yl)-N-(4-chlorophenyl)acetamide |
| A-13 | 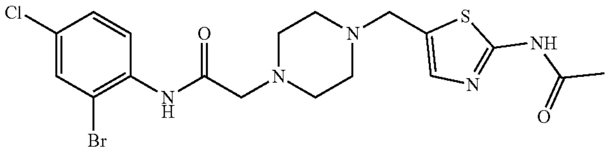 [SMILES: CC(=O)Nc1ncc(CN2CCN(CC(=O)Nc3ccc(Cl)cc3Br)CC2)s1] | 2-(4-((2-acetainidothiazol-5-yl)methyl)piperazin-1-yl)-N-(2-bromo-4-chlorophenyl) acetamide |
| A-14 | 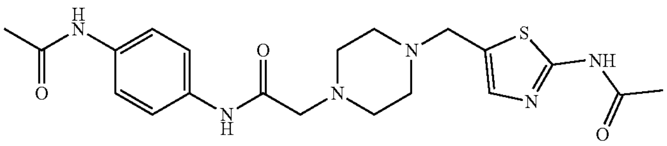 [SMILES: CC(=O)Nc1ccc(NC(=O)CN2CCN(Cc3cnc(NC(C)=O)s3)CC2)cc1] | N-(4-acetamidophenyl)-2-(4-((2-acetamidothiazol-5-yl) methyl)piperazin-1-yl) acetamide |

-continued

| Code | Structure | Name |
|---|---|---|
| A-15 | 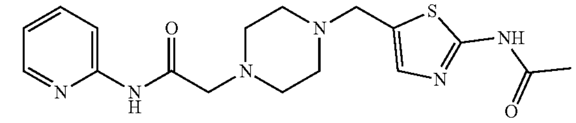 [SMILES: CC(=O)Nc1ncc(CN2CCN(CC(=O)Nc3ccccn3)CC2)s1] | 2-(4-((2-acetamidothiazol-5-yl)methyl)piperazin-1-yl)-N-(pyridin-2-yl)acetamide |
| A-16 | 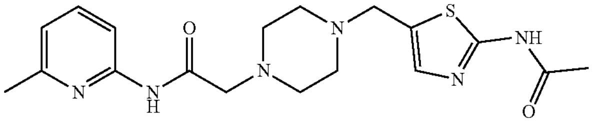 [SMILES: CC(=O)Nc1ncc(CN2CCN(CC(=O)Nc3cccc(C)n3)CC2)s1] | 2-(4-((2-acetamidothiazol-5-yl)methyl)piperazin-1-yl)-N-(6-methylpyridin-2-yl) acetamide |
| A-17 | 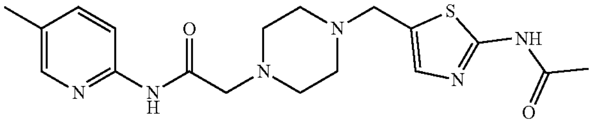 [SMILES: CC(=O)Nc1ncc(CN2CCN(CC(=O)Nc3ccc(C)cn3)CC2)s1] | 2-(4-((2-acetamidothiazol-5-yl)methyl)piperazin-1-yl)-N-(5-methylpyridin-2-y]) acetamide |
| A-18 | 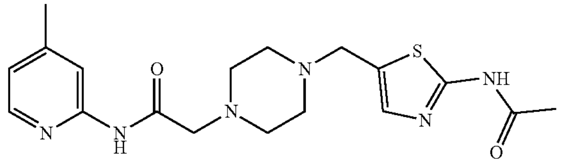 [SMILES: CC(=O)Nc1ncc(CN2CCN(CC(=O)Nc3cc(C)ccn3)CC2)s1] | 2-(4-((2-acetamidothiazol-5-yl)methyl)piperazin-1-yl)-N-(4-methylpyridin-2-yl) acetamide |
| A-19 | 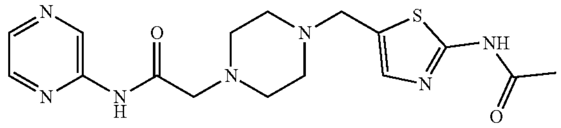 [SMILES: CC(=O)Nc1ncc(CN2CCN(CC(=O)Nc3cnccn3)CC2)s1] | 2-(4-((2-acctamidothiazol-5-yl)methyl)piperazin-1-yl)-N-(pyrazin-2-yl)acetamide |
| A-20 | 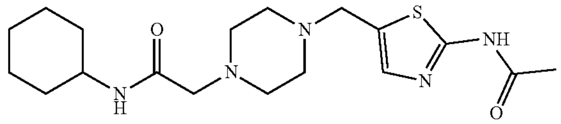 [SMILES: CC(=O)Nc1ncc(CN2CCN(CC(=O)NC3CCCCC3)CC2)s1] | 2-(4-((2-acetamidothiazol-5-yl)methyl)piperazin-1-yl)-N-cyclohexylacetamide |
| A-21 | 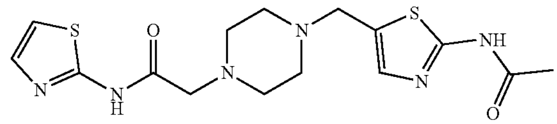 [SMILES: CC(=O)Nc1ncc(CN2CCN(CC(=O)Nc3nccs3)CC2)s1] | 2-(4-((2-acctamidothiazol-5-yl)methyl)piperazin-1-yl)-N-(thiazol-2-yl)acetamide |
| A-22 | 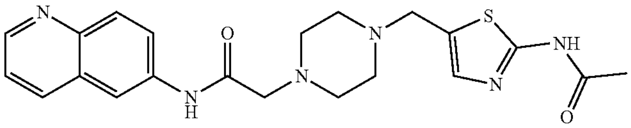 | 2-(4-((2-acetamidothiazol-5-yl)methyl piperazin-1-yl)-N-(quinolin-6-yl)acetamide |
| A-23 | 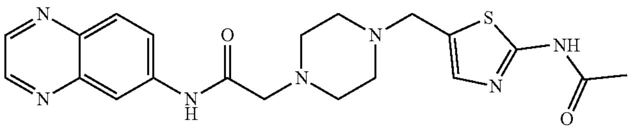 | 2-(4-((2-acetamidothiazol-5-yl)methyl)piperazin-1-yl)-N-(quinoxalin-6-yl)acetamide |
| A-24 | 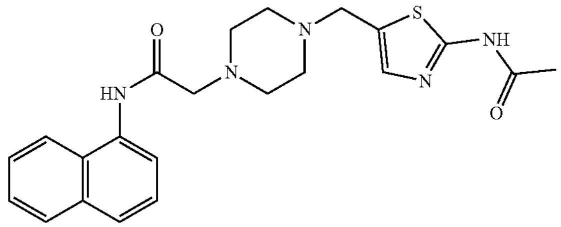 [SMILES: CC(=O)Nc1ncc(CN2CCN(CC(=O)Nc3cccc4ccccc34)CC2)s1] | 2-(4-((2-acetamidothiazol53-yl)methyl)piperazin-1-yl)-N-(naphthalen-1-yl)acetamide |

-continued

| Code | Structure | Name |
|---|---|---|
| A-25 | 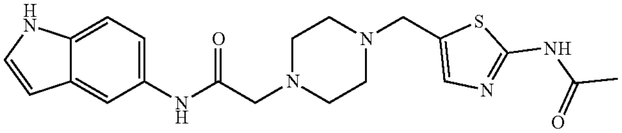 [SMILES: CC(=O)Nc1ncc(CN2CCN(CC(=O)Nc3ccc4[nH]ccc4c3)CC2)s1] | 2-(4-((2-acetamidothiazol-5-yl)methyl)piperazin-1-yl)-N-(1H-indol-5-yl)acetamide |
| A-26 | 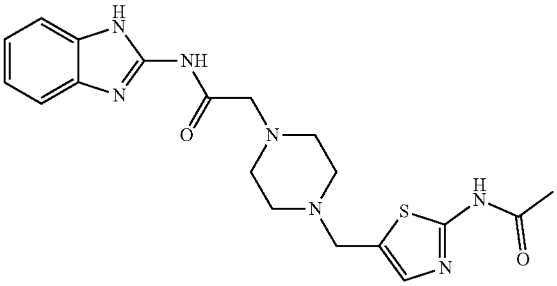 [SMILES: CC(=O)Nc1ncc(CN2CCN(CC(=O)Nc3nc4ccccc4[nH]3)CC2)s1] | 2-(4-((2-acetamidothiazol-5-yl)methylpiperazin-1-yl)-N-(IH-benzo[d]imidazol-2-yl)acetamide |
| A-27 | 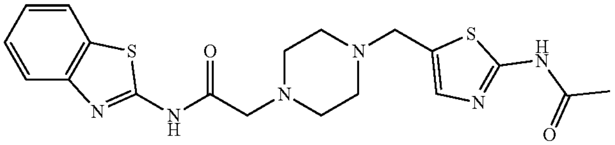 [SMILES: CC(=O)Nc1ncc(CN2CCN(CC(=O)Nc3nc4ccccc4s3)CC2)s1] | 2-(4-((2-acetamidothiazol-5-yl)methyl)piperazin-1-yl)-N-(benzo[d]thiazol-2-yl) acetamide |
| A-28 | 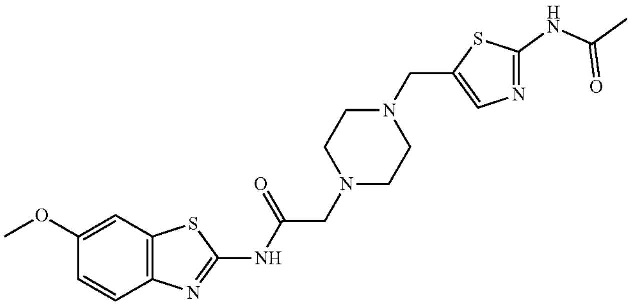 [SMILES: COc1ccc2nc(NC(=O)CN3CCN(Cc4cnc(NC(C)=O)s4)CC3)sc2c1] | 2-(4-((2-acetamidothiazol-5-yl)methyl)piperazin-1-yl)-N-(6-methoxybenzo[d]thiazol-2-yl)acetamide |
| A-29 | 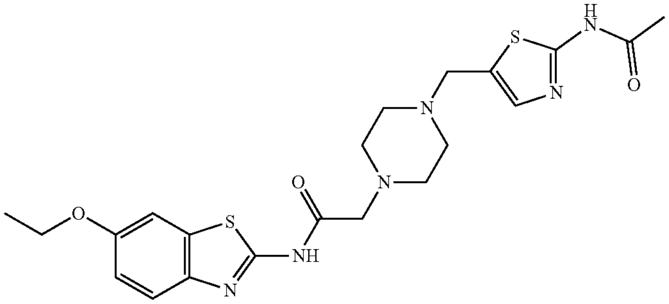 [SMILES: CCOc1ccc2nc(NC(=O)CN3CCN(Cc4cnc(NC(C)=O)s4)CC3)sc2c1] | 2-(4-((2-acetanidothiazol-5-yl)methyl)piperazin-1-yl)-N-(6-ethoxybenzo[d]thiazol-2-yl)acetamide |
| A-30 | 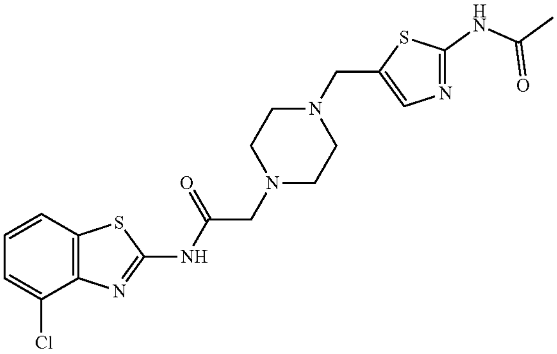 [SMILES: CC(=O)Nc1ncc(CN2CCN(CC(=O)Nc3nc4c(Cl)cccc4s3)CC2)s1] | 2-(4-((2-acetamidothiazol-5 N-(4-chlorobenzo[d]thiazol-2-yl)acetamide |

-continued

| Code | Structure | Name |
|---|---|---|
| A-31 | 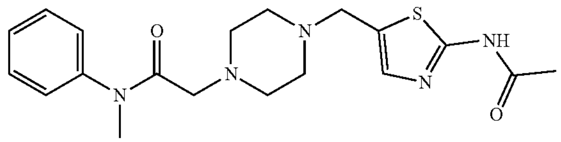 [SMILES: CC(=O)Nc1ncc(CN2CCN(CC(=O)N(C)c3ccccc3)CC2)s1] | 2-(4-((2-acetamidothiazol-5-yl)methyl)piperazin-1-yl)-N-methyl-N-phenylacetamide |
| A-32 | 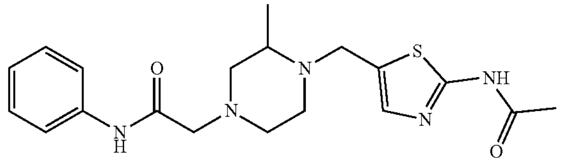 [SMILES: CC(=O)Nc1ncc(CN2CCN(CC(=O)Nc3ccccc3)CC2C)s1] | 2-(4-((2-acetamidothiazol-5-yl)methyl)-3-methylpipenzin-1-yl)-N-phenylacetamide |
| A-33 | 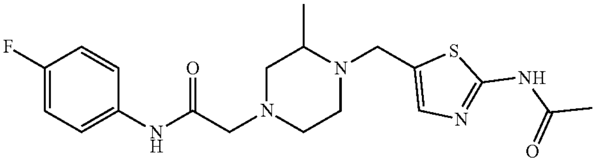 [SMILES: CC(=O)Nc1ncc(CN2CCN(CC(=O)Nc3ccc(F)cc3)CC2C)s1] | 2-(4-((2-acetamidothiazol-5-yl)methyl)-3-methylpiperazin-1-yl)-N-(4-fluorophenyl) acetamide |
| A-34 | 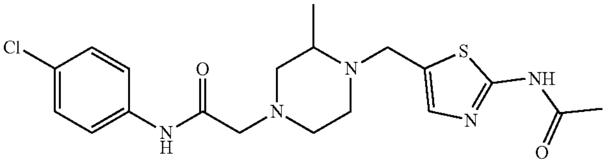 [SMILES: CC(=O)Nc1ncc(CN2CCN(CC(=O)Nc3ccc(Cl)cc3)CC2C)s1] | 2-(4-((2-acetamidothiazol-5-yl)methyl)-3-methylpiperazin-1-yl)-N-(4-chloropbenyl) acetamide |
| A-35 | 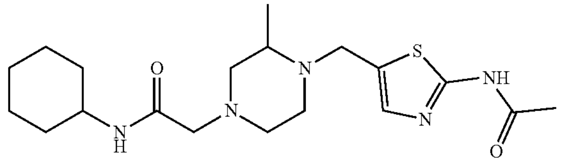 [SMILES: CC(=O)Nc1ncc(CN2CCN(CC(=O)NC3CCCCC3)CC2C)s1] | 2-(4-((2-acetamidothiazol-5-yl)methyl)-3-methylpiperzin-1-yl)-N-cyclohexylacetamide |
| A-36 | 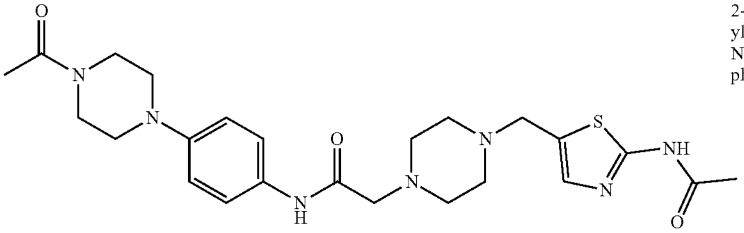 | 2-(4-((2-acetamidothiazol-5-yl)methyl)piperazin-1-yl)-N-(4-(4-acetylpiperazin-1-yl) phenyl)acetamide |
| A-37 | 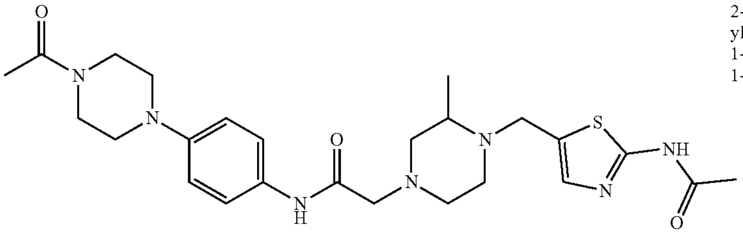 | 2-(4-((2-acetamidothiazol-5-yl)methyl)-3-methylpiperazin-1-yl)-N-(4-(4-acetylpiperazin-1-yl)phenylacetamide |
| A-38 | 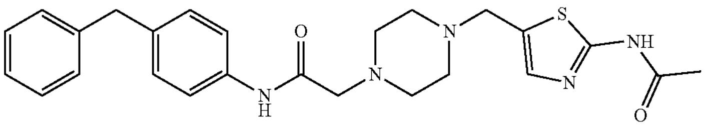 [SMILES: CC(=O)Nc1ncc(CN2CCN(CC(=O)Nc3ccc(Cc4ccccc4)cc3)CC2)s1] | 2-(4-((2-acetamidothiazol-5-yl)methyl)piperazin-1-yl)-N-(4-benzylphenyl)acetamide |

-continued

| Code | Structure | Name |
| --- | --- | --- |
| A-39 | 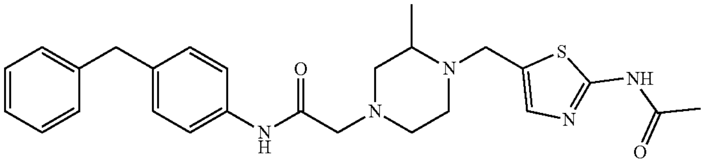 [SMILES: CC(=O)Nc1ncc(CN2CCN(CC(=O)Nc3ccc(Cc4ccccc4)cc3)CC2C)s1] | 2-(4-((2-acetamidothiazol-5-yl)methyl)-3-methylpiperazin-1-yl)-N-(4-benzylphenyl) acetamide |
| A-40 | 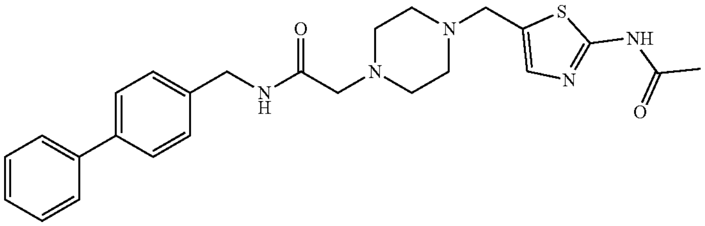 [SMILES: CC(=O)Nc1ncc(CN2CCN(CC(=O)NCc3ccc(-c4ccccc4)cc3)CC2)s1] | N-([1,1'-biphenyl]-4-ylmethyl)-2-(4-((2-acetamidothiazol-5-yl)methyl)piperazin-1-yl)acetamide |
| A-41 | 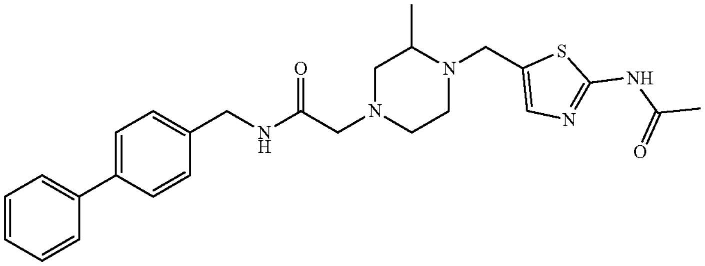 [SMILES: CC(=O)Nc1ncc(CN2CCN(CC(=O)NCc3ccc(-c4ccccc4)cc3)CC2C)s1] | N-([1,1'-biphenyl]-4-ylmethyl)-2-(4-((2-acetamidothiazol-5-ylmethyl)-3-methylpiperazin-1-yl)acetamide. |

7. The compound of claim 2, wherein the compound of Chemical Formula 3 above includes compounds B-1 to B-19 below:

| Code | Structure | Name |
| --- | --- | --- |
| B-1 | 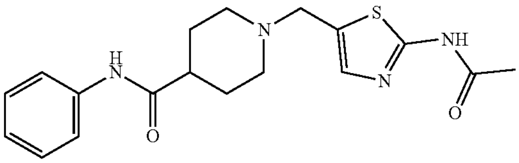 [SMILES: CC(=O)Nc1ncc(CN2CCC(C(=O)Nc3ccccc3)CC2)s1] | 1-((2-acetantidothiazol-5-yl)methyl)-N-phenylpiperidine-4-carboxamide |
| B-2 | 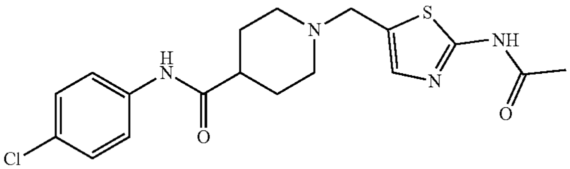 [SMILES: CC(=O)Nc1ncc(CN2CCC(C(=O)Nc3ccc(Cl)cc3)CC2)s1] | 1-((2-acetamidothiazol-5-yl)methyl)-N-(4-chlorophenyl) piperidine-4-carboxamide |
| B-3 | 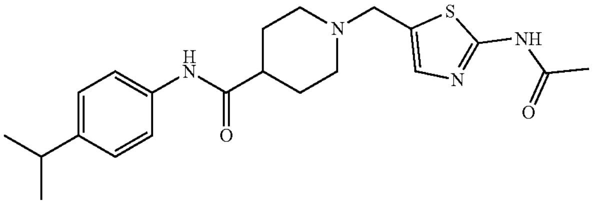 [SMILES: CC(=O)Nc1ncc(CN2CCC(C(=O)Nc3ccc(C(C)C)cc3)CC2)s1] | 1-((2-acetamidothiazol-5-ylmethyl)-N-(4-isopropylphenyl) piperidine-4-carboxamide |

-continued

| Code | Structure | Name |
|---|---|---|
| B-4 | 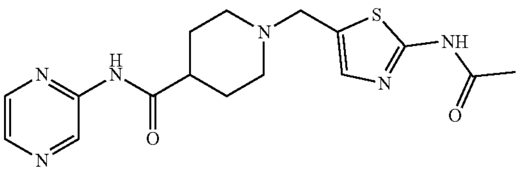 [SMILES: CC(=O)Nc1ncc(CN2CCC(C(=O)Nc3cnccn3)CC2)s1] | 1-((2-acetamidothiazol-5-yl)methyl)-N-(pyrazin-2-yl)piperidine-4-carboxamide |
| B-5 | 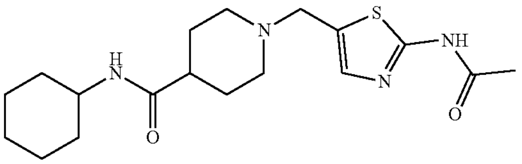 [SMILES: CC(=O)Nc1ncc(CN2CCC(C(=O)NC3CCCCC3)CC2)s1] | 1-((2-acetamidothiazol-5-ylmethyl)-N-cyclohexylpiperidine-4-carboxamide |
| B-6 | 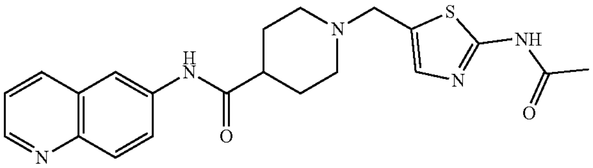 [SMILES: CC(=O)Nc1ncc(CN2CCC(C(=O)Nc3ccc4ncccc4c3)CC2)s1] | 1-((2-acciamidothiazol-5-yl)methyl)-A-(quinolin-6-ybpiperidine-4-carboxamide |
| B-7 | 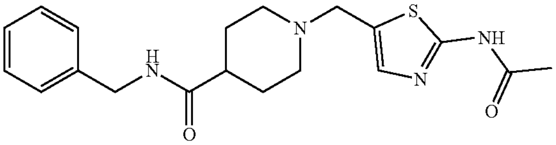 [SMILES: CC(=O)Nc1ncc(CN2CCC(C(=O)NCc3ccccc3)CC2)s1] | 1-((2-acetamidothiazol-5-yl)methyl)-A-benzylpiperidine-4-carboxamide |
| B-8 | 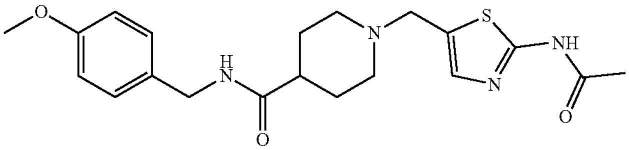 [SMILES: COc1ccc(CNC(=O)C2CCN(Cc3cnc(NC(C)=O)s3)CC2)cc1] | 1-((2-acctamidothiazol-5-yl)methyl)-N-(4-methoxybenzyl) piperidine-4-carboxamide |
| B-9 | 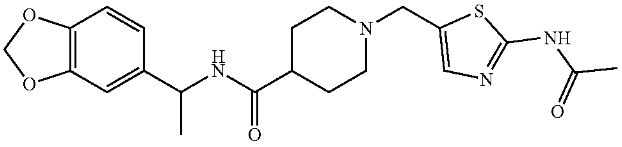 [SMILES: CC(=O)Nc1ncc(CN2CCC(C(=O)NC(C)c3ccc4c(c3)OCO4)CC2)s1] | 1-((2-acetamidothiazol-5-yl)methyl-N-(1-(benzo [d][1,3]dioxol-5-yl)ethyl) piperidine-4-carboxamide |
| B-10 | 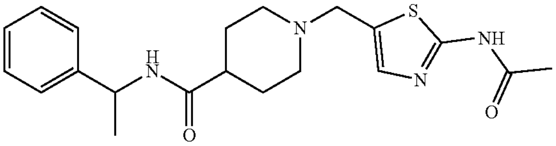 [SMILES: CC(=O)Nc1ncc(CN2CCC(C(=O)NC(C)c3ccccc3)CC2)s1] | 1-((2-acetamidothiazol-5-yl)methyl)-N-(1-phenylethyl)piperidine-4-carboxamide |
| B-11 | 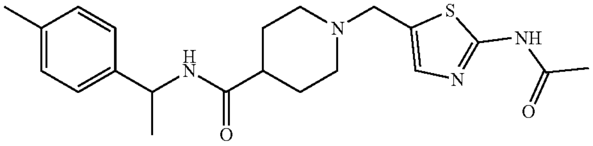 [SMILES: CC(=O)Nc1ncc(CN2CCC(C(=O)NC(C)c3ccc(C)cc3)CC2)s1] | 1-((2-acetamidothiazol-5-yl)methyl)-N-(1-(p-tol yl)ethyl)piperidine-4-carboxamide |
| B-12 | 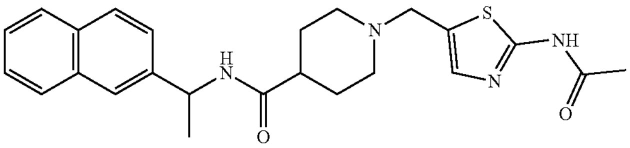 [SMILES: CC(=O)Nc1ncc(CN2CCC(C(=O)NC(C)c3ccc4ccccc4c3)CC2)s1] | 1-((2-acetamidothiazol-5-ylmethyl)-N-(1-(naphthalen-2-yl)ethyl) piperidine-4-carboxamide |

-continued

| Code | Structure | Name |
|---|---|---|
| B-13 | 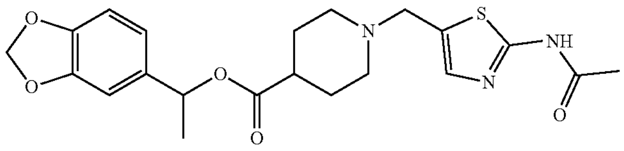 [SMILES: CC(=O)Nc1ncc(CN2CCC(C(=O)OC(C)c3ccc4c(c3)OCO4)CC2)s1] | 1-(benzo[d][1,3]dioxol-5-yl)ethyl 1-((2-acetamidothiazol-5-yl)methyl) piperidine-4-carboxylate |
| B-14 | 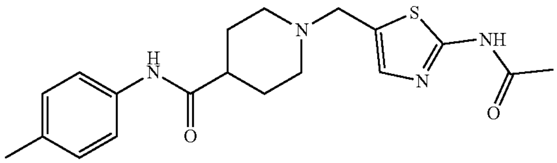 [SMILES: CC(=O)Nc1ncc(CN2CCC(C(=O)Nc3ccc(C)cc3)CC2)s1] | 1-((2-acetamidothiazol-5-yl)methyl)-N-(p-tolyl) piperidine-4-carboxamide |
| B-15 | 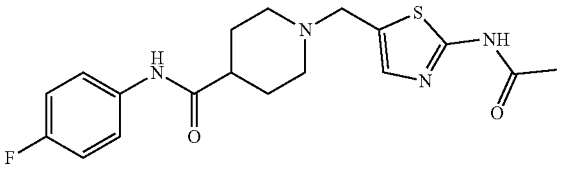 [SMILES: CC(=O)Nc1ncc(CN2CCC(C(=O)Nc3ccc(F)cc3)CC2)s1] | 1-((2-acetamidothiazol-5-yl)methyl)-N-(4-fluorophenyl) piperidine-4-carboxamide |
| B-16 | 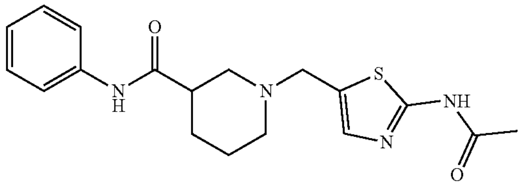 [SMILES: CC(=O)Nc1ncc(CN2CCCC(C(=O)Nc3ccccc3)C2)s1] | 1-((2-acetamidothiazol-5-yl)methyl)-N-phenylpiperdine-3-carboxamide |
| B-17 | 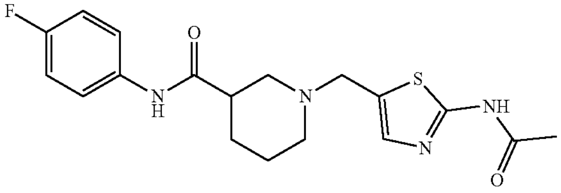 [SMILES: CC(=O)Nc1ncc(CN2CCCC(C(=O)Nc3ccc(F)cc3)C2)s1] | 1-((2-acetamidothiazol-5-yl)methyl)-N-(4-fluorophenyl)piperdine-3-carboxamide |
| B-18 | 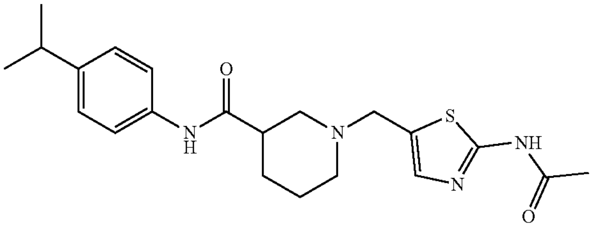 [SMILES: CC(=O)Nc1ncc(CN2CCCC(C(=O)Nc3ccc(C(C)C)cc3)C2)s1] | 1-((2-acetamidothiazol-5-yl)methyl)-N-(4-isopropylphenyl)piperdine-3-carboxamide |
| B-19 | 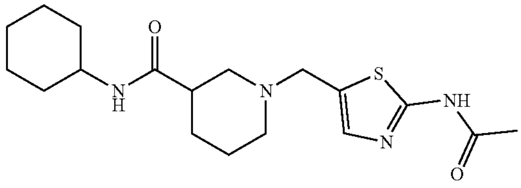 [SMILES: CC(=O)Nc1ncc(CN2CCCC(C(=O)NC3CCCCC3)C2)s1] | 1-((2-acetamidothiazol-5-yl)methyl)-N-(4-cyclohexylpiperdine-3-carboxamide. |

8. The compound of claim 2, wherein the compound of Chemical Formula 4 above includes compounds C-1 to C-8 below:

| Code | Structure | Name |
|---|---|---|
| C-1 | 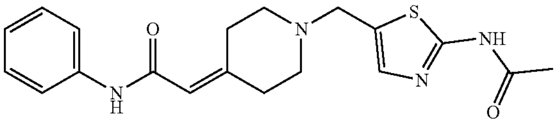 [SMILES: CC(=O)Nc1ncc(CN2CCC(=CC(=O)Nc3ccccc3)CC2)s1] | 2-(1-((2-acctamidothiazol-5-yl)methyl)piperidin-4-ylidene)-N-phenylacetamide |
| C-2 | 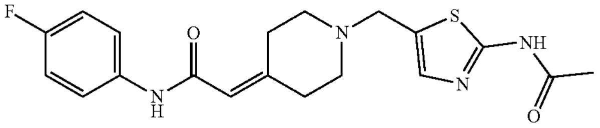 [SMILES: CC(=O)Nc1ncc(CN2CCC(=CC(=O)Nc3ccc(F)cc3)CC2)s1] | 2-(1-((2-acetamidothiazol-5-ylmethyl)piperidin-4-ylidene)-N-(4-fluoro phenyl)acetamide |
| C-3 | 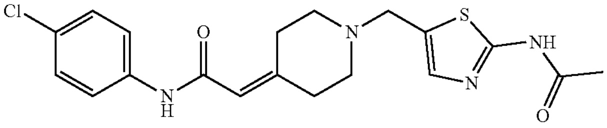 [SMILES: CC(=O)Nc1ncc(CN2CCC(=CC(=O)Nc3ccc(Cl)cc3)CC2)s1] | 2-(1-((2-acetamidothiazol-5-ylmethyl)piperidin-4-ylidene)-N-(4-chloro phenyl)acetamide |
| C-4 | 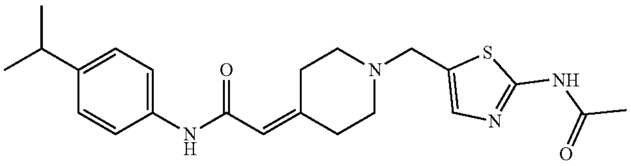 [SMILES: CC(=O)Nc1ncc(CN2CCC(=CC(=O)Nc3ccc(C(C)C)cc3)CC2)s1] | 2-(1-((2-acetamidothiazol-5-yl)methyl)piperidin-4-ylidene)-N-(4-isopropylphenyl) acetamide |
| C-5 | 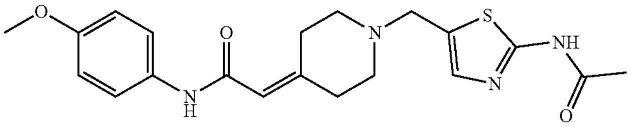 [SMILES: COc1ccc(NC(=O)C=C2CCN(Cc3cnc(NC(C)=O)s3)CC2)cc1] | 2-(1-((2-acetamidothiazol-5-yl)methyl)piperidin-4-ylidene)-N-(4-methoxyphenyl)acetamide |
| C-6 | 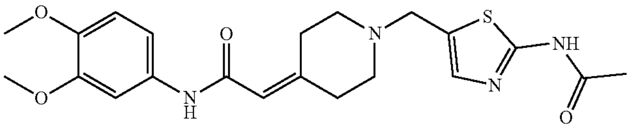 [SMILES: COc1ccc(NC(=O)C=C2CCN(Cc3cnc(NC(C)=O)s3)CC2)cc1OC] | 2-(1-((2-acetamidothiazol-5-yl)methyl)piperidin-4-ylidene)-N-(3,4-dimethoxyphenyl) acetamide |
| C-7 | 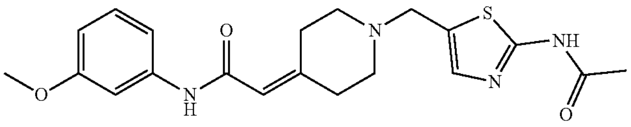 [SMILES: COc1cccc(NC(=O)C=C2CCN(Cc3cnc(NC(C)=O)s3)CC2)c1] | 2-(1-((2-acetamidothiazol)-5-yl)methylppiperidin-4-ylidene)-N-(4-methoxybenzyl) acetamide |
| C-8 | 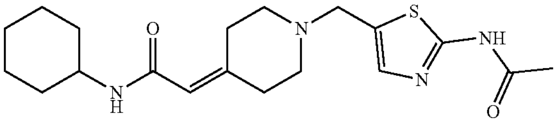 [SMILES: CC(=O)Nc1ncc(CN2CCC(=CC(=O)NC3CCCCC3)CC2)s1] | 2-(1-((2-acetamidothiazol-5-yl)methyl)piperidin-4-ylidene)-N-cyclohexylacetamide. |

9. The compound of claim 6, wherein the compound A-34 is a compound A-34S represented by Chemical Formula 5 below as an(S)-form compound of enantiomers:

[Chemical Formula 5]

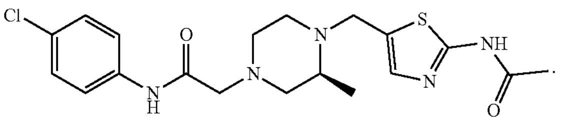

10. A pharmaceutical composition for treating diseases caused by hyperphosphorylation of tau, comprising the compound according to claim 1 or a pharmaceutical salt thereof as an active ingredient.

11. A method for treating a disease caused by hyperphosphorylation of tau, the method comprising administering the pharmaceutical composition according to claim 10.

12. The method of claim 11, wherein the disease is selected from the group consisting of cerebral stroke, stroke, memory loss, memory impairment, dementia, amnesia, Parkinson's disease, Alzheimer's disease, Pick's disease, Creutzfeld-Jakob disease, Huntington's disease, multiple sclerosis, amyotrophic lateral sclerosis (ALS), frontotemporal dementia (FTD), progressive supranuclear palsy (PSAP), corticobasal degeneration (CBD), and Lou Gehrig's disease.

* * * * *